(12) United States Patent
Hall et al.

(10) Patent No.: US 8,871,471 B2
(45) Date of Patent: Oct. 28, 2014

(54) METHODS FOR RAPID FORENSIC DNA ANALYSIS

(75) Inventors: Thomas A. Hall, Oceanside, CA (US); Steven A. Hofstadler, Vista, CA (US); Kristin Sannes-Lowery, Vista, CA (US)

(73) Assignee: IBIS Biosciences, Inc., Carlsbad, CA (US)

( * ) Notice: Subject to any disclaimer, the term of this patent is extended or adjusted under 35 U.S.C. 154(b) by 1189 days.

(21) Appl. No.: 12/528,282

(22) PCT Filed: Feb. 25, 2008

(86) PCT No.: PCT/US2008/054926
§ 371 (c)(1),
(2), (4) Date: Mar. 16, 2010

(87) PCT Pub. No.: WO2008/104002
PCT Pub. Date: Aug. 28, 2008

(65) Prior Publication Data
US 2010/0184035 A1 Jul. 22, 2010

Related U.S. Application Data

(60) Provisional application No. 60/891,479, filed on Feb. 23, 2007, provisional application No. 60/941,641, filed on Jun. 1, 2007.

(51) Int. Cl.
*C12P 19/34* (2006.01)
*C12Q 1/68* (2006.01)

(52) U.S. Cl.
CPC .................................. *C12Q 1/6872* (2013.01)
USPC .......................................................... 435/91.2

(58) Field of Classification Search
USPC ....................................................... 435/91.2
See application file for complete search history.

(56) References Cited

U.S. PATENT DOCUMENTS

| | | | |
|---|---|---|---|
| 4,075,475 A | 2/1978 | Risby et al. |
| 4,683,195 A | 7/1987 | Mullis et al. |
| 4,683,202 A | 7/1987 | Mullis |
| 4,965,188 A | 10/1990 | Mullis et al. |
| 4,965,190 A | 10/1990 | Woo et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,645,994 A | 7/1997 | Huang |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,705,332 A | 1/1998 | Roll |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |

(Continued)

FOREIGN PATENT DOCUMENTS

| | | |
|---|---|---|
| DE | 19732086 A1 | 1/1999 |
| DE | 19802905 A1 | 7/1999 |

(Continued)

OTHER PUBLICATIONS

Aaserud D.J., et al., "Accurate Base Composition of Double-Strand DNA by Mass Spectrometry," American Society for Mass Spectrometry, 1996, vol. 7 (12), pp. 1266-1269.
Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.
Adam E., et al., "Characterization of Intertype Specific Epitopes on Adenovirus Hexons," Archives of Virology, 1998, vol. 143 (9), pp. 1669-1682.
Adam E., et al., "Intertype Specific Epitope Structure of Adenovirus Hexon," Acta Microbiologica et Immunologica Hungarica, 1998, vol. 45 (3-4), pp. 311-316.
Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.

(Continued)

*Primary Examiner* — Cynthia B Wilder
(74) *Attorney, Agent, or Firm* — David A. Casimir; Casimir Jones S.C.

(57) ABSTRACT

The present invention provides methods and primer pairs for rapid, high-resolution forensic analysis of DNA and STR-typing by using amplification and mass spectrometry, determining the molecular masses and calculating base compositions of amplification products and comparing the molecular masses with the molecular masses of theoretical amplicons indexed in a database.

14 Claims, 22 Drawing Sheets

(56) References Cited

U.S. PATENT DOCUMENTS

| | | |
|---|---|---|
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B1 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |

(56) References Cited

U.S. PATENT DOCUMENTS

| | | |
|---|---|---|
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,921,817 B1 | 7/2005 | Banerjee |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 7,956,175 B2 | 6/2011 | Sampath et al. |
| 8,017,322 B2 | 9/2011 | Ecker et al. |
| 8,017,358 B2 | 9/2011 | Ecker et al. |
| 8,017,743 B2 | 9/2011 | Ecker et al. |
| 8,026,084 B2 | 9/2011 | Ecker et al. |
| 8,046,171 B2 | 10/2011 | Ecker et al. |
| 8,057,993 B2 | 11/2011 | Ecker et al. |
| 8,071,309 B2 | 12/2011 | Ecker et al. |
| 8,073,627 B2 | 12/2011 | Ecker et al. |
| 8,158,354 B2 | 4/2012 | Hofstadler et al. |
| 8,298,760 B2 | 10/2012 | Ecker et al. |
| 8,380,442 B2 | 2/2013 | Ecker et al. |
| 8,407,010 B2 | 3/2013 | Hofstadler et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0253583 A1 | 12/2004 | Ecker et al. |
| 2004/0253619 A1 | 12/2004 | Ecker et al. |
| 2005/0009053 A1 | 1/2005 | Boecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0014190 A1* | 1/2006 | Hennessy ........................ 435/6 |
| 2006/0020391 A1 | 1/2006 | Kreiswirth et al. |
| 2006/0121520 A1 | 6/2006 | Ecker et al. |
| 2006/0172330 A1 | 8/2006 | Osborn et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2010/0070194 A1 | 3/2010 | Ecker et al. |

(56) References Cited

U.S. PATENT DOCUMENTS

| | | |
|---|---|---|
| 2010/0145626 A1 | 6/2010 | Ecker et al. |
| 2011/0172925 A1 | 7/2011 | Ecker et al. |
| 2012/0122086 A1 | 5/2012 | Ecker et al. |
| 2012/0123685 A1 | 5/2012 | Ecker et al. |
| 2013/0124099 A1 | 5/2013 | Ecker et al. |
| 2013/0337452 A1 | 12/2013 | Hofstadler et al. |

FOREIGN PATENT DOCUMENTS

| | | |
|---|---|---|
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 0620862 A1 | 10/1994 |
| EP | 633321 A1 | 1/1995 |
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1748072 A1 | 1/2007 |
| FR | 2811321 A1 | 1/2002 |
| GB | 2325002 A | 11/1998 |
| GB | 2339905 A | 2/2000 |
| JP | 5276999 A2 | 10/1993 |
| JP | 11137259 A | 5/1999 |
| JP | 24024206 A2 | 1/2004 |
| JP | 2004000200 A2 | 1/2004 |
| JP | 24201679 A2 | 7/2004 |
| JP | 2004201641 A | 7/2004 |
| WO | WO8803957 A1 | 6/1988 |
| WO | WO9015157 A1 | 12/1990 |
| WO | WO9205182 A1 | 4/1992 |
| WO | WO9208117 A1 | 5/1992 |
| WO | WO9209703 A1 | 6/1992 |
| WO | WO9219774 A1 | 11/1992 |
| WO | WO9303186 A1 | 2/1993 |
| WO | WO9305182 A1 | 3/1993 |
| WO | WO9308297 A1 | 4/1993 |
| WO | WO9416101 A2 | 7/1994 |
| WO | WO9419490 A1 | 9/1994 |
| WO | WO9421822 A1 | 9/1994 |
| WO | WO9504161 A1 | 2/1995 |
| WO | WO9511996 A1 | 5/1995 |
| WO | WO9513395 A1 | 5/1995 |
| WO | WO9513396 A2 | 5/1995 |
| WO | WO9531997 A1 | 11/1995 |
| WO | WO9606187 A1 | 2/1996 |
| WO | WO9616186 A1 | 5/1996 |
| WO | WO9629431 A2 | 9/1996 |
| WO | WO9632504 A2 | 10/1996 |
| WO | WO9635450 A1 | 11/1996 |
| WO | WO9637630 A1 | 11/1996 |
| WO | WO9733000 A1 | 9/1997 |
| WO | WO9734909 A1 | 9/1997 |
| WO | WO9737041 A2 | 10/1997 |
| WO | WO9747766 A1 | 12/1997 |
| WO | WO9803684 A1 | 1/1998 |
| WO | WO9812355 A1 | 3/1998 |
| WO | WO9814616 A1 | 4/1998 |
| WO | WO9815652 A1 | 4/1998 |
| WO | WO9820020 A2 | 5/1998 |
| WO | WO9820157 A2 | 5/1998 |
| WO | WO9820166 A2 | 5/1998 |
| WO | WO9826095 A1 | 6/1998 |
| WO | WO9831830 A1 | 7/1998 |
| WO | WO9835057 A1 | 8/1998 |
| WO | WO9840520 A1 | 9/1998 |
| WO | WO9854571 A1 | 12/1998 |
| WO | WO9854751 A1 | 12/1998 |
| WO | WO9905319 A2 | 2/1999 |
| WO | WO9912040 A2 | 3/1999 |
| WO | WO9913104 A1 | 3/1999 |
| WO | WO9914375 A2 | 3/1999 |
| WO | WO9929898 A2 | 6/1999 |
| WO | WO9931278 A1 | 6/1999 |
| WO | WO9957318 A2 | 11/1999 |
| WO | WO9958713 A2 | 11/1999 |
| WO | WO9960183 A1 | 11/1999 |
| WO | WO0032750 A1 | 6/2000 |
| WO | WO0038636 A1 | 7/2000 |
| WO | WO0063362 A1 | 10/2000 |
| WO | WO0066762 A2 | 11/2000 |
| WO | WO0066789 A2 | 11/2000 |
| WO | WO0077260 A1 | 12/2000 |
| WO | WO0100828 A2 | 1/2001 |
| WO | WO0107648 A1 | 2/2001 |
| WO | WO0112853 A1 | 2/2001 |
| WO | WO0120018 A2 | 3/2001 |
| WO | WO0123604 A2 | 4/2001 |
| WO | WO0123608 A2 | 4/2001 |
| WO | WO0127857 A2 | 4/2001 |
| WO | WO0132930 A1 | 5/2001 |
| WO | WO0140497 A2 | 6/2001 |
| WO | WO0146404 A1 | 6/2001 |
| WO | WO0151661 A2 | 7/2001 |
| WO | WO0151662 A1 | 7/2001 |
| WO | WO0157263 A1 | 8/2001 |
| WO | WO0157518 A2 | 8/2001 |
| WO | WO0173119 A2 | 10/2001 |
| WO | WO0173199 A1 | 10/2001 |
| WO | WO0177392 A2 | 10/2001 |
| WO | WO0196388 A2 | 12/2001 |
| WO | WO0202811 A2 | 1/2002 |
| WO | WO0210186 A1 | 2/2002 |
| WO | WO0210444 A1 | 2/2002 |
| WO | WO0218641 A2 | 3/2002 |
| WO | WO0221108 A2 | 3/2002 |
| WO | WO0222873 A1 | 3/2002 |
| WO | WO0224876 A2 | 3/2002 |
| WO | WO0250307 A1 | 6/2002 |
| WO | WO02057491 A2 | 7/2002 |
| WO | WO02070664 A2 | 9/2002 |
| WO | WO02070728 A2 | 9/2002 |
| WO | WO02070737 A2 | 9/2002 |
| WO | WO02077278 A1 | 10/2002 |
| WO | WO02099034 A2 | 12/2002 |
| WO | WO02099095 A2 | 12/2002 |
| WO | WO02099129 A2 | 12/2002 |
| WO | WO02099130 A2 | 12/2002 |
| WO | WO03001976 A2 | 1/2003 |
| WO | WO03002750 A2 | 1/2003 |
| WO | WO03008636 A2 | 1/2003 |
| WO | WO03012058 A2 | 2/2003 |
| WO | WO03012074 A2 | 2/2003 |
| WO | WO03014382 A2 | 2/2003 |
| WO | WO03016546 A1 | 2/2003 |
| WO | WO03018636 A2 | 3/2003 |
| WO | WO03020890 A2 | 3/2003 |
| WO | WO03033732 A2 | 4/2003 |
| WO | WO03054162 A2 | 7/2003 |
| WO | WO03054755 A2 | 7/2003 |
| WO | WO03060136 A2 | 7/2003 |
| WO | WO03075955 A1 | 9/2003 |
| WO | WO03088979 A2 | 10/2003 |
| WO | WO03093506 A2 | 11/2003 |
| WO | WO03097869 A2 | 11/2003 |
| WO | WO03100035 A2 | 12/2003 |
| WO | WO03100068 A1 | 12/2003 |
| WO | WO03102191 A1 | 12/2003 |
| WO | WO03104410 A2 | 12/2003 |
| WO | WO03106635 A2 | 12/2003 |
| WO | WO2004003511 A2 | 1/2004 |
| WO | WO2004009849 A1 | 1/2004 |
| WO | WO2004011651 A1 | 2/2004 |
| WO | WO2004013357 A2 | 2/2004 |
| WO | WO2004040013 A1 | 5/2004 |
| WO | WO2004044123 A2 | 5/2004 |

(56) References Cited

FOREIGN PATENT DOCUMENTS

| WO | WO2004044247 A2 | 5/2004 |
|---|---|---|
| WO | WO2004052175 A2 | 6/2004 |
| WO | WO2004053076 A2 | 6/2004 |
| WO | WO2004053141 A2 | 6/2004 |
| WO | WO2004053164 A1 | 6/2004 |
| WO | WO2004060278 A2 | 7/2004 |
| WO | WO2004070001 A2 | 8/2004 |
| WO | WO2004072230 A2 | 8/2004 |
| WO | WO2004072231 A2 | 8/2004 |
| WO | WO2004101809 A2 | 11/2004 |
| WO | WO2005003384 A1 | 1/2005 |
| WO | WO2005009202 A2 | 2/2005 |
| WO | WO2005012572 A1 | 2/2005 |
| WO | WO2005024046 A2 | 3/2005 |
| WO | WO2005036369 A2 | 4/2005 |
| WO | WO2005054454 A1 | 6/2005 |
| WO | WO2005075686 A1 | 8/2005 |
| WO | WO2005086634 A2 | 9/2005 |
| WO | WO2005091971 A2 | 10/2005 |
| WO | WO2005098047 A2 | 10/2005 |
| WO | WO2005116263 A2 | 12/2005 |
| WO | WO2006089762 A1 | 8/2006 |
| WO | WO2006094238 A2 | 9/2006 |
| WO | WO2006135400 A2 | 12/2006 |
| WO | WO2007014045 A2 | 2/2007 |
| WO | WO2007086904 A2 | 8/2007 |
| WO | WO2008014002 A2 | 8/2008 |
| WO | WO2008118809 A1 | 10/2008 |

OTHER PUBLICATIONS

Adrian T., et al., "DNA Restriction Analysis of Adenovirus Prototypes 1 to 41," Archives of Virology, 1986, vol. 91 (3-4), pp. 277-290.
Adzhar A., et al., "Universal Oligonucleotides for the Detection of Infectious Bronchitis Virus by Thepolymerase Chain Reaction," Avian Pathology, 1996, vol. 25 (4), pp. 817-836.
Agostini H.T., et al., "Complete Genome of a JC Virus Genotype Type 6 from the Brain of an African American with Pregressive Multifocal Leukoencephalopathy." Journal of Human Virology, 1998, vol. 1 (4), pp. 267-272.
Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.
Akalu A., et al., "Rapid Identification of Subgenera of Human Adenovirus by Serological and PCR Assays," Journal of Virological Methods, 1998, vol. 71 (2), pp. 187-196.
Alba M.M., et al., "VIDA: A Virus Database System for the Organization of Animal Virus Genome Open Reading Frames," Nucleic Acids Research, 2001, vol. 29 (1), pp. 133-136.
Allaouchiche B., et al., "Clinical Impact of Rapid Oxacillin Susceptibility Testing Using a PCR Assay in *Staphylococcus aureus* Bactaeremia," The Journal of Infection, 1999, vol. 39 (3), pp. 198-204.
Allawi H.T., et al., "Thermodynamics and NMR of Internal G.T. Mismatches in DNA," Biochemistry, 1997, vol. 36 (34), pp. 10581-10594.
Altschuel S.F., et al., "Basic Local Alignment Search Tool," Journal of Molecular Biology, 1990, vol. 215 (3), pp. 403-410.
Altschuel S.F., et al., "Gapped BLAST and PSI-BLAST: A New Generation of Protein Database Search Programs," Nucleic Acids Research, 1997, vol. 25 (17), pp. 3389-3402.
Alves-Silva J., et al., "The Ancestry of Brazilian mtDNA Linages," The American Journal of Human Genetics, 2000, vol. 67 (2), pp. 444-461.
Amano Y., et al., "Detection of Influenza Virus: Traditional Approaches and Development of Biosensors," Analytical and Bioanalytical Chemistry, 2005, vol. 381 (1), pp. 156-164.
Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.
Anderson M.L.M., "Quantitative Filter Hybridization" in: Nucleic Acid Hybridization, Hames B.D., ed., IRL Press, 1985, pp. 73-111.
Anderson S., et al., "Sequence and Organization of the Human Mitochondrial Genome," Nature, 1981, vol. 290 (5806), pp. 457-465.
Andreasson H., et al., "Mitochondrial Sequence Analysis for Forensic Identification Using Pyrosequencing Technology," BioTechniques, 2002, vol. 32 (1), pp. 124-133.
Anthony R.M., et al., "Use of the Polymerase Chain Reaction for Rapid Detection of High-Level Mupirocin Resistance in Staphylococci," European Journal of Clinical Microbiology & Infectious Diseases, 1999, vol. 18 (1), pp. 30-34.
Arbique J., et al., "Comparison of the Velogene Rapid MRSA Identification Assay, Denka MRSAScreen Assay, and BBL Crystal MRSA ID System for Rapid Identification of Methicillin-Resistant *Staphylococcus aureus*," Diagnositic Microbiology and Infectious Deseases, 2001, vol. 40 (1-2), pp. 5-10.
Archer G.L., et al., "Detection of Methicillin Resistance in Staphylococci by Using a DNA Probe," Antimicrobial Agents and Chemotherapy, 1990, vol. 34 (9), pp. 1720-1724.
Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.
Arnal C., et al,, "Quantification of Hepatitis A Virus in Shellfish by Competitive Reverse Transcription PCR with Coextraction of Standard RNA," Applied and Environmental Microbiology, 1999, vol. 65 (1), pp. 322-326.
Aronsson F., et al., "Persistence of the Influenza A/WSN/33 Virus RNA at Midbrain Levels of Immunodefective Mice," Journal of Neurovirology, 2001, vol. 7 (2), pp. 117-124.
Ausubel F.M., et al., Eds., Current Protocols in Molecular Biology, vol. 1, John Wiley & Sons Inc., 2004, Table of Contents.
Ausubel P.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.
Ausubel P.M., et al., "Unit 2.11 "Synthesis and Purification of Oligonucleotides," in: Current Protocols in Molecular Biology," 1998, John Wiley & Sons, Inc., pp. 2.11-2.11.21.
Avellon A., et al., "Rapid and Sensitive Diagnosis of Human Adenovirus Infections by a Generic Polymerase Chain Reaction," Journal of Virological Methods, 2001, vol. 92 (2), pp. 113-120.
Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.
Baba T., et al., "Genome and Virulence Determinants of High Virulence Community-Acquired MRSA," Lancet, 2002, vol. 359 (9320), pp. 1819-1827.
Bahrmahd A.R., et al., "Polymerise Chain Reaction of Bacterial Genomes with Single Universal Primer: Application to Distinguishing Mycobacteria Species," Molecular and Cellular Probes, 1996, vol. 10 (2), pp. 117-122.
Bahrmahd A.R., et al., "Use of Restriction Enzyme Analysis of Amplified DNA Coding for the hsp65 Gene and Polymerase Chain Reaction with Universal Primer for Rapid Differtiation of *Mycobacterium* Species in the Clinical Laboratory," Scandinavian Journal of Infectious Diseases, 1998, vol. 30 (5), pp. 477-480.
Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.
Baker G.C., et al., "Review and Re-Analysis of Domain-Specific 16S Primers," Journal of Microbiological Methods, 2003, vol. 55 (3), pp. 541-555.
Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.
Barbour A.G., et al., "Identification of an Uncultivatable *Borrelia* Species in the Hard Tick *Amblyomma americanum*: Possible Agent of a Lyme Disease-Like Illness," The Journal of Infectious Diseases, 1996, vol. 173 (2), pp. 403-409.

(56) References Cited

OTHER PUBLICATIONS

Barns S.M., et al., "Detection of Diverse New *Francisella*-like Bacteria in Environmental Samples," Applied and Environmental Microbiology, 2005, vol. 71 (9), pp. 5494-5500.
Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Suppl. 3), pp. 87-92.
Barr I.G., et al., "An Influenza A(H3) Reassortant was Epidemic in Australia and New Zealand in 2003," Journal of Medical Virology, 2005, vol. 76 (3), pp. 391-397.
Barski P., et al., "Rapid Assay for Detection of Methicillin-Resistant *Staphylococcus aureus* Using Multiplex PCR," Molecular and Cellular Probes, 1996, vol. 10 (6), pp. 471-475.
Bastia T., et al., "Organelle DNA Analysis of Solanum and Brassica Somatic Hybrids by PCR with Universal Primers," Theoretical and Applied Genetics, 2001, vol. 102 (8), pp. 1265-1272.
Batey R.T., et al., "Preparation of Isotopically Labeled Ribonucleotides for Multidimensional NMR Spectroscopy of RNA," Nucleic Acids Research, 1992, vol. 20 (17), pp. 4515-4523.
Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.
Beall B., et al., "Sequencing emm-Specific PCR Products for Routine andAccurate Typing of Group A Streptococci," Journal of Clincal Microbiology, 1996, vol. 34 (4), pp. 953-958.
Beall B., et al., "Survey of emm Gene Sequences and T-Antigen Types from Systemic *Streptococcus pyogenes* Infection Isolates Collected in San Francisco, California; Atlanta, Georgia; and Connecticut in 1994 and 1995," Journal of Clinical Microbiology, 1997, vol. 35 (5), pp. 1231-1235.
Benko, M. et al., "Family Adenoviridae," Virus taxonomy. VIIIth report of the International Committee on Taxonomy of Viruses, 2004, Academic Press, New York, pp. 213-228.
Benson D.A., et al., "GenBank," Nucleic Acids Research, 1999, vol. 27 (1), pp. 12-17.
Benson L.M., et al, "Advantages of *Thermococcus kodakaraenis* (KOD) DNA Polymerase for PCR-Mass Spectrometry Based Analyses," American Society for Mass Spectrometry, 2003, vol. 14 (6), pp. 601-604.
Berencsi G., et al., "Molecular Biological Characterization of Adenovirus DNA," Acta Microbiologica et Immunologica Hungarica, 1998, vol. 45 (3-4), pp. 297-304.
Bishop M.J., et al., "Molecular Sequence Databases" in: Nucleic Acid Protein Sequence Analysis, 4th Chapter, Bishop M.J., et al., Eds, IRL Press, 1987, pp. 83-113.
Bisno A.L., "*Streptococcus pyogenes*" in: Infectious Diseases and Their Etiologic Agents, vol. 2, Mandell, Eds., Churchill Livingston, New York, pp. 1786-1799.
Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Blaiotta G., et al., "PCR Detection of Staphylococcal Enterotoxin Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.
BLAST Search results, Mar. 7, 2006.
Boivin-Jahns V., et al., "Bacterial Diversity in a Deep-Subsurface Clay Environment," Applied and Environmental Microbiology, 1996, vol. 62 (9), pp. 3405-3412.
Bolton E.T., et al., "A General Method for the Isolation of RNA Complementary to DNA," Proceedings of the National Academy of Sciences, 1962, vol. 48, pp. 1390-1397.
Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Boubaker K., et al., "Panton-Valentine Leukocidin and Staphylococcal Skin Infections in Schoolchildren," Emerging Infectious Diseases, 2004, vol. 10 (1), pp. 121-124.
Bowen J.E., et al., "The Native Virulence Plasmid Combination Affects the Segregational Stability of a Thetareplicating Shuttle Vector in *Bacillus anthracis* Var," Journal of Applied Microbiology, 1999, vol. 87 (2), pp. 270-278.
Bowers K.M., et al.. "Screening for Methicillin Resistance in *Staphylococars aureus* and Coagulasenegative Staphylococci: Evaluation of Three Selective and Mastalex-MRSA latex Agglutination," British Journal of Biomedical Science, 2003, vol. 60 (2), pp. 71-74.
Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of *Bacillus anthracis*," Molecular and Cellular Probes, 1998, vol. 12 (6), pp. 367-377.
Brightwell G., et al., "Gentic Targets for the Detection and Identification of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, Vol, 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the *Arabidopsis* Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J.. "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando FL.

(56) References Cited

OTHER PUBLICATIONS

Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing" Forensic Science International, 2000, vol. 110 (2), pp. 79-85.
Carroll K.C., et al., "Rapid Detection of the Staphylococcal mecA Gene from BACTEC BloodCulture Bottles by the Polymerase Chain Reaction," American Journal of Clincal Pathology, 1996, vol. 106 (5), pp. 600-605.
Case J.T., et al., "Maternal Inheritance of Mitochondrial DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction mailed Jan. 6, 2009 for U.S. Appl. No. 10/660,996, filed Sep. 12, 2003.
Certificate of Correction mailed Aug. 7, 2007 for U.S. Appl. No. 10/660,997, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.
Certificate of Correction mailed Mar. 31, 2008 for U.S. Appl. No, 09/891,793, filed Jun. 26, 2001.
Certificate of Correction mailed Mar. 31, 2008 for U.S. Appl. No. 10/156,608, filed May 24, 2002.
Certificate of Correction mailed Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al., "New RNA Polymerase from *Escerichia coli* Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin-Susceptible and -Resistant Isolates of *Staphylococcus aureus* from Nasal Samples," Journal of Clincal Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.
Chen C.H., et al., Laser Desorption Mass Spectrometry for FastDNA Sequencing [online], Nov. 1994, Retrieved from the Internet:<URL:http://www.ornl.gove/sci/techresources/Human_Genome/publicat/94SANTA/sequencing/seqtoc.shtml>.
Chen J., et al., "A Universal PCR Primer to Detect Members of the Potyviridae and its Use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chiu N.H., et al., "Mass Spectrometry of Single-Stranded Restriction Fragments Captured by an Undigested Complementary Sequence," Nucleic Acids Research, 2000, vol. 28 (8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus *Saccharomonospora*," International Journal of Systematic Bacteriology, 1998, vol. 48 (4), pp. 1223-1230.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/209,439, filed Aug. 23, 2005.
Co-pending U.S. Appl. No. 11/674,538, filed Feb. 13, 2007.
Co-pending U.S. Appl. No. 11/682,259, filed Mar. 5, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/639,068, filed Dec. 22, 2004.

(56) References Cited

OTHER PUBLICATIONS

Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319.
Co-pending U.S. Appl. No. 60/443,443, filed Jan. 29, 2003.
Co-pending U.S. Appl. No. 60/443,788.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494.
Co-pending U.S. Appl. No. 60/470,175, filed May 12, 2003.
Co-pending U.S. Appl. No. 60/501,926, filed Sep. 11, 2001.
Co-pending U.S. Appl. No. 60/509,911.
Co-pending U.S. Appl. No. 60/604,329, filed Aug. 24, 2004.
Co-pending U.S. Appl. No. 60/615,387.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479.
Co-pending U.S. Appl. No. 60/941,641.
Cornel A.J., et al., "Polyrnerase Chain Reaction Species Diagnostic Assay for *Anopheles quadrimaculatus* Cryptic Species (Diptera:Culicidae) Based on Ribosomal DNA ITS2 Sequences," Journal of Medical Entomology, 1996, Vol, 33 (1), pp. 109-116.
Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Current Opinion in Biotechnology, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals, Including Two Strains that Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of *Francisella tularensis* Strains," Journal of Clinical Microbiology, 2000, vol. 38 (3), pp. 1016-1022.
Deforce D.L., et al., "Analysis of Oligonucleotides by ESI-MS," Advances in Chromatography, 2000, vol. 40, pp. 539-566.
Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.
Del Blanco Garcia N., et al., "Genotyping of *Francisella tularensis* Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.
Denis M., et al., "Development of a Semiquantitative PCR Assay Using Internal Standard and Colorimetricdetection on Microweli Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.
Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 3 (1), pp. 71-81.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-Based Typing of HLA Class II DQB1," Tissue Antigens, 2000, vol. 55 (4), pp. 364-368.
Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 1992, vol. 1 (4), pp. 263-268.
Doty P., et al., "Strand Separation and Specific Recombination in Deoxyribonucleic Acids: Physical Chemical Studies," Proceedings of the National Academy of Sciences, 1960, vol. 46 (4), pp. 461-476.
Drosten C., et al., "Identification of a Novel Coronavirus in Patients with Severe Acute Respiratory Syndrome," New England Journal of Medicine, 2003, vol. 348 (20), pp. 1967-1976.
Dubernet S., et al., "A PCR-Based Method for Identification of Lactobacilli at to Genus Level," FEMS Microbiology Letters, 2002, vol. 214 (2), pp. 271-275.
Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSampies by PCR During an AdV-Associated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.

(56) References Cited

OTHER PUBLICATIONS

Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Edwards K.M., et al., "Adenovirus Infections in Young Children," Pediatrics, 1985, vol. 76 (3), pp. 420-424.
Ellis J.S., et al., "Molecular Diagnosis of Influenza," Reviews in Medical Virology, 2002, vol. 12 (6), pp. 375-389.
Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.
Elnifro E.M., et al., "PCR and Restriction Endonuclease Analysis for Rapid Identification of Adenovirus Subgenera," Journal of Clinical Microbiology, 2000, vol. 38 (6), pp. 2055-2061.
Elsayed S., et al., "Development and Validation of a Molecular Beacon Probe-Based Real-Time Polymerase Chain Reaction Assay for Rapid Detecion of Methicillin Resistance in *Staphylococcus aureus*," Archives of Pathology and Laboratory Medicine, 2003, vol. 127 (7), pp. 845-849.
EMBL, "*Arabidopsis thaliana* T-DNA Flanking Sequence, Left Border, Clone 346C06," Accession No. AJ552897, Mar. 29, 2003.
EMBL "Dog (Clone: CXX.147) Primer for STS 147, 3" End, Sequence Tagged Site," Accession No. L15697, Mar. 4, 2000.
EMBL "Human, muscle, Mitochondrial Mutant, 22 nt, segment 2 of 2," Accession No. S90302, Sep. 1, 2004.
EMBL "Sequence 10 from Patent US 6563025," Accession No. AR321656, Aug. 18, 2003.
EMBL "Synthetic Construct DNA, Reverse Primer for Human STS sts-AA031654 at 1p36" Accession No. AB068711, May 21, 2003.
Enright M.C., et al., "A Multilocus Sequence Typing Scheme for *Streptococcus pneumoniae*: Identification of Clones Associated with Serious Invasive Disease," Microbiology, 1998, vol. 144 (Pt 11), pp. 3049-3060.
Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38 (3), pp. 1008-1015.
Enright M.C., et al., "Multilocus Sequence Typing of *Streptococcus pyogenes* and theRelationships between Emm Type and Clone," Infection and Immunity, 2001, vol. 69 (4), pp. 2416-2427.
Enright M.C., et al., "The Evolutionary History of Methicillin-Resistant *Staphylococcus aureus* (MRSA)," Proceedings of the National Academy of Sciences, 2002, vol. 99 (11), pp. 7687-7692.
Enright M.C., "The Evolution of a Resistant Pathogen—the Case of MRSA," Current Opinion in Pharmacology, 2003, vol. 3 (5), pp. 474-479.
Eremeeva M.E., et al., "Evaluation of a PCR Assay for Quantitation of *Rickettsia rickettsii* and Closely Related Spotted Fever Group Rickettsiae," Journal of Clinical Microbiology, 2003, vol. 41 (12), pp. 5466-5472.

Erlich H.A., Ed., PCR Technology: Principles and Applications for DNA Amplification, W.H. Freeman and Company, 1989.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
European Search Report for Application No. EP10175659.1, mailed on Feb. 9, 2011, 4 pages.
Evans P., et al., "Practical Algorithms for Universal DNA Primer Design: An Exercise in Algorithm Engineering," Currents in Computational Molecular Biology, 2001, pp. 25-26.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Jun. 7, 2011 for U.S. Appl. No. 11/930,108, filed Oct. 31, 2007.
Examiner Interview Summary mailed Aug. 10, 2004 for U.S. Appl. No. 09/798,007, filed Mar. 2, 2001.
Examiner Interview Summary mailed Aug. 10, 2004 for U.S. Appl. No. 09/891,793, filed Jun. 26, 2001.
Examiner Interview Summary mailed Aug. 10, 2004 for U.S. Appl. No. 10/156,608, filed May 24, 2002.
Examiner Interview Summary mailed Aug. 10, 2004 for U.S. Appl. No. 10/326,642, filed Dec. 18, 2002.
Examiner Interview Summary mailed May 19, 2003 for U.S. Appl. No. 09/891,793, filed Jun. 26, 2001.
Examiner Interview Summary mailed Oct. 24, 2008 for U.S. Appl. No. 11/582,859, filed Oct. 17, 2006.
Examiner Interview Summary mailed Feb. 27, 2006 for U.S. Appl. No. 10/326,644, filed Dec. 18, 2002.
Examiner Interview Summary mailed Jan. 27, 2006 for U.S. Appl. No. 10/323,211, filed Dec. 18, 2002.
Examiner Interview Summary mailed May 28, 2008 for U.S. Appl. No. 10/660,998, filed Sep. 12, 2003.
Examiner Interview Summary mailed Oct. 28, 2008 for U.S. Appl. No, 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Oct. 29, 2009 for U.S. Appl. No. 10/660,122, filed Sep. 11, 2003.
Examiner Interview Summary mailed Jul. 31, 2006 for U.S. Appl. No. 10/326,643, filed Dec. 18, 2002.
Extended European Search Opinion for Application No. EP10175659.1, mailed on Feb. 21, 2011, 5 pages.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Facklam R., et al., "Emm Typing and Validation of Provisional M Types for Group A Streptococci," Emerging Infectious Diseases, 1999, vol. 5 (2), pp. 247-253.
Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.
Farlow J., et al., "*Francisella tularensis* Strain Typing Using Multiple-Locus, Variable-Number Tandem Repeat Analysis," Journal of Critical Microbiology, 2001, vol. 39 (9), pp. 3186-3192.
Farrell D.J., "The Reliability of Microscan Conventional and Rapid Panels to Identify *Staphylococcus aures* and Detect Methicillin

(56) References Cited

OTHER PUBLICATIONS

Resistance: An Evaluation Using the Tube Coagulase Test and mecA PCR," Pathology, 1997, vol. 29 (4), pp. 406-410.
Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.
Fedele C.G., et al., "Quantitation of Polyomavirus DNA by a Competitive Nested Polymerase Chain Reaction," Journal of Virological Methods, 2000, vol. 88 (1), pp. 51-61.
Feng P., "Impact of Molecular Biology on the Detection of Food Pathogens," Molecular Biotechnology, 1997, vol. 7 (3), pp. 267-278.
Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Apr. 14, 2011 for U.S. Appl. No. 12/049,949, filed Mar. 17, 2008.
Final Office Action mailed Jun. 14, 2011 for U.S. Appl. No. 12/616,422, filed Nov. 11, 2009.
Final Office Action mailed Oct. 14, 2009 for U.S. Appl. No. 10/943,344, filed Sep. 17, 2004.
Final Office Action mailed Nov. 17, 2009 for U.S. Appl. No. 11/582,875, filed Oct. 17, 2006.
Final Office Action mailed Feb. 18, 2010 for U.S. Appl. No. 10/754,415, filed Jan. 9, 2004.
Final Office Action mailed Nov. 20, 2009 for U.S. Appl. No. 11/331,987, filed Jan. 13, 2006.
Final Office Action mailed Jun. 23, 2010 for U.S. Appl. No. 11/930,017, filed Oct. 30, 2007.
Final Office Action mailed Feb. 26, 2009 for U.S. Appl. No. 11/582,863, filed Oct. 17, 2006.
Final Office Action mailed Jan. 30, 2009 for U.S. Appl. No. 10/844,938, filed May 12, 2004.
Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.
Fong W.K., et al., "Rapid Solid-Phase Immunoassay for Detection of Methicillin Resistant*Staphylococcus aureus* Using Cycling Probe Technology," Journal of Clinical Microbiology, 2000, vol. 38 (7), pp. 2525-2529.
Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.
Fox A., et al., "Report of the Bioterrorism Workshop," Journal of Microbiological Methods, 2002, vol. 51 (3), pp. 247-254.
Fox J.P., et al., "The Virus Watch Program: A Continuing Surveillance of Viral Infections in Metropolitan New York Families," American Journal of Epidemiology, 1969, vol. 89 (1), pp. 25-50.
Fox K.F., et al., "Identification of *Brucella* by Ribosomal-Spacer-Region PCR and Differentiation of *Brucell canis* from Other *Brucella* Spp. Pathogenic for Humans by Carbohydrate Profiles," Journal of Clinical Microbiology, 1998, vol. 36 (11), pp. 3217-3222.
Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.
Francois P., et al., "Rapid Detection of Methicillin-Resistant *Staphylococcus Aureus* Directly from Sterile or Nonsterile Clinical Samples by a New Molecular Assay," Journal of Clinical Microbiology, 2003, vol. 41 (1), pp. 254-260.
Fraser C.M., et al., "The Mimimal Gene Complement of *Mycoplasma genitalium*," Science, 1995, vol. 270 (5235), pp. 397-403.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.
Fujimura S., et al., "Isoleucyl-tRNA Synthetase Mutations in *Staphylococcus aureus* ClinicalIsolates and In Vitro Selection of Low-Level Mupirocin-Resistant Strains," Antimicrobial Agents and Chemotheraphy, 2003, vol. 47 (10), pp. 3373-3374.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gall J.G., et al., "Construction and Characterization of Hexon-Chimeric Adenoviruses: Specification of Adenovirus Serotype," Journal of Virology, 1998, vol. 72 (12), pp. 10260-10264.
Gammelin M., et al., "Two Subtypes of Nucleoproteins (NP) of Influenza A Viruses," Virology, 1989, vol. 170 (1), pp, 71-80.
Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Gaydos C.A., et al., "Adenovirus Vaccines in the U.S. Military," Military Medicine, 1995, vol. 160 (6), pp. 300-304.
Geha D.J., et al., "Multiplex PCR for Identification of Methicillin-Resistant Staphylococci in the Clinical Laboratory," Journal of Clinical Microbiology, 1994, vol. 32 (7), pp. 1768-1772.
GenBank, "{Deletion 6} [Human, Muscle, Mitochondrial Mutant, 22 nt, Segment 2 of 2]," Accession No. S90302.1, Jun. 10, 1992.
GenBank, "Acinetobacter Genomosp. 10 Strain CIP 70.12 RNA Polymerase Subunit B (rpoB) Gene, Complete Cds," Accession No. 78099429, Mar. 11, 2006.
GenBank, "Bovine Parainfluenza Virus 3 Strain Shipping Fever, Complete Genome," Accesion No. AF178655, Sep. 19, 2000.
GenBank, "*Clostridium tetani* E88, Complete Genome," Accession No. AE015927.1, Feb. 4, 2003.
GenBank, "*E. coli* Operon rpoBC Coding for the Beta- and Beta"-Subunits of RNA Polymerase (Genes rpoC and rpoB), and Genes rplL, rlpJ, rplA, and rplK Coding for 50S Ribosomal Subunit Proteins

(56) References Cited

OTHER PUBLICATIONS

L7/L12, L10, L1, and L11, Respectively. (Map position 89-90 min.)," Accession No. 42813, Feb. 28, 1992.

GenBank, "*E. coli* 16S Ribosomal RNA," Accession No. 174375, Aug. 11, 1995.

GenBank, "*E. coli* Open Reading Frame Upstream of Leu Operon," Accession No. M21150, Sep. 15, 1990.

GenBank, "*E.coli* rRNA Operon (rrnB) Coding for Glu-tRNA-2, 5S, 16S and 23S rRNA," Accession No. 147581, Sep. 14, 1992.

GenBank, "*Enterococcus malodoratus* Strain ATCC43197 Elongation Factor Tu (tufA) Gene, Partial Cds," Accession No. AF274728, Dec. 11, 2000.

GenBank "*Escherichia coli* str. K-12 substr. MG1655, Complete Genome," Accession No. NC000913, Oct. 15, 2001.

GenBank, "*Homo sapiens* Haplotype V Mitochondrion, Complete Genome", Accession No. AF381990.1, Dec. 28, 2001.

GenBank, "Human Adenovirus Type 4 Hexon Gene," for Accession No. X84646, Jun. 30, 1995.

Genbank, "Human Coronavirus 229E, Complete Genome," Accession No. AF304460, Jul. 11, 2001.

GenBank, "Human Isolate L34 Mitochondrion D-loop Region", Accession No. U08081.1, Aug. 16, 1994.

GenBank, "il11b08.y1 Human insulinoma *Homo sapiens* cDNA clone Image:6029534 5—similar to SW:COX3_Human P00414 Cytochrome C Oxidase Polypeptide III ;, mRNA sequence", Accession No. BQ581956.1, Jun. 20, 2002.

GenBank, "Influenza B Virus B/Panama/45/90 Polymerase (PB2) mRNA, Complete Cds", Accession No. AF005737, Oct. 4, 1997, pp. 1-3.

GenBank, "Mastadenovirus h7 Hexon Gene," Accession No. Z48571, Apr. 18, 2005.

GenBank, "or72a01.s1 NCI_CGAP_Lu5 *Homo sapiens* cDNA Clone Image:1601352 3—similar to SW:COX1_Human P00395 Cytochrome C Oxidase Polypeptide I ;, mRNA sequence", Accession No. AI002209.1, Jun. 10, 1998.

GenBank "*Staphylococcus aureus* RN4220 ErmC Gene, Partial Cds," Accession No. 18542231, Sep. 16, 2003.

GenBank "*Staphylococcus aureus* Strain MSSA476, Complete Genome," Accession No. BX571857.1, Jun. 24, 2004.

Genbank, "*Staphylococcus aureus* Subsp. *Aureus* Mu50, Complete Genome," Accession No. 15922990, Oct. 4, 2001.

Genbank "*Staphylococcus aureus* Subsp. *Aureus* MW2, Complete Genome," Accession No. 6121281729, May 31, 2002

GenBank, "*Staphylococcus epidermidis* ATCC 12228, Complete Genome," Accession No. AE015929,1, Jan. 2, 2003.

GenBank "*Streptococcus agalactiae* 2603V/R, Complete Genome," Accession No. AE009948.1, Aug. 28, 2002.

GenBank, "*Streptococcus anginosus* Elongation Factor Tu (tuf) Gene, Partial cds," Accession No. AF276257.1, Jul. 1, 2001.

GenBank, "*Streptococcus pneumoniae* Isolate 95.1In00S DNA Gyrase Subunit B (gyrB) Gene, Complete Cds," Accession No. 73916349, Sep. 30, 2005.

GenBank, "*Streptococcus pyogenes* Strain MGAS8232, Complete Genome," Accession No. AE009949.1, Apr. 3, 2002.

GenBank, "Venezuelan Equine Encephalitis Virus Nonstructural Polyprotein and Structural Polyprotein Genes, Complete Cds," Accession No. AF375051.1, Jun. 26, 2001.

Gendel S.M., "Computational Analysis of the Specificity of 16S rRNA-Derived Signature Sequencesfor Identifying Food-Related Microbes," Food Microbiology, 1996, vol. 13, pp. 1-15.

Gibb T.R., et al., "Development and Evaluation of a 5" Fluorogenic Nuclease Assay to Detect and Differentiate Between Ebola Virus Subtypes Zaire and Sudan," Journal of Clinical Microbiology, 2001, vol. 39 (11), pp. 4125-4130.

Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.

Giles R.E., et al., "Maternal Inheritance of Human Mitochondrial DNA," Proceedings of the National Academy of Sciences, 1980, vol. 77 (11), pp. 6715-6719.

Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," Journal of Bacteriology, 2005, vol. 187 (7), pp. 2426-2438.

Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.

Ginther C., et al,, "Identifying Individuals by Sequencing Mitochondrial DNA from Teeth," Nature Genetics, 1992, vol. 2 (2), pp. 135-138.

Gjoen K.V., et al., "Specific Detection of Coxsackie Viruses A by the Polymerase Chain Reaction," Clinical and Diagnostic Virology, 1997, vol. 8 (3), pp. 183-188.

Golden M.R., et al., "Pilot Study of COBAS PCR and Ligase Chain Reaction for Detection of Rectal Infections Due to *Chlamydia trachomatis*," Journal of Clinical Microbiology, 2003, vol. 41 (5), pp. 2174-2175.

Goto K., et al., "Applications of the Partial 16S rDNA Sequence as an Index for Rapid Identification of Species in the Genus *Bacillus*," Journal of General and Applied Microbiology, 2000, vol. 46 (1), pp, 1-8.

Gravet A., et al., "Characterization of a Novel Structural Member, LukE-LukD, of the Bi-Component Staphylococcal Leucotoxins Family," FEBS Letters, 1998, vol. 436 (2), pp. 202-208.

Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.

Greenberg B.D., et al., "Intraspecific Nucleotide Sequence Variability Surrounding the Origin of Replicationin Human Mitochondrial DNA," Gene, 1983, vol. 21, pp. 33-49.

Griffey, et al., "Detection of Base Pair Mismatches in Duplex DNA and RNA Oligonucleotides Using Electrospray Mass Spectrometry," SPIE, 1997, vol. 2985, pp. 82-86.

Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.

Griffin T.J., et al., "Single-Nucleotide Polymorphism Analysis by Maldi-TOF Mass Spectrometry," Trends in Biotechnology, 2000, vol. 18 (2), pp. 77-84.

Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.

Grundmann H., et al., "Emergence and Resurgence of Meticillin-Resistant *Staphylococcus aureus* as a Public-Health Threat," Lancet, 2006, vol. 368 (9538), pp. 874-885.

Grzybowski T., et al., "Extremely High Levels of Human Mitochondrial DNA Heteroplasmy in Single Hair Roots," Electrophoresis, 2000, vol. 21 (3), pp. 548-553.

Gu Z., et al., "Multiplexed, Real-Time PCR for Quantitative Detection of Human Adenovirus," Journal of Clinical Microbiology, 2003, vol. 41 (10), pp. 4636-4641.

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Haines J.D., et al., "Medical Response to Bioterrorism: Are We Prepared," Journal of Oklahoma State Medical Association, 2000, vol. 93, pp. 187-196.

Hall T.A., et al., "Base Composition Analysis of Human Mitochondrial DNA Using Electrospray Ionization Mass Spectrom-

(56) References Cited

OTHER PUBLICATIONS etry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.

Hamel S., et al., "Consensus PCR and Microarray for Diagnosis of the Genus *Staphylococcus,* Species, and Methicillin Resistance," Biotechnigues, 2001, vol. 31 (6), pp. 1364-1372.

Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Altomole Level Electrosprayed from Low Nanomolar Solutions using FT-ICR Mass Spectrometry," Fresenius Journal of Analytical Chemistry, 2001, vol. 369 (3-4), pp. 246-251.

Hannis J,C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Hanssen A.M., et al., "Sccmecin Staphylococci: Genes on the Move," FEMS Immuol Medical Microbiol, 2006, vol. 46, pp. 8-20.

Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.

Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.

Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.

Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.

He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.

Heim A., et al., "Rapid and Quantitative Detection of Human Adenovirus DNA by Real-Time PCR," Journal of Medical Virology, 2003, vol. 70, pp. 228-239.

Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.

Herrmann B., et al., "Differentiation of *Chiamydia* spp, by Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., et al., "Sensitive and Rapid Identification of Biological Threat Agents," Annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant Staphylococcusaureus," Trends Microbiology, 2001, vol. 9 (10), pp. 486-493.

Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.

Hoffman E., et al., "Rescue of Influenza B Virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza A Viruses," Archives of Virology, 2001, vol. 146 (12), pp. 2275-2289.

Hofstadler S.A., et al., "TIGER: The Universal Biosensor," International Journal of Mass Spectrometry, 2005, vol. 242, pp. 23-41.

Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.

Holland M.M., et al., "Mitochondrial DNA Sequence Analsysis—Validation and Use for Forensic Casework," Forensic Science Review, 1999, vol. 11 (1), pp. 22-50.

Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.

Holm L., et al., "Removing Near-Neighbour Redundancy from Large Protein Sequence Collections," Bioinformatics, 1998, vol. 14 (5), pp. 423-429.

Holmes E.C., et al., "Whole-Genome Analysis of Human Influenza A Virus Reveals Multiple Persistent Lineages and Reassortrnent among Recent H3N2 Viruses," Public Library of Science Biology, 2005, vol. 3 (9), pp. 1579-1589.

Honda K., et al., "Universal Method of Hypersensitive Nested PCR Toward Forensic DNA typing," International Congress Series, 1998, vol. 7, pp. 28-30.

Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.

Hood E., et al., "Chemical and Biological Weapons: New Questions, New Answers," Environmental Health Perspectives, 1999, vol. 107 (12), pp. 931-932.

Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.

Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.

Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.

Huletsky A., et al., "New Real-Time Pcr Assay for Rapid Detection of Methicillin-Resistant *Staphylococcus aureus* Directly from Specimens Containing a Mixture of Staphylococci," Journal of Clinical Microbiology, 2004, vol. 42 (5), pp. 1875-1884.

Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.

(56) References Cited

OTHER PUBLICATIONS

Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108-2109.
Hurdle J.G., et al., "Analysis of Mupirocin Resistance and Fitness in *Staphylococcus aureus* by Molecular Genetic and Structural Modeling Techniques," Antmicrobial Agents and Chemotherapy, 2004, vol. 48 (11), pp. 4366-4376.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.
Ieven M., et al., "Rapid Detection of Methicillin Resistance in Coagulase-Negative Staphylococci by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, 1996, vol. 28 (3), pp. 259-261.
Ingman M., et al., "Mitochondrial Genome Variation and the Origin of Modern Humans," Nature, 2000, vol. 408 (6813), pp. 708-713.
International Preliminary Examination Report for Application No. PCT/US2002/06763, mailed on Jun. 11, 2003, 6 pages.
International Preliminary Examination Report for Application No. PCT/US2002/20336, mailed on Apr. 26, 2004, 8 pages.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages
International Preliminary Examination Report for Application No. PCT/US2003/38757, mailed on Feb. 2, 2007, 5 pages.
International Preliminary Examination Report for Application No. PCT/US2003/38761,mailed on Jun. 27, 2006, 6 pages.
"International Preliminary Report on Patentability and Written Opinion for Application No. PCT/US04/007236, mailed on Mar. 16, 2006, 7 pages."
International Preliminary Report on Patentability and Written Opinion for Application No. PCT/US2005/00386, mailed on Jul. 10, 2006, 6 pages.
International Preliminary Report on Patentability and Written Opinion for Application No. PCT/US2005/030058, mailed on Sep. 25, 2007, 6 pages.
International Preliminary Report on Patentability and Written Opinion for Application No. PCT/US2005/033707, mailed on Mar. 20, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Preliminary Report on Patentabilty for Appplication No. PCT/US2005/018031, mailed on Nov. 29, 2006, 1 page.
International Search Report and Written Opinion for Application No. PCT/US2005/018031, mailed on Jun. 28, 2006, 14 pages.
International Search Report and Written Opinion for Application No. PCT/US2006/007747, mailed on Sep. 5, 2006, 13 pages.
International Search Report and Written Opinion for Application No. PCT/US2006/028397. mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed Jan. 9, 2008, 21 pages.
International Search Report and Written Opinion for Application No. PCT/US2007/020045 mailed on Jan. 8, 2009, 17 pages.
International Search Report and Written Opinion for Application No. PCT/US2008/054926, mailed on Jan. 26, 2009, 15 pages.
International Search Report and Written Opinion for Application No. PCT/US2008/057901, mailed on Aug. 28, 2008, 14 pages.
International Search Report and Written Opinion for Application No. PCT/US2008/064891, mailed on Jun. 29, 2009, 15 pages.
International Search Report for Application No. PCT/US04/007236, mailed on Feb. 24, 2006, 2 pages.
International Search Report for Application No. PCT/US2002/06763, mailed on Oct. 23, 2002, 2 pages.
International Search Report for Application No. PCT/US2002/20336, mailed on Feb. 3, 2003, 4 pages.
International Search Report for Application No. PCT/US2003/009802, mailed on Aug. 3, 2004, 2 pages.
International Search Report for Application No. PCT/US2003/038505, mailed on Apr. 12, 2005, 2 pages.
International Search Report for Application No. PCT/US2003/038830, mailed on Aug. 25, 2004, 4 pages.
International Search Report for Application No. PCT/US2003/22835, mailed on Dec. 12, 2003, 1 page.
International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.
International Search Report for Application No. PCT/US2005/006133, mailed on Jul. 26, 2007, 4 pages.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 4 pages.
International Search Report for Application No. PCT/US2008/065332, mailed on Nov. 28, 2008, 4 pages.
International Search Report for Application No. PCT/US2009/045635, mailed on Oct. 7, 2009, 9 pages.
Inyaku K., et al., "Rapid Detection and Identification of Mycobacteria in Sputum Samples by Nested Polymerase Chain Reac-

(56) References Cited

OTHER PUBLICATIONS tion and Restriction Fragment Length Polymorphisms of dnaJ Heat Shock Protein Gene," Journal of Medical Sciences, 1993, vol. 42 (1), pp. 21-31.

Iqbal S.S., et al., "A Review of Molecular Recognition Technologies for Detection of Biological Threat Agents," Biosensors & Bioelectronics, 2000, vol. 15 (11-12), pp. 549-578.

Isola N.R., et al., "MALDI-TOF Mass Spectrometric Method for Detection of Hybridized DNA Oligomers," Analytical Chemistry, 2001, vol. 73 (9), pp. 2126-2131.

Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.

Ito T., et al., "Insights on Antibiotic Resistance of *Staphylococcus aureus* from its Whole Genome: Genomic Island Scc," Drug Resistance Updates, 2003, vol. 6 (1), pp. 41-52.

Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.

Jackson P.E., et al., "Mass Spectrometry for Genotyping: an Emerging Tool for Molecular Medicine," Molecular Medicine Today, 2000, vol. 6 (7), pp. 271-276.

James A.M., et al., "*Borelia lonestari* Infection after a Bite by an *Amblyomma americanum* Tick," The Journal of Infectious Diseases, 2001, vol. 183 (12), pp. 1810-1814.

Jankowski K., et al., "Mass Spectrometry of DNA. Part 2 Quantitative Estimation of Base Composition," European Journal of Mass Spectrometry, 1980, vol. 1 (1), pp. 45-52.

Jansen R.C., et al., "Genotype-by-environment Interaction in Genetic Mapping of Multiple Quantitative Trait Loci," Theoretical and Applied Genetics, 1995, vol. 91, pp. 33-37.

Jaulhac B., et al., "Specific Detection of the Toxic Shock Syndrome Toxin-1 Gene Using the Polymerase Chain Reaction," Molecular and Cellular Probes, 1991, vol. 5, pp. 281-284.

Jaulhac B., et al., "Synthetic DNA Probes for Detection of Genes for Enterotoxins A, B, C, D, E and for Tsst-1 In Staphylococcal Strains," Journal of Applied Bacterial, 1992, vol. 72 (5), pp. 386-392.

Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.

Jeong J., et al., "Early Screening of Oxacillin-Resistant *Staphylococcus aureus* and *Staphylococcus epidermidis* from Blood Culture," Journal of Korean Medical Science, 2002, vol. 17, pp. 168-172.

Jiang C., et al., "Multiple Trait Analysis of Genetic Mapping for Quantitative Trait Loci Genetics," Genetics, 1995, vol. 140 (3), pp. 1111-1127.

Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.

Johansson A., et al., "Evaluation of PCR-based Methods for Discrimination of *Francisella* species and Subspecies and Development of a Specific PCR that Distinguishes the Two Major Subspecies of *Francisella tularensis*," Journal of Clinical Microbiology, 2000, vol. 38 (11), pp. 4180-4185.

Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.

Johnson Y.A., et al., "Precise Molecular Weight Determination of PCR Products of the rRNA Intergenic Spacer Region Using Electrospray Quadrupole Mass Spectrometry for Differentiation of *B. subtilis* and *B. atrophaeus*, Closely Related Species of Bacilli," Journal of Microbiological Methods, 2000, vol. 40 (3), pp. 241-254.

Jonas D., et al., "Rapid PCR-Based Identification of Methicillin-Resistant *Staphylococcus aureus* from Screening Swabs," Journal of Clinical Microbiology, 2002, vol. 40 (5), pp. 1821-1823.

Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.

Jurinke C., et al., "Detection of Hepatitis B: Virus DNA In Serum Samples Via Nested PCR and MALDI-TOF Mass Spectrometry," Genetic Analysis: Biomolecular Engineering, 1996, vol. 13 (3), pp. 67-71.

Jurinke C., et al., "MALDI-TOF Mass Spectrometry. A Versatile Tool for High-Performance DNA Analysis," Molecular Biotechnology, 2004, vol. 26 (2), pp. 147-163.

Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.

Kageyama A., et al.,, "Rapid Detection of Human Fecal *Eubacterium* Species and Related Genera by Tested PCR Method," Journal of Microbiology, Immunology, 2001, vol. 45 (4), pp. 315-318.

Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.

Kasai H., et al., "Construction of the gyrB Database for the Identification and Classification of Bacteria," Genome Informatics. Workshop on Genome Informatics, 1998, pp. 13-21.

Katano H., et al., "Identification of Adeno-Associated Virus Contamination in Cell and Virus Stocks by PCR," Biotechniques, 2004, vol. 36 (4), pp. 676-680.

Katayama Y., et al., "Genetic Organization of the Chromosome Region Surrounding mecA inClinical Staphylococcal Strains: Role of IS431-Mediated mecl Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant Staphlococci by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Khan A.S., et al., "An Outbreak of Crimean-Congo Haemorrhagic Fever in the United Arab Emirates, 1994-1995," The American Journal of Tropical Medicine and Hygiene,1997, vol. 57 (5), pp. 519-525.

Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.

Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp, 1714-1720.

(56) References Cited

OTHER PUBLICATIONS

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.

Kitagawa Y., et al., "Rapid Diagnosis of Methicillin-Resistant Staphylococcus aureus Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as an Augmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNA in Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of Staphylococcus aureus and Staphylococcus epidermidis: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in Staphylococcus aureus isolates Using Conventional and Molecular Methods: A Descriptive Study from a Burns Unit with High prevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant Staphylococcus aureus," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "Staphylococcus aureus Panton Valentine Leukocidin Causes Necrotizing Pneumonia," ScienceExpress, 2007, 8 pages.

Lacroix J.M,, et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine Encephalitis Viruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Add Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from Escherichia coli," European Journal of Biochemistry, 1995, vol. 230 (2), pp. 538-548.

Lengyel A., et al., "Characterization of the Main Protein Components of Adenovirus Virion and its Possible Use in Laboratory Diagnostics," Acta Microbiologica Immunologica Hungarica, 1998, vol. 43 (3-4), pp. 281-283.

Leroy E.M., et al., "Diagnosis of Ebola Haemorrhagic Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant Staphylococcus aureus from Patient-Screening Swabs," Journal of Clinical Microbiology, 2003, vol. 41 (7), pp. 3187-3191.

Levine S.M., et al., "PCR-Based Detection of Bacillus anthracis in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li C., et al., "Evolution of H9N2 Influenza Viruses from Domestic Poultry in Mainland China" Virology, 2005, vol. 340 (1), pp. 70-83.

(56) References Cited

OTHER PUBLICATIONS

Li J., et al., "Single Nucleotide Polymorphism Determination Using Primer Extension and Time-of-Flight Mass Spectrometry," Electrophoresis, 1999, vol. 20 (6), pp. 1258-1265.
Li Q., et al., "Genetic Variability of Hexon Loops 1 and 2 between Seven Genome Types of Adenovirus Serotype 7," Archives of Virology, 1999, vol. 144 (9), pp. 1739-1749.
Li Q., et al., "Screening of the High Yield Influenza B Virus on MDCK c14d Cloning of its Whole Genome," International Congress Series, 2004, vol. 1263, pp. 610-614.
Li Q.G , et al., "Analysis of 15 Different Genome Types of Adenovirus Type 7 Isolated on FiveContinents," Journal of Virology, 1986, vol. 60 (1), pp. 331-335.
Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.
Liebermann H., et al., "Mapping of Epitopes on the Fiber Knobs of Human Adenovirus Serotypes 8 and 15," Intervirology, 2002, vol. 45 (1), pp. 59-66.
Liebermann H., et al., "Mapping of Linear Epitopes on Fibre Knob of Human Adenovirus Serotype 5," Virus Research, 2001, vol. 73 (2), pp. 145-151.
Lim L.P., et al., "The MicroRNAs of *Caenorhabditis elegans*," Genes and Development, 2003, vol. 17 (8), pp. 991-1008.
Limbach P.A., et al., "Enzymatic Sequencing of Oligonucleotides with Electrospray Mass Spectrometry," 42nd ASMS Conference on Mass Spectrometry, 1994.
Limoncu M.H., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.
Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.
Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.
Lina G., et al., "Bacterial Competition for Human Nasal Cavity Colonization: Role of Staphylococcalagr Alleles," Applied and Environmental Microbiology, 2003, vol. 69 (1), pp. 18-23.
Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.
Linssen B., et al., "Development of Reverse Transcription-PCR Assays Specific for Detection of Equine Encephalitis Viruses," Journal of Clinical Microbiology, 2000, vol. 38 (4), pp. 1527-1535.
Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.
Little D.P., et al, "Rapid Sequencing of Oligonucleotides by High-Resolution Mass Spectrometry," Journal of the American Chemical Society, 1994, vol. 116 (11), pp. 4893-4897.
Liu C., et al., "Improving the Microdialysis Procedure for Electrospray Ionization Mass Spectrometry of Biological Samples," Journal of Mass Spectrometry, 1997, vol. 32 (4), pp. 425-431.
Liu J.H., et al., "Interregional Transmission of the Internal Protein Genes of H2 Influenza Virus in Migratory Ducks from North America to Eurasia," Virus Genes, 2004, vol. 29 (1), pp. 81-86.
Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.
Livermore D.M., "The Threat from the Pink Corner," Annals of Medicine, 2003, vol. 35 (4), pp. 226-234.
Loakes D., et al., "Nitroindoles as Universal Bases," Nucleosides and Nucleotides, 1995, vol. 14 (3-5), pp. 1001-1003.
Loo J.A., et al., "Applying Charge Discrimination with Electrospray Ionization-Mass Spectrometry to Protein Analysis," Journal of American Society for Mass Spectrometry, 1995, vol. 6, pp. 1098-1104.
Lott T.J., et al., "Nucleotide Sequence Analysis of the 5-8s RDNA and Adjacent ITS2 Region of Candidaalbicans and Related Species," Yeast, 1993, vol. 9, pp. 1199-1206.
Louie L., et al., "Evaluation of Three Rapid Methods for Detection of Methicillin Resistance in *Staphylococcus aureus*," Journal of Clinical Microbiology, 2000, vol. 38 (6), pp. 2170-2173.
Love B.C., et al., "Cloning and Sequence of the GroESL Heat-Shock Operon of *Pasteurella multocida*," Gene, 1995, vol. 166 (1), pp. 179-180.
Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.
Lowe T., et al., "A Computer Program for Selection of Oligonucleotide Primers for Poymerase Chain Reactions," Nucleic Acids Research, 1990, vol.18 (7), pp. 1757-1761.
Lu X., et al., "Molecular Typing of Human Adenoviruses by PCR and Sequencing of a Partial Region of the Hexon Gene," Archives of Virology, 2006, vol. 151 (8), pp. 1587-1602.
Lubman D.M., Application for Continuation Grant by David Mitchell Lubman dated Jun. 4, 1996 and Jun. 14, 1996.
Lubman D.M., Application for Continuation Grant by David Mitchell Lubman dated Jun. 10, 1994 and Jun. 24, 1994.
Lubman D.M., Application for Grant by David Mitchell Lubman dated Sep. 1, 1994 and Sep. 27, 1994.
Lubman D.M., Application for Grant by David Mitchell Lubman dated Oct. 25, 1992 and Oct. 29, 1992.
Ludwig S.L., et al., "Prevalence of Antibodies to Adenovirus Serotypes 4 and 7 among Unimmunized US Army Trainees; Results of a Retrospective Nationwide Seroprevalence Survey," The Journal of Infectious Diseases, 1998, vol. 178 (6), pp. 1776-1778.
Ludwig W., et al., "Bacterial Phylogeny Based on 16S and 23S rRNA Sequence Analysis," FEMS Microbiolofy Reviews, 1994, vol. 15 (2-3), pp. 155-173.
Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.
Ma X.X., et al., "Novel Type of Staphylococcal Cassette Chromosome Mec Identified in Community-Acquired Methicillin-Resistant *Staphylococcus aureus* Strains," Antimicrobial Agents and Chemotherapy, 2002, vol. 46 (4), pp. 1147-1152.
Mack D.H., et al., "A Sensitive Method for the Identification of Uncharacterized Viruses Related To known Virus Groups: Hepadnavirus Model System," Proceedings of the National Academy of Sciences, 1988, vol. 85 (18), pp. 6977-6981.
Magnuson V.L., et al., "Substrate Nucleotide-Determined Non-Templated Addition of Adenine by Tag DNA Polymerase: Implications for PCR-Based Genotyping and Cloning," BioTechniques, 1996, vol. 21 (4), pp. 700-709.
Maiwald M., et al., "Characterization of Contaminating DNA in Tag Polymerase which Occurs During Amplification with a Primer Set for *Legionella* 5S Ribosomal RNA," Molecular and Cellular Probes, 1994, vol. 8 (1), pp. 11-14.
Malasig M.D., et al., "Simplified Microneutralization Test for Serotyping Adenovirus Isolates," Journal of Clinical Microbiology, 2001, vol. 39 (8), pp. 2984-2986.
Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.
Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.
Marks F., et al., "Genotyping of *Plasmodium falciparum* Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

(56) References Cited

OTHER PUBLICATIONS

Marmur J., et al., "Strand Separation and Specific Recombination in Deoxyribonucleic Acids: Biological Studies," Proceedings of the National Academy of Sciences, 1960, vol. 46 (4), pp. 453-461.

Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.

Martineau F., et al., "Development of a PCR Assay for Identification of Staphylococci at Genus and Species Levels," Journal of Clinical Microbiology, 2001, vol. 39 (7), pp. 2541-2547.

Martineau F., et al., "Species-Specific and Ubiquitous-DNA-Based Assays for Rapid Identification of Staphylococcus aureus," Journal of Clinical Microbiology, 1998, vol. 36 (3), pp. 618-623.

Martin-Lopez J.V., et al., "Simultaneous PCR Detection of Ica Cluster and Methicillin and Mupirocinresistance Genes in Catheter-Isolated Staphylococcus," International Microbiology, 2004, vol. 7 (1), pp. 63-66.

Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.

Matray T.J., et al., "Synthesis and Properties of RNA Analogs-Oligoribonucleotide N3-->p5 Phosphoramidates," Nucleic Acids Research, 1999, vol. 27 (20), pp. 3976-3985.

Matsuoka M., et al., "Characteristic Expression of Three Genes, msr(A), mph(C) and erm(Y), Thatconfer Resistance to Macrolide Antibiotics on Staphylococcus aureus," FEMS Microbiology Letters, 2003, vol. 220 (2), pp. 287-293.

May A.C., "Percent Sequence Identity: The Need to be Explicit," Structure, 2004, vol. 12 (5), pp. 737-738.

McCabe K.M., et al., "Bacterial Species Identification After DNA Amplification with a Universal Primer Pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Mehrotra M., et al., "Multiplex PCR for Detection of Genes for Staphylococcus aureus Enterotoxins, Exfoliative Toxins, Toxic Shock Syndrome Toxin 1, and Methicillin Resistance," Journal of Clinical Microbiology, 2000, vol. 38 (3), pp. 1032-1035.

Meiyu F., et al., "Detection of Flaviviruses by Reverse Transcriotase-Polymerase Chain Reaction with the Universal Primer Set," Microbiology and Immunology, 1997, vol. 41 (3), pp. 209-213.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of Staphylococcus aureus and Methicillin-Resistant S. aureus," Journal of Clinical Microbiology, 2000, vol. 38 (6), pp. 2378-2380.

Merlino J., et al., "Rapid Detection of Non-Multidrug-Resistant and Multidrug-Resistant Methicillin-Resistant Staphylococcus aureus Using Cycling Probe Technology for the mecA Gene," European Journal of Clinical Microbiology and Infectious Diseases, 2003, vol. 22 (5), pp. 322-323.

Messmer T.O., et al., "Discrimination of Streptococcus pneumoniae from Other Upper respiratory tract Streptococci by Arbitrary Primed PCR," Clinical Biochemistry, 1995, vol. 28 (6), pp. 567-572.

Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.

Miller K.W., et al., "A Compendium of Human Mitochondrial DNA Control Region: Development of an International Standard Forensic Database," Croatian Medical Journal, 2001, vol. 42 (3), pp. 315-327.

Miragaia M., et al., "Genetic Diversity among Methicillin-Resistant Staphylococcus epidemidis(MRSE)," Microbial Drug Resistance, 2005, vol. 11 (2), pp. 83-93.

Miura-Ochiai R., et al., "Quantitative Detection and Rapid Identification of Human Adenoviruses," Journal of Clinical Microbiology, 2007, vol. 45 (3), pp. 958-967.

Mollet C., et al., "RpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Moricca S., et al., "Detection of Fusarium oxysporum f.sp. Vasinfectum in Cotton Tissue by Polymerase Chain Reaction," Plant Pathology, 1998, vol. 47 (4), pp. 486-494.

Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.

Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp, 1201-1204.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.

Murakami K., et al., "Identification of Methicillin-Resistant Strains of Staphylococci by Polymerase Chain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.

Na B.K., et al,, "Detection and Typing of Respiratory Adenoviruses in a Single-Tube Multiplex Polymerase Chain Reaction," Journal of Medical Virology, 2002, vol. 66 (4), pp. 512-517.

Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.

(56) References Cited

OTHER PUBLICATIONS

Nagy M., et al., "Sequence Analysis of Porcine Adenovirus Serotype 5 Fibre Gene: Evidence for Recombination," Virus Genes, 2002, vol. 24 (2), pp. 181-185.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Nakagawa S., et al., "Gene Sequences and Specific Detection for Panton-Valentine Leukocidin," Biochemical and Biophysical Research Communications, 2005, vol. 328 (4), pp. 995-1002.
Nakao H., et al., "Development of a Direct PCR Assay for Detection of the Diphtheria Toxin Gene," Journal of Clinical Microbiology, 1997, vol. 35 (7), pp. 1651-1655.
Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp, 195-206.
Naumov G.I., et al., "Discrimination Between the Soil Yeast Species *Williopsis saturnus* and *Williopsis suaveolens* by the Polymerase Chain Reaction with the Universal Primer N21," Microbiology, 2000, vol. 69 (2), pp. 229-233.
NEB Catalog, 1998/1999, pp. 1, 79, 121 and 284.
Neumann G., et al., "Host Range Restriction and Pathogenicity in the Context of Influenza Pandemic," Emerging Infectious Diseases, 2006, vol. 12 (6), pp. 881-886.
Newcombe J., et al., "PCR of Peripheral Blood for Diagnosis of Meningococcal Disease," Journal of Clinical Microbiology, 1996, vol. 34 (7), pp. 1637-1640.
Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ng E.K., et al., "Serial Analysis of the Plasma Concentration of SARS Coronavirus RNA In Pediatric Patients with Severe Acute Respiratory Syndrome," Clinical Chemistry, 2003, vol. 49 (12), pp. 2085-2088.
Ni J., et al., "Interpretation of Oligonucleotide Mass Spectra for Determination of Sequence Using Electrospray Ionization and Tandem Mass Spectrometry," Analytical Chemistry, 1996, Vol, 68 (13), pp. 1989-1999.
Nilsson M., et al., "Evaluation of Mitochondrial DNA Coding Region Assays for Increased Discrimination in Forensic Analysis," Forensic Science International: Genetics, 2008, vol. 2 (1), pp. 1-8.
Nishikawa T., et al., "Reconstitution of Active Recombinant Ship Toxin (Stc)1 from Recombinant Stxl-A and Sbtl-B Subunits Independently Produced by *E. coli* Clones," FEMS Microbiol Letters, 1999, vol. 178 (1), pp. 13-18.
Non-Final Office Action mailed Feb. 2, 2007 for U.S. Appl. No. 10/844,938, filed May 12, 2004.
Non-Final Office Action mailed Oct. 2, 2009 for U.S. Appl. No. 11/929,707, filed Oct. 30, 2007.
Non-Final Office Action mailed Aug. 4, 2010 for U.S. Appl. No. 12/049,949, filed Mar. 17, 2008.
Non-Final Office Action mailed Apr. 6, 2009 for U.S. Appl. No. 11/331,987, filed Jan. 13, 2006.
Non-Final Office Action mailed Apr. 7, 2006 for U.S. Appl. No. 10/964,571, filed Oct. 12, 2004.
Non-Final Office Action mailed Aug. 7, 2007 for U.S. Appl. No. 10/844,938, filed May 12, 2004.
Non-Final Office Action mailed Jun. 10, 2009 for U.S. Appl. No. 10/844,938, filed May 12, 2004.
Non-Final Office Action mailed Jan. 12, 2010 for U.S. Appl. No. 11/491,376, filed Jul. 21, 2006.
Non-Final Office Action mailed Oct. 13, 2010 for U.S. Appl. No. 10/754,415, filed Jan. 9, 2004.
Non-Final Office Action mailed Sep. 16, 2009 for U.S. Appl. No. 11/233,630, filed Sep. 21, 2005.
Non-Final Office Action mailed Apr. 17, 2009 for U.S. Appl. No. 12/211,641, filed Sep. 16, 2008.
Non-Final Office Action mailed Nov. 19, 2003 for U.S. Appl. No. 09/798,007, filed Mar. 2, 2001.
Non-Final Office Action mailed Aug. 20, 2007 for U.S. Appl. No. 11/582,863, filed Oct. 17, 2006.
Non-Final Office Action mailed May 20, 2008 for U.S. Appl. No. 10/844,938, filed May 12, 2004.
Non-Final Office Action mailed Oct. 20, 2004 for U.S. Appl. No. 09/891,793, filed Jun. 26, 2001.
Non-Final Office Action mailed Feb. 23, 2009 for U.S. Appl. No. 10/660,122, filed Sep. 11, 2003.
Non-Final Office Action mailed May 26, 2010 for U.S. Appl. No. 11/869,449, filed Oct. 9, 2007.
Non-Final Office Action mailed Jul. 27, 2006 for U.S. Appl. No. 11/209,439, filed Aug. 8, 2005.
Non-Final Office Action mailed Jun. 28, 2010 for U.S. Appl. No. 11/930,002, filed Oct. 30, 2007.
Non-Final Office Action mailed Sep. 28, 2009 for U.S. Appl. No. 11/930,017, filed Oct. 30, 2007.
Non-Final Office Action mailed Dec. 29, 2010 for U.S. Appl. No. 12/616,422, filed Nov. 11, 2009.
Non-Final Office Action mailed Apr. 30, 2010 for U.S. Appl. No. 11/930,108, filed Oct. 31, 2007.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/Ionization Mass Spectrometry of Nucleic Acids with Wavelengths in the Ultraviolet and Infrare," Rapid Communictions in Mass Spectrometry, 1992, vol. 6 (12), pp. 771-776.
Notice of Allowance mailed Apr. 1, 2011 for U.S. Appl. No. 11/233,630, filed Sep. 21, 2005.
Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.
Notice of Allowance mailed Aug. 6, 2009 for U.S. Appl. No. 10/728,486, filed Dec. 5, 2003.
Notice of Allowance mailed Jun. 9, 2011 for U.S. Appl. No. 11/331,987, filed Jan. 13, 2006.
Notice of Allowance mailed Jun. 9, 2011 for U.S. Appl. No. 11/491,376, filed Jul. 21, 2006.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed Jan. 13, 2006.
Notice of Allowance mailed May 25, 2011 for U.S. Appl. No. 11/929,707, filed Oct. 30, 2007.
Notice of Allowance mailed Oct. 29, 2009 for U.S. Appl. No. 10/660,122, filed Sep. 11, 2003.
Nubel U.,et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFFT-ICR Mass Spectrometry," The American Society for Mass Spectrometry, 2002, vol. 13 (4), pp. 338-344.

(56) References Cited

OTHER PUBLICATIONS

Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Elestrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Nunes E.L., et al., "Detection of IleS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.
Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action mailed Apr. 1, 2004 for U.S. Appl. No. 10/156,608, filed May 24, 2002.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135, filed Feb. 17, 2005.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed Oct. 2, 2008 for U.S. Appl. No. 11/233,630, filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed Jun. 4, 2009 for U.S. Appl. No. 10/754,415, filed Jan. 9, 2004.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Sep. 5, 2006 for U.S. Appl. No. 10/660,996, filed Sep. 12, 2003.
Office Action mailed Jan. 6, 2011 for Israel Application No. 157661 filed Mar. 4, 2002.
Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed Sep. 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998, filed Sep. 12, 2003.
Office Action mailed Aug. 7, 2007 for U.S. Appl. No. 10/660,998, filed Sep. 12, 2003.
Office Action mailed Feb. 7, 2008 for European Application No. 03796752.8 filed Dec. 5, 2003.
Office Action mailed Jun. 7, 2010 for European Application No. 06800205.4 filed Jul. 27, 2006.
Office Action mailed Jan. 8, 2003 for U.S. Appl. No. 09/798,007, filed Mar. 2, 2001.
Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Appliction No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Dec. 10, 2008 for U.S. Appl. No. 10/829,826, filed Apr. 22, 2004.

(56) References Cited

OTHER PUBLICATIONS

Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed Jun. 12, 2009 for Chinese Application No. 200480016187.9 filed May 13, 2004.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S. Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006 for U.S. Appl. No. 10/754,415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Jun. 17, 2008 for U.S. Appl. No. 11/082,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.
Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.

(56) References Cited

OTHER PUBLICATIONS

Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed May 23, 2003 for U.S. Appl No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.
Office Action mailed Feb. 27, 2003 for U.S. Appl. No. 09/798,007, filed Mar. 2, 2001.
Office Action mailed Feb. 27, 2007 for U.S. Appl. No. 10/754,415, filed Jan. 9, 2004.
Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Aug. 30, 2007 for U.S. Appl. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.

(56) References Cited

OTHER PUBLICATIONS

Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
O''Guinn M.L., et al., "Field Detection of Eastern Equine Encephalitis Virus in the Amazon Basin Region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*, " Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions Run to Saturation," Nucleic Acids Research, 1993, vol. 21 (3), pp, 577-583.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Partial European Search Report for Application No. EP01106974, mailed on Dec. 16, 2002, 2 pages.
Pastorino B., et al., "Development of a TaqMan PCR Assay Without RNA Extraction Step for the Detection and Quantification of African Chikungunya Viruses," Journal of Virological Methods, 2005, vol. 124 (1-2), pp. 65-71.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pawa A., et al., "Co-Transfer of Plasmids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.
Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.
Peng X., et al., "Rapid Detection of *Shigella* Species in Environmental Sewage by an Immunocapture PCR with Universal Primers," Applied and Environmental Microbiology, 2002, vol. 68 (5), pp. 2580-2583.
Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.
Peters S.E., et al., "Quantification of the Detection of *Pneumocystis carinii* by DNA Amplification," Molecular and Cellur Probes, 1992, vol. 6 (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.
Pillai S.D., et al., "Rapid Molecular Detection of Microbial Pathogens: Breakthroughs and Challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of Adenovirus using PCR and Molecular Beacon," Journal of Virological Methods, 1999, vol. 82 (1), pp. 19-26.
Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-Based Detection and Typing of Human Adenoviruses in Clinical Samples," Research in Virology, 1997, vol. 148 (3), pp. 225-231.
Promega. T4 Polynucleotide Kinase, Technical Bulletin No. 519, 2002.
Puthavathana P., et al., "Molecular Characterization of the Complete Genome of Human Influenza H5N1 Virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.

(56) References Cited

OTHER PUBLICATIONS

Ramisse V., et al., "Identification and Characterization of *Bacillus anthracis* by Multiplex PCR Analysis of Sequences on Plasrnids pX01 and pX02 and Chromosomal DNA," Fems Microbiology Letters, 1996, vol. 145 (1), pp. 9-16.
Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.
Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.
Reischl U., "Application of Moloecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.
Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of *Bacillus subtilis* and *Bacillus mojavensis*," Evolution, 1995, vol. 49(6), pp. 1081-1094.
Robinson D.A., et al., "Multilocus Sequence Typing and the Evolution of Methicillin-Resistant *Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P., et al., "High Level Multiplex Genotyping by MALDI-TOF Mass Spectrometry," Nature Biotechnology, 1998, vol. 16 (13), pp. 1347-1351.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA Clone of the Nucleoprotein Gene of Influenza B/Ann Arbor/1/86," Nucleic Adds Research, 1989, vol. 17 (9), pp. 3595.
Ruan Y., et al., "Comparative Full-Length Genome Sequence Analysis of 14 SARS Coronavirus Isolates and Common Mutations Associated with the Putative Origins of Infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative Determination of *Streptococcus mutans* by using Competitive Polymerasechain Reaction," European Journal of Oral Sciences, 1999, vol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of PCR-Based Methods for Typing *Staphylococcus aureus* Isolates," Journal of Clinical Microbiology, 2006, vol. 44 (10), pp, 3804-3807.
Sackesen C., et al., "Use of Polymerase Chain Reaction for Detection of Adenovirus in Children Withor Without Wheezing," Turkish Journal of Pediatrics, 2005, vol. 47 (3), pp. 227-231.
Sakai H., et al., "Simultaneous Detection of *Staphylococcus aureus* and Coagulase-Negative Staphylococci in Positive Blood Cultures by Real-Time PCR with Two Fluorescence Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D-Ribofuranosyl)-Imidazole-4-Carboxamide During PCR," Nucleic Acids Research, 1996, vol. 24 (17), pp. 3302-3306.
Sambrook J., et al., "Molecular Cloning—A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and Molecular Characterization of Ebola Viruses Causing Disease in Human and Nonhuman Primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.
Santos S.R., et al., "Identification and Phylogenetic Sorting of Bacterial Lineages with Universally Conserved Genes and Proteins,"Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Scheffner M., et al., "The E6 Oncoprotein Encoded by Human Papillomavirus Types 16 and 18 Promotes the Degradation of p53," Cell, 1990, vol. 63 (6), pp. 1129-1136.
Schena M., et al., "Genome Analysis with Gene Expression Microarrays," Bioessays, 1996, vol. 18 (5), pp. 427-431.
Scheuermann R.H., et al., "Polymerase Chain-Reaction-Based mRNA Quantification Using an Internal Standard: Analysis of Oncogene Expression," Methods in Enzymology, 1993, vol. 218, pp. 446-473.
Schlecht N.F., et al., "Viral Load as a Predictor of the Risk of Cervical Intraepithelial Neoplasia," British Journal of Cancer, 2003, vol. 103 (4), pp. 519-524.
Schmidt T.M., et al., "Analysis of a Marine Pikoplankton Community by 16s rRNA Gene Cloning and Sequencing," Journal of Bacteriology, 1991, vol. 173 (14), pp. 4371-4378.
Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.
Schmitz F.J., et al., "Development of Resistance to Ciprofloxacin, Rifampin, and Mupirocin in Methicillin-Susceptible and -Resistant *Staphylococcus aureus* Isolates," Antimicrobial Agents and Chemotherapy, 2000, vol. 44 (11), pp. 3229-3231.
Schmitz F.J., et al., "Specific Information Concerning Taxonomy, Pathogenicity and Methicillin Esistance of Staphylococci Obtained by a Multiplex PCR," Journal of Medical Microbiology, 1997, vol. 46 (9), pp. 773-778.

(56) References Cited

OTHER PUBLICATIONS

Schram K.H., et al., "Mass Spectrometry of Nucleic Acid Components," Methods of Biochemical Analysis, 1990, vol. 34, pp. 203-280.
Schultz J.C., et al., "Polymerise Chain Reaction Products Analyzed by Charge Detection Mass Spectrometry," Rapid Communications in Mass Spectrometry, 1999, vol. 13 (1), pp. 15-20.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides of RFLP Analysis," Clinical Genetics, 1989, vol. 36 (6), pp. 419-426.
Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.
Sciacchitano C.J., "Analysis of Polymerase Chain Reaction-Amplified DNA Fragments of *Clostridium botulinum* Type E Neurotoxin Gene By High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of *Coxiella burnetii*," Infection and Immunity, 1999, vol. 67 (11), pp. 6026-6033.
Shadan F.F., et al., "N-Butyrate, A Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of *Bacilus subtilis* Sub-Groups," Journal of Microbiological Methods, 2002, vol. 50 (2), pp. 215-223.
Shaver Y.J., et al., "Variation in 16s-23s rRNA Intergenic Spacer Regions Among *Bacilus subtilis* 168 Isolates," Molecular Microbiology, 2001, vol. 42 (1), pp. 101-109.
Shimaoka M., et al., "Detection of the Gene for Toxic Shock Syndrome Toxin 1 in *Siaphylococcus aureus* by Enzyme-Labelled Oligonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant *Staphylococcus aureus*," Journal of Clinical Microbiology, 1994, vol. 32 (8), pp. 1866-1869.
Shrestha N.K., et al., "Rapid Identification of *Staphylococcus aureus* and the MecA Gene from BacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a New 3-h Hybridization Method for Detecting the MecA Gene in *Staphylococcus aureus* and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from *Bacilus thuringiensis* Strains and Characterization of a Novel Cry11-Type Gene," Applied and Environmental Microbiology, 2003, vol. 69, pp. 5207-5211.
Spackman E., et al., "Development of a Real-Time Reverse Transcriptase PCR Assay for Type A Influenzavirus and The Avian H5 and H7 Hemagglutinin Subtypes," Journal of Clinical Microbiology, 2002, vol. 40 (9), pp. 3256-3260.
Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.
Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Stratagene Catalog, Gene Characterization Kits, 1988, pp. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of Staphylococci," Journal of Clinical Pathology, 2003, vol. 56 (10), pp. 782-785.
Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. 04775904.8, mailed on Jul. 7, 2008, 8 pages.
Supplementary European Search Report for Application No. EP03796752.8, mailed on Aug. 7, 2007, 3 pages.
Supplementary European Search Report for Application No. EP03810055.8, mailed on Jun. 8, 2007, 4 pages.
Supplementary European Search Report for Application No. EP03814656, mailed on Oct. 16, 2007, 2 pages.
Supplementary European Search Report for Application No. EP04752257.8, mailed on Feb. 15, 2006, 2 pages.
Supplementary European Search Report for Application No. EP05753037, mailed on Aug. 21, 2009, 2 pages.
Supplementary Partial European Search Report for Application No. EP02709785.6, mailed Sep. 1, 2005, 5 pages.

(56) References Cited

OTHER PUBLICATIONS

Supplementary Partial European Search Report for Application No. EP05751872.2, mailed on Jan. 28, 2008, 8 pages.

Supplementary Partial European Search Report for Application No. EP05856582.1, mailed on Oct. 27, 2008, 10 pages.

Swaminathan B., et al., "PulseNet: The Molecular Subtyping Network for Foodborne Bacterial Disease Surveillance, United States," Emerging Infectious Diseases, 2001, vol. 7 (3), pp. 382-389.

Swanborg R.H., et al., "Human Herpesvirus 6 and *Chlamydia pneumoniae* as Etiologic Agents in Multiplesclerosis—a Critical Review," Microbes and Infection / Institut Pasteur, 2002, vol. 4 (13), pp. 1327-1333.

Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.

Takagaki Y., et al., "Four Factors are Required for 3"-End Cleavage of Pre-mRNAs," Genes and Development, 1989, vol. 3 (11), pp. 1711-1724.

Takahashi H., et al., "Characterization of gryA, gryB, grlA and grlB Mutations in Fluoroquinolone-Resistant Clinical Isolates of *Staphylococcus aureus*," The Journal of Antimicrobial Chemotherapy, 1998, vol. 41 (1), pp. 49-57.

Takahata M., et al., "Mutations in the GyrA and Grl A Genes of Quinolone-Resistant Clinical Isolates of Methicillin-Resistant *Staphylococcus aureus*," The Journal of Antimicrobial Chemotherapy, 1996, vol. 38 (3), pp. 543-546.

Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.

Takeuchi S., et al., "Serotyping of Adenoviruses on Conjunctival Scrapings by PCR and Sequence Analysis," Journal of Clinical Microbiology, 1999, vol. 37 (6), pp. 1839-1845.

Talaat A.M., et al., "Genome-Directed Primers for Selective Labeling of Bacterial Transcripts for DNA Microarray Analysis," Nature Biotechnology, 2000, vol. 17, pp. 679-682.

Tan T.Y., "Use of Molecular Techniques for the Detection of Antibiotic Resistance in Bacteria," Expert Review of Molecular Diagnostics, 2003, vol. 3 (1), pp. 93-103.

Tanabe F., et al., "The Properties and Mec A Gene of the Methicillin-Resistant *Staphylococcus aureus* Isolated in Fukushima Medical College Hospital," Fukushima Journal of Medical Science, 1993, vol. 39 (1), pp. 35-42.

Tang K., et al., "Detection of 500-Nucleotide DNA by Laser Desorption Mass Spectrometry," Rapid Communications in Mass Spectrometry, 1994, vol. 8 (9), pp. 727-730.

Tang K., et al., Double-Stranded DNA Analysis by Matrix Assisted Laser Desorption/Ionization, 42nd ASMS Conference on Mass Spectrometry, 1994.

Tang K., et al., "Matrix-Assisted Laser Desorption/Ionization of Restriction Enzyme-Digested DNA," Rapid Communications in Mass Spectrometry, 1994, vol. 8 (2), pp. 183-186.

Tang K., et al., Matrix-Assisted Laser Desorption/Ionization Mass Spectrometry of Oligonucleotides, Dissertation submitted to the Faculty of Vanderbilt University, 1994.

Tarassishin L., et al., "Adenovirus Core Protein VII Displays a Linear Epitope Conserved in a Range of Human Adenoviruses," Journal of General Virology, 1999, vol. 80 (Pt 1), pp. 47-50.

Tarassishin L., et al., "An Epitope on the Adenovirus Fibre Tail is Common to all Human Subgroups," Archives of Virology, 2000, vol. 145 (4), pp. 805-811.

Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.

Taubenberger J.K., et al., "Characterization of the 1918 Influenza Virus Polymerase Genes," Nature, 2005, vol. 437 (7060), pp. 889-893.

Taylor L.H., et al., "Risk Factors for Human Disease Emergence," Philosophical Transactions of the Royal Society of London Series B, Biological Sciences, 2001, vol. 356 (1411), pp. 983-989.

Tenover F.C., et al., "Characterization of a Strain of Community-Associated Methicillin-Resistant*Staphylococcus aureus* Widely Disseminated in the United States," Journal of Clinical Microbiology, 2006, vol. 44 (1), pp. 108-118.

Teramura T., et al., "Quantitative Detection of Serum Adenovirus in a Transplant Recipient," Lancet, 2002, vol. 359 (9321), pp. 1945.

Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.

Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.

Thompson W.W., et al., "Influenza-Associated Hospitalizations in the United States," The Journal of the American Medical Association, 2004, vol. 292 (11), pp. 1333-1340.

Tokue Y., et al., "Comparison of a Polymerase Chain Reaction Assay and a Conventional Microbiologic Method for Detection of Methicillin-Resistant *Staphylococcus aureus*," Antimicrobial Agents and Chemotherapy, 1992, vol. 36 (1), pp. 6-9.

Tong J., et al., "Ligation Reaction Specificities of an NAD+-Dependent DNA Ligase from the Hyperthermophile *Aquifex aeolicus*," Nucleic Acids Research, 200, vol. 28 (6), pp. 1447-1454.

Top F.H Jr., "Control of Adenovirus Acute Respiratory Disease in U.S. Army Trainees," The Yale Journal of Biology and Medicine, 1975, vol. 48 (3), pp. 185-195.

Torroni A., et al., "Classification of European mtDNAs from an Analysis of Three European Populations," Genetics, 1996, vol. 144 (4), pp. 1835-1850.

Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.

Tsuneyoshi T., et al., "Mass Spectrometric Gene Diagnosis of One-Base Substitution from Polymerase Chain Reaction Amplified Human DNA," Rapid Communications in Mass Spectometry, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.

Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.

Unal S., et al., "Detection of Methicillin-Resistant Staphylococci by Using the Polymerase Chain Reaction," Journal of Clinical Microbiology, 1992, vol. 30 (7), pp. 1685-1691.

Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.

Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Aerschot A., et al., "In Search of Acyclic Analogues as Universal Nucleosides in Degenerate Probes," Nucleosides and Nucleotides, 1995, vol. 14 (3-5), pp. 1053-1056.

Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.

(56) References Cited

OTHER PUBLICATIONS

Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implemetation," International Journal of Food Microbiology, 1996, vol. 33 (1), pp. 35-49.
Van Der Zee H., et al., "Rapid and Alternative Screening Methods for Microbiological Analysis," Journal of AOAC International, 1997, vol. 80 (4), pp. 934-940.
Van Dinten L.C., et al., "Proteolytic Processing of the Open Reading Frame Ib-EncodedPart of Arterivirus Replicase Is Mediated by nsp4 Serine Protease and is Essential for Virus Replication," Journal of Virology, 1999, vol. 73 (3), pp. 2027-2037.
Van Elden L.J., et al., "Clinical Diagnosis of Influenza Virus Infection: Evaluation of Diagnostic Tools in General Practice," The British Journal of General Practice, 2001, vol. 51 (469), pp. 630-634.
Van Elden L.J., et al., "Simultaneous Detection of Influenza Viruses A and B Using Real-Time Quantitative PCR," Journal of Clinical Microbiology, 2001, vol. 39 (1), pp. 196-200.
Van Ert M.N., et al., "Mass Spectrometry Provides Accurate Characterization of Two Genetic Marker Types in *Bacillus anthracis*," Bio Techniques, 2004, vol. 37 (4), pp. 642-651.
Van Leeuwen W.B., et al., "Multilocus Sequence Typing of *Staphylococcus aureus* with DNA Array Technology," Journal of Clinical Microbiology, 2003, vol. 41 (7), pp. 3323-3326.
Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.
Vanchiere J.A., et al., "Detection of BK Virus and Simian Virus 40 in the Urine of Healthy Children," Journal of Medical Virology, 2005, vol. 75 (3), pp. 447-454.
Vanderhallen H., et al.,, "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.
Vannuffel P., et al., "Specific Detection of Methicillin-Resistant *Staphylococcus* Species by Multiplex PCR," Journal of Clinical Microbiology, 1995, vol. 33 (11), pp. 2864-2867.
Verma S., et al., "Modified Oligonucleotides: Synthesis and Strategy for Users," Annual Review of Biochemistry, 1998, vol. 67, pp. 99-134.
Videla C., et al., "Genomic Analysis of Adenovirus Isolated from Argentinian Children with Acute Lower Respiratory Infections," Journal of Clinical Virology, 1999, vol. 14 (1), pp. 67-71.
Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp, 109-116.
Voelter C., et al., "Screening Human Tumor Samples with a Broad-Spectrum Polymerase Chain Reaction Method for the Detection of Polyomaviruses," Virology, 1997, vol. 237 (2), pp. 389-396.
Volokhov D., et al., "Microarray Analysis of Erythromycin Resistance Determinants," Journal of Applied Microbiology, 2003, vol. 95 (4), pp. 787-798.
Von Eiff C., et al., "Pathogenesis of Infections Due to Coagulase-Negative Staphylococci," The Lancet Infectious Diseases, 2002, vol. 2 (11), pp. 677-685.
Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.
Wallace S.S., et al., "The Enigma of Endonuclease VIII," DNA Repair, 2003, vol. 2 (5), pp. 441-453.
Wallet F., et al., "Choice of a Routine Method for Detecting Methicillin-Resistance in Staphylococci," The Journal of Antimicrobial Chemotherapy, 1996, vol. 37 (5), pp. 901-909.
Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.
Wang G., et al., "Targeted Mutagenesis in Mammalian Cells Mediated by Intracellular Triple Helix Formation," Molecular and Cellular Biology, 1995, vol. 15 (3), pp. 1759-1768.
Ward C.L., et al., "Design and Performance Testing of Quantitative Real Time PCR Assays for Influenza A and B Viral Load Measurement," Journal of Clinical Virology, 2004, vol. 29 (3), pp. 179-188.
Watanabe K., et al., "ICB Database: The gyrB Database for Identification and Classification of Bacteria," Nucleic Acids Research, 2001, vol. 29 (1), pp. 344-345.
Weissenbacher M., et al., "Etiologic and Clinical Evaluation of Acute Lower Respiratory Tractinfections in Young Argentinean Children: An Overview," Reviews of Infectious Diseases, 1990, vol. 12 (Suppl 8), pp. S889-S898.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-Resistant*Staphylococcus aureus*," Journal of Clinical Micrfobiology, 1999, vol. 37 (3), pp. 690-693.
Wickham T.J., "Targeting Adenovirus," Gene Therapy, 2000, vol. 7 (2), pp. 110-114.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.
Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.
Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Environmental Mass Spectrometry, 1987, vol. 14, pp. 111-116.
Woo T.H., et al., "Identification of *Leptospira inadai* by Continuous Monitoring of Fluorescence during Rapid Cycle PCR," Systematic and Applied Microbiology, 1998, vol. 21 (1), pp. 89-96.
Wood S.R., et al., "Rapid Detection and Serotyping of Adenovirus by Direct Immunofluorescence," Journal of Medical Virology, 1997, vol. 51 (3), pp. 198-201.
Wright K.E., et al., "Typing and Subtyping of Influenza Viruses in Clinical Samples by PCR," Journal of Clinical Microbiology, 1995, vol. 33 (5), pp. 1180-1184.

(56) References Cited

OTHER PUBLICATIONS

Written Opinion for Application No. PCT/US2004/33742, mailed on May 15, 2006, 5 pages.
Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.
Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.
Wunschel D., et al., "Discrimination Among the *B. cereus* Group, in Comparison to *B. subtilis*, by Structural Carbohydrate Profiles and Ribosomal RNA Spacer Region PCR," Systematic and Applied Microbiology, 1994, vol. 17, pp. 625-635.
Wunschel D.S., et al., "Analysis of Double-Stranded Polymerase Chain Reaction Products from the *Bacilus cereus* Group by Electrospray Lonization Fourier Transform Lon Cyclotron Resonance Mass Spectrometry," Rapid Communications in Mass Spectrometry, 1996, vol. 10 (1), pp. 29-35.
Wunschel D.S., et al., "Heterogeneity in *Bacillus cereus* PCR Products Detected by ESI-FTICR Mass Spectrometry," Analytical Chemistry, 1998, vol. 70 (6), pp. 1203-1207.
Wunschel D.S., et al., "Mass spectrometric characterization of DNA for molecular biological applications: advances using MALDI and ESI," Advances in Mass Spectrometry, 1998, vol. 14, Elsevier, pp. 377-406.
Xu L., et al., "Electrophore Mass Tag Dideoxy DNA Sequencing," Analytical Chemistry, 1997, vol. 69 (17), pp. 3595-3602.
Xu W., et al., "Species-Specific Identification of Human Adenoviruses by a Multiplex PCR Assay," Journal of Clinical Microbiology, 2000, vol. 38 (11), pp. 4114-4120.
Xu W., et al., "Type-Specific Identification of Human Adenovirus, 3, 7, and 21 by a Multiplex PCR Assay," Journal of Medical Virology, 2001, vol. 64 (4), pp. 537-542.
Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.
Yao Z.P., et al., "Mass Spectrometry Based Proteolytic Mapping for Rapid Virus Identification," Analytical Chemistry, 2002, vol. 74 (11), pp. 2529-2534.
Yasui T., et al., "A Specific Oligonucleotide Primer for the Rapid Detection of *Lactobacillus lindneri* by Polymerase Chain Reaction," Canadian Journal of Microbiology, 1997, vol. 43 (2), pp. 157-163.
Ye K., et al., "Three Distinct Promoters Direct Transcription of Different 5" Untranslated Regions of the Human Interleukin 1 Type 1 Receptor. A Possible Mechanism for Control of Translation," Cytokine, 1996, vol. 8 (6), pp. 421-429.
Yun H.J., et al., "Increased Antibacterial Activity of OW286, A Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.
Zeng Z.B., "Precision Mapping of Quantitative Trait Loci," Genetics, 1994, vol. 136 (4), pp. 1457-1468.
Zhang J., et al., "PowerBLAST: A New Network BLAST Application for Interactive or Automated Sequence Analysis and Annotation," Genome Research, 1997, vol. 7 (6), pp. 649-656.
Zhang K., et al., "New Quadriplex PCR Assay for Detection of Methicillin and Mupirocin Resistance and Simultaneous Discrimination of *Staphylococcus aureus* from Coagulase-Negative Staphylococci," Journal of Clinical Microbiology, 2004, vol. 42 (11), pp. 4947-4955.
Zhang W.D., et al., "Detection and Identification of Human Influenza Viruses by the Polymerase Chain Reaction," Journal of Virological Methods, 1991, vol. 33 (1-2), pp. 165-189.
Zhang Y.Q., et al., "Genome-Based Analysis of Virulence Genes in a Non-Biofilm-Forming *Staphylococcus epidemidis* Strain (ATCC 12228)," Molecular Microbiology, 2003, vol. 49 (6), pp. 1577-1593.

Final Office Action mailed Oct. 4, 2012 for U.S. Appl. No. 11/682,259, filed Mar. 5, 2007.
Notice of Allowance mailed Oct. 2, 2012 for U.S. Appl. No. 11/930,108, filed Oct. 31, 2007.
Office Action mailed Sep. 14, 2012 for Australian Application No. 2010200893 filed Mar. 10, 2010.
Office Action mailed Aug. 29, 2012 for Canadian Application No. 2439655 filed Mar. 4, 2002.
Co-pending U.S. Appl. No. 13/770,648, filed Feb. 19, 2013.
Co-pending U.S. Appl. No. 13/850,683, filed Mar. 26, 2013.
Final Office Action mailed Dec. 4, 2012 for U.S. Appl. No. 13/174,254, filed Jun. 30, 2011.
Final Office Action mailed Dec. 17, 2012 for U.S. Appl. No. 12/616,422, filed Nov. 11, 2009.
Non-Final Office Action mailed Jul. 3, 2013 for U.S. Appl. No. 11/929,930, filed Oct. 30, 2007.
Non-Final Office Action mailed Jun. 6, 2013 for U.S. Appl. No. 13/243,960, filed Sep. 23, 2011.
Non-Final Office Action mailed Jul. 12, 2013 for U.S. Appl. No. 13/174,254, filed Jun. 30, 2011.
Non-Final Office Action mailed Jan. 22, 2013 for U.S. Appl. No. 11/930,741, filed Oct. 31, 2007.
Non-Final Office Action mailed May 23, 2013 for U.S. Appl. No. 13/663,176, filed Oct. 29, 2012.
Notice of Allowance mailed Apr. 1, 2013 for U.S. Appl. No. 11/929,930, filed Oct. 30, 2007.
Notice of Allowance mailed Oct. 12, 2012 for U.S. Appl. No. 12/049,949, filed Mar. 17, 2008.
Notice of Allowance mailed Jun. 14, 2013 for U.S. Appl. No. 11/682,259, filed Mar. 5, 2007.
Notice of Allowance mailed Jan. 22, 2013 for U.S. Appl. No. 12/616,422, filed Nov. 11, 2009.
Notice of Allowance mailed May 22, 2013 for U.S. Appl. No. 12/616,422, filed Nov. 11, 2009.
Notice of Allowance mailed May 28, 2013 for U.S. Appl. No. 11/682,259, filed Mar. 5, 2007.
Office Action mailed Dec. 6, 2012 for European Application No. 10179795.9 filed Mar. 4, 2002.
Office Action mailed Dec. 12, 2012 for European Application No. 10179789.2 filed Mar. 4, 2002.
Office Action mailed Oct. 15, 2012 for European Application No. 10175659.1 filed Dec. 5, 2003.
Office Action mailed Apr. 19, 2013 for Canadian Application No. 2616281 filed Jul. 21, 2006.
Office Action mailed Nov. 21, 2012 for Israel Application No. 157661 filed Mar. 4, 2002.
Office Action mailed Apr. 23, 2013 for Japanese Application No. 2009550634 filed Feb. 25, 2008.
Office Action mailed Sep. 25, 2012 for Japanese Application No. 2008522997 filed Jul. 21, 2006.
Office Action mailed May 29, 2013 for Australian Application No. 2010200893 filed Mar. 10, 2010.
Notice of Allowance mailed Aug. 3, 2012 for U.S. Appl. No. 11/674,538, filed Feb. 13, 2007.
Notice of Allowance mailed Jul. 24, 2012 for U.S. Appl. No. 11/930,017, filed Oct. 30, 2007.
Office Action mailed Jun. 12, 2012 for Mexican Application No. PAa2003007927 filed Sep. 2, 2003.
Office Action mailed Jul. 25, 2012 for European Application No. 06800205.4 filed Jul. 21, 2006.
Office Action mailed May 24, 2012 for European Application No. 10179791.8 filed Mar. 4, 2002.
Office Action mailed May 29, 2012 for Indian Application No. IN4504/KOLNP/2007 filed Nov. 22, 2007.
Office Action mailed May 31, 2012 for Canadian Application No. 2616281 filed Jul. 21, 2006.
Co-pending U.S. Appl. No. 13/174,254, filed Jun. 30, 2011.
Co-pending U.S. Appl. No. 13/243,960, filed Sep. 23, 2011.
Ecker Supporting Information [online], May 23, 2005 [retrieved on Jul. 31, 2011]. Retrieved from the Internet:<URL: http://www.pnas.org/content/102/22/8012/suppl/DC1>.
Ex Parte Quayle Action mailed Nov. 21, 2011 for U.S. Appl. No. 12/049,949, filed Mar. 17, 2008.

(56) References Cited

OTHER PUBLICATIONS

Final Office Action mailed Oct. 19, 2011 for U.S. Appl. No. 12/326,800, filed Dec. 2, 2008.
Final Office Action mailed Jul. 28, 2011 for U.S. Appl. No. 11/930,108, filed Oct. 31, 2007.
GenBank, "Mouse Hepatitis Virus Strain MHV-A59 C12 Mutant, Complete Genome," Accession No. AF029248, Jul. 25, 2000.
Klijn N., et al., "Identification of Mesophilic Lactic Acid Bacteria by using Polymerase Chain Reaction-Amplified Variable Regions of 16S rRNA and Specific DNA Probes," Applied and Environmental Microbiology, 1991, vol. 57 (11), pp. 3390-3393.
Krenke B.E., et al., "Validation of a 16-Locus Fluorescent Multiplex System," Journal of Forensic Sciences, 2002, vol. 47 (4), pp. 773-785.
Non-Final Office Action mailed May 2, 2012 for U.S. Appl. No. 12/326,800, filed Dec. 2, 2008.
Non-Final Office Action mailed May 8, 2012 for U.S. Appl. No. 13/174,254, filed Jun. 30, 2011.
Non-Final Office Action mailed Oct. 11, 2011 for U.S. Appl. No. 12/605,628, filed Oct. 26, 2009.
Non-Final Office Action mailed Dec. 13, 2011 for U.S. Appl. No. 12/326,800, filed Dec. 2, 2008.
Non-Final Office Action mailed Oct. 13, 2011 for U.S. Appl. No. 11/929,930, filed Oct. 30, 2007.
Non-Final Office Action mailed Dec. 14, 2011 for U.S. Appl. No. 11/682,259, filed Mar. 5, 2007.
Non-Final Office Action mailed Feb. 16, 2012 for U.S. Appl. No. 11/674,538, filed Feb. 13, 2007.
Non-Final Office Action mailed Apr. 18, 2012 for U.S. Appl. No. 12/605,628, filed Oct. 26, 2009.
Non-Final Office Action mailed Mar. 21, 2012 for U.S. Appl. No. 12/616,422, filed Nov. 11, 2009.
Non-Final Office Action mailed Jan. 27, 2012 for U.S. Appl. No. 11/929,930, filed Oct. 30, 2007.
Notice of Allowance and Examiner Interview Summary Report mailed Jul. 21, 2011 for U.S. Appl. No. 10/754,415, filed Jan. 9, 2004.
Notice of Allowance mailed Apr. 9, 2012 for U.S. Appl. No. 11/929,910, filed Oct. 30, 2007.
Notice of Allowance mailed Aug. 9, 2011 for U.S. Appl. No. 11/930,002, filed Oct. 30, 2007.
Notice of Allowance mailed May 11, 2012 for U.S. Appl. No. 12/049,949, filed Mar. 17, 2008.
Notice of Allowance mailed Mar. 19, 2012 for U.S. Appl. No. 11/930,017, filed Oct. 30, 2007.
Notice of Allowance mailed Nov. 21, 2011 for U.S. Appl. No. 12/326,800, filed Dec. 2, 2008.
Notice of Allowance mailed Mar. 22, 2012 for U.S. Appl. No. 11/930,108, filed Oct. 31, 2007.
Notice of Allowance mailed Mar. 22, 2012 for U.S. Appl. No. 12/326,800, filed Dec. 2, 2008.
Notice of Allowance mailed May 23, 2012 for U.S. Appl. No. 12/326,800, filed Dec. 2, 2008.
Notice of Allowance mailed Feb. 29, 2012 for U.S. Appl. No. 11/929,910, filed Oct. 30, 2007.
Office Action mailed Dec. 2, 2011 for European Application No. 10179791.8 filed Mar. 4, 2002.
Office Action mailed Feb. 2, 2012 for Israel Application No. 157661 filed Mar. 4, 2002.
Office Action mailed Aug. 3, 2011 for Canadian Application No. 2439655 filed Mar. 4, 2002.
Office Action mailed Aug. 3, 2011 for European Application No. 08730682.5 filed Feb. 25, 2008.
Office Action mailed Jul. 5, 2011 for Mexican Application No. PAa2003007927 filed Sep. 2, 2003.
Office Action mailed Dec. 6, 2011 for Australian Application No. 2010200893 filed Mar. 10, 2010.
Office Action mailed Feb. 6, 2012 for Australian Application No. 2010202418 filed Jun. 10, 2010.
Office Action mailed Feb. 6, 2012 for European Application No. 06800205.4 filed Jul. 21, 2006.
Office Action mailed Jan. 10, 2012 for Japanese Application No. 2008522997 filed Jul. 21, 2006.
Office Action mailed Feb. 14, 2012 for Australian Application No. 2010200686 filed Feb. 25, 2010.
Office Action mailed Feb. 14, 2012 for European Application No. 10179789.2 filed Mar. 4, 2002.
Office Action mailed Jan. 19, 2012 for Canadian Application No. 2510007 filed Dec. 5, 2003.
Office Action mailed Oct. 20, 2011 for European Application No. 02709785.6 filed Mar. 4, 2002.
Office Action mailed Mar. 21, 2012 for Japanese Application No. 2009245976 filed Oct. 26, 2009.
Office Action mailed Nov. 30, 2011 for Australian Application No. 2010202418 filed Jun. 10, 2010.
Office Action mailed Sep. 30, 2011 for U.S. Appl. No. 10/754,415, filed Jan. 9, 2004.
Jan. 2004.
Final Office Action mailed Aug. 20, 2013 for U.S. Appl. No. 11/930,741, filed Oct. 31, 2007.
Co-pending U.S. Appl. No. 14/047,414, filed Oct. 7, 2013.
Co-pending U.S. Appl. No. 14/058,723, filed Oct. 21, 2013.
Final Office Action mailed Apr. 23, 2014 for U.S. Appl. No. 13/174,254, filed Jun. 30, 2011.
Non-Final Office Action mailed Apr. 21, 2014 for U.S. Appl. No. 13/663,176, filed Oct. 29, 2012.
Notice of Allowance mailed Apr. 3, 2014 for U.S. Appl. No. 11/929,930, filed Oct. 30, 2007.
Notice of Allowance mailed Apr. 11, 2014 for U.S. Appl. No. 11/930,741, filed Oct. 31, 2007.
Notice of Allowance mailed Apr. 24, 2014 for U.S. Appl. No. 13/243,960, filed Sep. 23, 2011.
Office Action mailed Jan. 24, 2014 for China Application No. CN201210348178 filed Mar. 4, 2002.
Non-Final Rejection mailed on May 14, 2014 for U.S. Appl. No. 13/850,683, filed on Mar. 26, 2013.

\* cited by examiner

Figure 6

Summary: 58 STR primer pairs: known sample

| LOCUS | ALLELE | Number of primer pairs tested | Number primer pairs confirming alleles |
|---|---|---|---|
| CSF1PO | 10, 11 | 5 | 5 |
| D13S317 | 12, 13ibis | 5 | 5 |
| D16S539 | 12, 13 | 4 | 4 |
| D18S51 | 16, 21 | 4 | 4 |
| D21S11 | UNKNOWN -- couldn't resolve | 2 | 0 |
| D3S1358 | 15' | 3 | 3 |
| D5S818 | 11ibis (apparent T-->C SNP masked by one of the four primer pairs) | 4 | 4 |
| D7S820 | 10, 13 | 5 | 5 |
| D8S1179 | 13, 14 | 3 | 3 |
| FGA | 23, 26 | 1 | 1 |
| THO1 | 6, 8 | 7 | 7 |
| TPOX | 6, 11 | 8 | 8 |
| VWA | 17 (19), 19 (21) | 3 | 3 |
| AMEL | X, Y (sample is apparently of male origin) | 3 | 3 |

Figure 8

AFDIL STR typing example: Sample I-0066, vWA, Primer pair 1184

Figure 12

| Sample | D5S818 | D8S1179 | TH01 | TPOX | vWA | AMEL | CSF1PO | D13S317 | D16S539 | D7S820 |
|---|---|---|---|---|---|---|---|---|---|---|
| I-0061 | 13, 13 (G→T) | 13, 14 | 7, 9.3 | 8, 9 | 14 (A→G, 2T→2C), 15 (G→A) | X, — | 11, 12 | 9, 11 (A→T) | 11, 12 | 8, — |
| I-0062 | 11, 12 | 10, — | 6, 8 | 8, 9 | 16, 18 | X, — | 11, 12 | 11, 13 | 11, 13 | 9, 10 |
| I-0065 | 9 (A→C), 12 | 11, 13 | 9.3, — | 8, 10 | 14 (G→A→C), 18 | X, Y | 10, — | 12, 13 (A→T) | 11, — | 10 (T→A), 12 |
| I-0066 | 11, 12 (G→T) | 11, 13 (G→A) | 9.3, — | 8, 11 | 14 (A→G, 2T→2C), 16 | X, — | 11, 12 | 10, 13 | 10, 11 | 10, 11 |
| I-0067 | 10, 13 (G→T) | 10, 14 | 7, 9.3 | 8, 9 | 17, 18 | X, Y | 11, 12 | 8, 9 | 9, 11 | 7, 10 (T→A) |
| I-0069 | 11, 12 | 10, 14 | 8, 9 | 8, 11 | 14 (A→G, 2T→2C), 19 | X, — | 11, 13 | 12, 14 (A→T) | 9, 14 | 10, 12 (T→A) |
| I-0070 | 12, — | 10, 13 | 6, — | 8, — | 15 (G→A), 17 | X, — | 12, — | 11, 12 | 12, — | 7, 12 |
| I-0074 | 12 (G→T), 13 | 8, 10 | 6, 7 | 8, 11 | 17, 19 | X, — | 9, 10 | 11, 11 (A→T) | 11, 13 | 9, — |
| I-0077 | 12, — | 13 (G→A), 15 | 7, 9 | 7, 10 | 16, 18 | X, — | 10, 11 | 11, 12 (A→T) | 9, 11 | 8, 10 |
| I-0078 | 10, 11 | 12, 14 | 6, 7 | 9, 12 | 17, 17 (G→A) | X, Y | 11, 12 | 8, 11 (A→T) | 9, 12 | 8, 10 |
| I-0079 | 11, 13 | 13, 16 | 9.3, — | 11, — | 19, 20 | X, — | 10, 12 | 8, 11 (A→T) | 10, 13 | 10, 11 (T→A) |
| I-0082 | 11, — | 12, 14 | 7, 9.3 | 8, 12 | 17, 19 | X, Y | 11, 12 | 11, 12 (A→T) | 9, 12 | 11, 12 |

Figure 13a

Typing summary for 25 AFDIL samples

Figure 13b

Typing summary for 22 FBI samples

| Sample | D5S818 | D8S1179 | THO1 | TPOX | AMEL | vWA | CSF1PO | D13S317 | D16S539 | D7S820 |
|---|---|---|---|---|---|---|---|---|---|---|
| FBI-3 | 11, 14 | 12, 14 | 6, 9.3 | 8, 11 | X, — | 15 (G→A) 18 | 10, — | 8, 11(A→T) | 11, 13 | 9, — |
| FBI-9 | 13, — | 15, 14 (G→A) | 6, 7 | 8, 9 | X, — | 17, — | 10, 11 | 11, 14 | 9, 12 | 11, — |
| FBI-22 | 11, — | 10, 13 | 7, 9.3 | 8, 9 | X, — | 18 (A→G) 19 | 10, 12 | 11 (A→T) 12 (A→T) | 10, 12 | 10 (T→A) 12 |
| FBI-28 | 9 (A→C) 11 | 12, 13 | 7, 9 | 8, 11 | X, Y | 19, — | 10, 11 | 12, 13 | 10, 11 | 10 (T→A) 12 |
| FBI-32 | 12, — | 9, 10 | 8, 9.3 | 8, 10 | X, — | 15 (G→A) 18 | 12, — | 5, 11(A→T) | 10, 12 | 10, 11 |
| FBI-33 | 11, 12 | 14, — | 6, 7 | 8, — | X, — | 18, — | 9, 11 | 14 (A→T) — | 12, — | 8, 12 (T→A) |
| FBI-37 | 11, 13 | 12, 14 | 6, 9 | 8, 10 | X, — | 14 (A→G, 2T→4C) 17 | 11, 12 | 11, 12 | 11, 13 | 8, 10 (T→A) |
| FBI-47 | 12 (G→T) 14 | 12, 13 | 6, 9.3 | 8, — | X, — | 17, 19 | 11, 12 | 11, 12 | 10, 12 | 12 (T→A) — |
| FBI-48 | 9 (A→C) 12 | 13, 16 | 9, 10 | 8, 11 | X, — | 17, 19 | 10, 11 | 8, 12(A→T) | 9, 11 | 11, 13 |
| FBI-49 | 12, — | 12, 15 | 6, — | 8, 9 | X, — | 16 (G→A) 17 | 12, 13 | 12 (A→T) 14(A→T) | 9, 13 | 9, 12 |
| FBI-51 | 11, — | 11, 15 | 6, — | 8, 11 | X, Y | 17, 19 | 11, — | 11, 14(A→T) | 11, 13 | 10, 12 |
| FBI-57 | 11, 12 | 9, 14 | 6, 9.3 | 8, 9 | X, — | 15 (G→A) 19 | 11, — | 8, 13 | 11, 13 | 11, 11 (T→A) |
| FBI-58 | 12, — | 11, 14 | 7, — | 8, 9 | X, Y | 17, — | 11, 12 | 10, 11(A→T) | 11, 12 | 10, 12 |
| FBI-61 | 9 (A→C) 11 | 10, 12 | 6, 9.3 | 8, 11 | X, — | 17(G→A) 17 | 10, 12 | 9, 11(A→T) | 12, 13 | 8, — |
| FBI-65 | 11 (G→T) 12 | 14, — | 8, 9 | 8, 9 | X, — | 15, 18 | 12, — | 8, 12 | 11, 12 | 10, 12 |
| FBI-66 | 11, 11(G→T) | 13, 14 | 8, 9.3 | 8, 11 | X, — | 16, 19 (A→G) | 10, — | 13, 14 | 12, — | 8, 12 (T→A) |
| FBI-67 | 11, 12 | 12, 13 | 9, — | 8, — | X, — | 16, 16 (G→A) | 11, 12 | 11 (A→T) 14 | 11, 12 | 10, 11 |
| FBI-69 | 11, — | 12, 14 | 7, 9.3 | 8, 9 | X, — | 15 (G→A) 16 | 12, 13 | 12, 13(A→T) | 12, 14 | 8, 9 |
| FBI-70 | 11, — | 13, 14 | 6, — | 8, — | X, Y | 18, — | 10, 11 | 12, — | 9, 11 | 8, 10 |
| FBI-72 | 11, 12 | 10, — | 9, 9.3 | 8, 11 | X, — | 18 (A→G) 19 | 11, — | 11 (A→T) 12 | 10, 12 | 8, 11 |
| FBI-75 | 12, 13 (G→T) | 11, 12 | 9.3, — | 8, 11 | X, — | 18, 18 (A→G) | 11, 12 | 9, 14 | 9, 13 | 9, 11 |
| FBI-82 | 12, 12(G→T) | 13, 14 | 7, 9.3 | 8, 11 | X, — | 14 (G→A, T→C) 17 | 10, 11 | 12 (A→T) 13 | 11, 12 | 11, — |
| FBI-101 | 11, 12 | 11, 13, 14 | 6, 7, 9.3 | 8, 10 | X, Y | 17, 18 | 9, 11 | 11, 12 (A→T) 14(A→T) | 9, 10, 12 | 8, 10, 11 |
| FBI-102 | 12, 12 (G→T), 14 | 12, 13, 11 | 6, 9.3 | 8, — | X, — | 15 (G→A) 17, 19 | 10, 11, 12 | 11, 12 | 10, 11, 12 | 12 (T→A) — |
| FBI-100 | —, — | —, — | —, — | —, — | —, — | —, — | —, — | —, — | —, — | —, — |
| Negative | —, — | —, — | —, — | —, — | —, — | —, — | —, — | —, — | —, — | —, — |

Figure 13c

| Locus | Number of Alleles with SNPs | % of Total Allele Calls Containing a SNP* | Number of Same-Length Heterozygous Loci |
|---|---|---|---|
| D5S818 | 22 | 23.4 | 3 |
| D8S1179 | 6 | 6.4 | 1 |
| vWA | 22 | 23.4 | 3 |
| D13S317 | 29 | 30.9 | 2 |
| D7S820 | 7 | 7.4 | 2 |

Figure 14

| | Sample | AMEL | CSF1PO | D13S317 | D16S539* | D18S51* | D21S11* | D3S1358* | D5S818 | D7S820 | D8S1179 | FGA* | THO1 | TPOX | vWA |
|---|---|---|---|---|---|---|---|---|---|---|---|---|---|---|---|
| Caucasian | UT57300 | X,Y | 10, 12 | 8, 12 | 9 f, 12 | 10, 13 | 28, — | 15, 16 d | 12, — | 8, 13 | 10, 15 | 20, 21 | 9.3, — | 8, 9 | 15 d, 19 |
| | UT57301 | X,Y | 11, 12 | 8, — | 11, 12 | 15, 17 | 28, — | 15 d, 18 d | 11 b, 13 | 8, 11 | 13, 14 | 23, 25 | 6, — | 8, — | 17, 18 |
| | UT57302 | X,Y | 10, 12 | 11 c, 12 c | 11, — | 14, 17 | 28, 29 | 15 d, 17 | 11, — | 8, 13 | 10, 13 | 21, 24 | 8, 9 | 8, 9 | 14 g, 17 |
| | UT57303 | X,Y | 10, 12 | 11 c, 13 | 9, 12 | 13, 14 | 29 d, 30 | 15 d, 17 | 11, 13 | 10, 12 e | 12, 13 | 21, 22 | 8, 9 | 8, 11 | 16, 17 |
| | UT57310 | X,Y | 12, — | 8, 13 | 9, 13 | 12, 13 | 30, 30.2 | 17 d, 18 | 12, — | 9, 10 | 12, — | 20, 21 | 9.3, — | 9, 11 | 14 a, 15 d |
| | UT57312 | X,Y | 11, 12 | 10 c, 11 | 10, 12 | 16, 18 | 28, 33.2 | 17 d, 17 j | 12 b, 12 | 11, 12 e | 13, 14 d | 23, 24 | 9.3, — | 8, — | 16, 17 |
| | UT57317 | X,Y | 11, 12 | 12 c, 13 | 9, 12 | 12, 17 | 29 d, 30.2 | 15 d, 15 j | 11, — | 8, 11 | 13, 14 d | 22, 23 | 6, 9.3 | 8, — | 14 a, 17 |
| | UT57318 | X,Y | 11, 13 | 11 c, 12 c | 11, — | 16, 18 | 25.2, 30 | 15 d, 16 d | 10, 12 b | 10, 11 | 12, — | 21, 22 | 9.3, — | 8, 11 | 15 d, 17 |
| | WT51342 | X,Y | 10, 12 | 11, 14 | 12, 13 | 13, 14 | 29, 31 d | 18, — | 12, 13 | 9, 12 | 12, 14 | 24, 25 | 9, 9.3 | 9, 11 | 18, — |
| | WT51343 | X,Y | 11, 13 | 11, 13 | 11, — | 14, 16 | 28, 31.2 | 16 d, 17 d | 11, 12 | 10, 12 e | 12, 13 d | 22, — | 6, 7 | 8, — | 17, 18 |
| | WT51345 | X,Y | 11, 12 | 11 c, — | 10, 13 | 13, — | 29, — | 15 d, 16 d | 11, — | 8, 10 | 13, 14 d | 20, 22 | 7, 9.3 | 8, — | 17, 19 |
| | WT51354 | X,Y | 10, 12 | 11, 14 | 11, 12 | 16, — | 30 d, 32.2 | 15 d, 16 | 8, 11 | 7, 9 | 11, 13 | 18, 26 | 6, 9.3 | 8, 9 | 13 l, 16 d |
| | WT51355 | X,Y | 10, 13 | 11, 12 | 12, — | 15, 17 | 30, 31.2 | 16 d, 18 | 11, — | 8, 10 | 13, 13 d | 20, 24 | 7, 9.3 | 10, 11 | 14 a, 16 |
| | WT51358 | X,Y | 11, 12 | 11, 12 c | 9, 13 | 20, 22 | 30, 31 d | 14, 18 | 10, — | 11, 13 | 11, 13 | 19, — | 7, 9.3 | 9, 11 | 15 d, 16 |
| | WT51359 | X,Y | 12, — | 13, — | 11, 13 | 13, 20 | 27 f, 32.2 | 14, 15 d | 13, — | 10, 12 | 14, 16 | 21, 24 | 9, 9.3 | 11, — | 15 d, 18 d |
| | WT51362 | X,Y | 11, 12 | 8, 13 | 9, 11 | 16, 19 | 30, 31 | 16, 17 d | 11, 12 | 10 e, 12 e | 10, — | 23, 24 | 9.3, — | 10, 11 | 17, 18 |
| | WT51373 | X,Y | 10, 12 | 11 c, 12 c | 11, 13 | 14, 17 | 28, — | 15 d, 18 | 10, 11 | 8, 11 | 11, 14 | 21, 22 | 8, 9 | 8, 11 | 15 d, 17 d |
| | WT51378 | X,Y | 10, — | 8, 12 | 9, 11 | 12, 15 i | 30, 31 d | 15, 18 | 11, — | 9, — | 13, — | 19, 23 | 6, 9 | 8, — | 16, 16 d |
| | WT51381 | X,Y | 12, — | 8, 11 | 9, 11 | 12, 18 | 30 d, — | 15 d, 17 | 12, 14 | 10, — | 10, 16 | 22, 24 | 6, — | 8, 9 | 15 d, 18 |
| | WT51386 | X,Y | 12, 13 | 11, — | 11, 12 | 17, — | 28, 29 | 17, 18 | 11 b, 12 | 9, 10 | 11, 14 d | 23, — | 9, 9.3 | 9, 11 | 19, — |
| | BC11352 | X,Y | 11, 13 | 13, — | 8, 12 | 13, 15 | 28, 30 d | 14, 17 | 10, 11 | 10, 12 e | 13, 14 | 24, — | 6, 9.3 | 8, — | 17, — |
| | MT97172 | X,Y | 11, 12 | 11, 12 | 9, 12 | 16, 18 | 29, 31 | 15 d, 15 j | 11, 12 b | 9, 12 | 13, 15 | 23, — | 7, — | 8, — | 16, 18 |
| | WA29584 | X,Y | 11, 12 | 11, 14 | 11, 12 | 16, — | 31.2, 32.2 | 17, 17 d | 9 b, 11 b | 8, 11 e | 11, 14 d | 22, 25 | 7, 9.3 | 8, 11 | 18, — |
| | WA29594 | X,Y | 11, 12 | 11, 12 | 11, — | 12, 15 | 30, 30.2 d | 17, 18 | 11, 12 | 7, 11 | 12, 13 | 22, 25 | 6, 9 | 8, — | 14 a, 14 g |
| | WA29612 | X,Y | 11, 12 | 11 c, 13 | 11, 12 | 12, 14 | 28, 30 d | 14, 17 d | 12, — | 11, 12 | 13, — | 22, 23.2 | 6, 9.3 | 8, 11 | 14 g, 19 |
| | ZT81387 | X,Y | 11, — | 9, 13 | 12, 13 | 16, 18 | 28, 32.2 | 18, — | 11 b, 11 | 10 e, 11 | 13, 15 | 21, 22 | 7, — | 6, 9 | 16, 19 |
| | MT94859 | X,Y | 10, 13 | 9, 11 | 9, 12 | 13, 17 | 29, 30 | 16, 17 d | 11, 13 b | 9, 11 e | 11, — | 20, 26 | 6, 9 | 8, 11 | 18, — |
| | MT94866 | X,Y | 11, 12 | 8, 12 c | 12, 13 | 12, 16 | 29.2 f, 30 | 15 d, — | 11, 12 | 10, 11 e | 12, 13 d | 22, 22.2 | 9.3, — | 8, 9 | 17, 20 e |
| | MT94868 | X,Y | 12, — | 9, 11 c | 9, 12 | 12, 17 | 27 f, 32.2 | 16 d, 17 d | 11, — | 8, 11 | 12, 14 | 20, 23 | 9.3, — | 8, 11 | 14 a, 16 |
| | MT94869 | X,Y | 12, — | 11 c, 12 | 12, 13 | 15, 19 | 28, 30 | 16, — | 11, 12 b | 10, 12 e | 13, 14 d | 20, 23 | 6, 9 | 8, — | 14 a, 17 d |
| | MT94875 | X,Y | 9, 10 | 11 c, 12 c | 12, — | 14, 16 | 29 d, 32.2 | 16 d, 18 | 11, 12 | 8, 9 | 8, 13 | 18, 25 | 6, — | 8, 12 | 16, 19 |
| African American | JT51471 | X,Y | 10, 13 | 12, — | 9, 13 | 16, — | 28, 33.2 | 15 d, 16 d | 11, — | 8, 10 | 12 f, 13 | 28 h, 31.2 | 6, 7 | 8, — | 16, — |
| | JT51499 | X,Y | 11, 12 | 11, — | 11, 12 | 13, 16 | 30 d, — | 15 d, 18 | 9 b, 12 | 10, 11 | 14, 14 d | 22, 26 | 7, 9.3 | 8, — | 16 d, 18 |
| | OT05888 | X,Y | 10, 11 | 11 c, 11 | 10, 13 | 16, 20 h | 31.2, 36 o | 15 d, 17 | 12 b, 13 b | 9, 11 | 13, 14 | 19, 20 | 7, 8 | 8, 11 | 16, 18 |
| | OT05890 | X,Y | 7, 8 | 10 c, 12 c | 11, 12 | 12, 18 | 30, 32.2 | 16 d, 17 | 11, 12 | 9, 10 | 16, — | 19, 24 | 7, 8 | 6, 11 | 16, 18 |
| | OT05892 | X,Y | 8, 11 | 12, — | 9, 12 | 13, 17 | 29, 34.1 e | 15 j, 18 d | 11 b, 11 | 10, — | 12 f, 14 | 23, 24 | 7, 8 | 9, 10 | 17, — |
| | OT05893 | X,Y | 11, — | 11 c, — | 10, 13 | 15, 17 | 28, 30 d | 15.2, 16 j | 10, 11 | 8, 12 | 13, 14 | 24, 26 | 7, 9 | 8, 9 | 16, 17 |
| | OT05894 | X,Y | 7, 10 | 12 c, 13 | 11, — | 13.2 h, 16 | 29, 37 k | 15 d, 15 j | 12, 13 b | 8, 12 | 14, 15 | 23, 25 | 7, — | 8, 11 | 19, — |
| | OT05896 | X,Y | 11, 12 | 12, — | 11, — | 18, — | 30 d, 30 | 15 j, 17 d | 11, 12 | 10, — | 14, 15 | 19, 25 | 8, 9 | 8, 10 | 15, 18 |
| | OT05897 | X,Y | 12, 13 | 11, 12 | 11, 13 | 15, 17 | 27, 30 d | 16, 18 | 12, — | 8, — | 13, — | 22, 23 | 7, 8 | 11, — | 16, 17 |
| | OT05898 | X,Y | 8, 11 | 12, 13 | 11, — | 17, — | 29, 32.2 | 14, 15 j | 8 b, 12 | 8, 13 | 13, 15 | 19, 22 | 8, 9 | 6, 9 | 15, 17 |
| | OT05899 | X,Y | 7, 11 | 12, — | 9, 11 | 15, 16 | 28, 32.2 | 13 d, 16 j | 8 b, 11 | 11, 12 | 13 d, 14 | 22, — | 7, — | 7, 10 | 16 d, 17 |
| | OT05901 | X,Y | 10, 11 | 8, 11 | 9, 10 | 18, — | 27 f, 28 | 15 j, 18 j | 11, 12 | 9, — | 13, 16 | 22, 23 | 7, — | 6, 11 | 18 o, 18 |
| | PT84214 | X,Y | 11, 12 | 12 c, 12 | 12, 13 | 12, 13.2 h | 28, 32.2 | 16 d, 17 d | 12, — | 10, — | 14, 15 | 21, 24 | 6, 8 | 10, 11 | 17, 17 d |
| | PT84215 | X,Y | 11, 12 | 12, — | 9, 11 | 15, 16 | 31.2, 32 f | 15 d, 16 j | 12 b, 12 | 8, 9 | 12 f, 14 | 22, — | 8, 11 | 8, 11 | 14 h, 16 |
| | PT84216 | X,Y | 10, — | 11, 12 | 12, 13 | 12, 16 | 30 d, — | 15 j, 16 j | 12, 13 b | 10, — | 13, 14 | 24, — | 7, 8 | 6, 8 | 13 m, 18 |
| | PT84222 | X,Y | 10, 12 | 12, 13 | 9, 10 | 15, 17 | 28, 30 d | 15 j, — | 12 b, 14 | 9, 11 | 12 f, 16 f | 23, 23.2 | 7, 8 | 9, 10 | 17, 18 |
| | PT84223 | X,Y | 12, — | 11 c, — | 11, 13 | 15, 19 | 29 f, 29 | 15 d, 17 | 11, 12 | 8, 10 | 14, 15 | 21, 22 | 7, — | 8, 11 | 16, 19 o |
| | PT84224 | X,Y | 10, 12 | 11 c, 12 | 8, 9 | 16, 17 | 30 d, 31 | 15, 16 j | 12, — | 10, — | 14, — | 22, 26 | 7, — | 11, — | 15, 17 |
| | PT84225 | X,Y | 10, 12 | 9, 11 c | 9, 12 | 15, 17 | 31, — | 17 d, 18 d | 12, — | 10, 11 | 13, — | 24, 25 | 7, — | 10, 12 | 14 a, 16 d |
| | PT84226 | X,Y | 11, 12 | 8, 12 c | 11, 12 | 17, — | 28, 32.2 | 11, 12 b | 10, — | 14, — | 23, 26 | 8, 9.3 | 8, 11 | 15 d, 18 |
| | PT84227 | X,Y | 8, 10 | 11 c, 12 | 9, 11 | 12, 22 | 31.2, 32.2 | 15 d, 17 d | 9 b, 12 b | 10, 11 | 12, 15 | 20, 22 | 6, 8 | 8, 9 | 15, 16 d |
| | PT84228 | X,Y | 11, 12 | 11 c, 12 | 11, — | 12, 20 h | 29, 30.2 | 15 d, 17 | 10, 12 | 8, 10 | 13 d, 14 | 24, 26 d | 7, 9 | 8, 10 | 16, 19 |
| | PT84230 | X,Y | 11, 12 | 11, 12 | 9, 13 | 13, 17 | 28, 29 f | 16 j, 17 j | 11, — | 9, 11 | 13, 14 | 19, 24 | 7, — | 8, — | 18, 20 f |
| | PT84231 | X,Y | 11, 12 | 12, — | 12, 13 | 14, 17 | 27 f, 29 | 15 j, 17 d | 8 b, 13 | 8, 9 | 14, 15 f | 22, 24 | 7, 9 | 8, 11 | 16 d, 18 |
| | PT84232 | X,Y | 9, 10 | 12 c, 13 | 11, 12 | 14, 20 h | 27, 28 | 15 j, 16 j | 9 b, 10 | 8, 10 | 13, 14 | 20, 25 | 7, — | 8, 9 | 15, 19 |
| | PT84234 | X,Y | 10, 12 | 13, — | 9, 11 | 15, 16 | 29, 31 | 15 j, 16 | 12, 13 | 10, 11 | 13 d, 15 | 19.2, 25 | 6, 7 | 6, — | 16, 16 d |
| | PT84236 | X,Y | 7, 12 | 12, 13 | 11, — | 12, 23 | 28, 29 | 16 d, 16 j | 12 b, 13 | 8, 9 | 12 f, 14 | 25, 26 | 7, — | 9, — | 14 h, 17 |
| | PT84239 | X,Y | 12, 13 | 12, 13 | 10, 11 | 15, 20 h | 30, 31 d | 15 j, 18 | 10, 12 | 11, — | 13, 14 | 23, 24 | 7, 8 | 9, — | 17, 18 |
| | PT84240 | X,Y | 10, 11 | 11 c, 12 | 12, 13 | 14, 19 | 28, 29 | 16 d, 17 j | 12 b, 12 | 9, 10 | 11, 13 | 23, 27 | 6, 9 | 9, 11 | 16, 17 |
| | PT84241 | X,Y | 12, 13 | 12, 13 | 11, 13 | 16, 17 | 29 f, 29 | 14, 18 | 11 b, 12 | 10, — | 10, 14 | 23, 25 | 6, 7 | 8, — | 18, — |
| | PT84242 | X,Y | 9, 10 | 12 c, 12 | 8, 11 | 12, 17 | 30 d, — | 16, 17 d | 11, 13 | 8, 11 | 13, — | 23, 25 | 7, 9.3 | 8, 9 | 14 a, 17 |
| | PT84243 | X,Y | 10, 12 | 11, 12 c | 10, 11 | 13, 16 | 28, 30 d | 15 d, 16 j | 13, 14 b | 10, 11 | 13, 14 | 23, 25 | 8, 9 | 6, — | 16 d, 17 | a A->G + 2T->2C
b G->T
c A->T
d G->A
e T->A
f A->G
g G->A + T->C
h T->C
i T->G
j 2G->2A
k 3A->3G
l G->A + C->T
m C->T
n C->G
o 2A->2G
p G->C

☐ One or both allele had a polymorphism

■ Both alleles were the same length, but differentiable by polymorphism(s)

* Exact nature of every observed polymorphism at loci D16S539, D18S51, D21S11, D3S1358 and FGA has not yet been confirmed independently with a mass tag or sequencing (some have been sequenced). Until final verification, there is a small chance that an observed G->A could be a T->C, for example. All polymorphisms at loci D13S317, D5S818, D7S820, D8S1179 and vWA have been confirmed using $^{13}$C-enriched dGTP.

Figure 15

| Sample | AMEL | CSF1PO | D13S317 | D16S539 | D18S51* | D21S11* | D3S1358* | D5S818 | D7S820 | D8S1179 | FGA* | THO1 | TPOX | vWA |
|---|---|---|---|---|---|---|---|---|---|---|---|---|---|---|
| GT37778 | X,Y | 10,12 | 9,13 | 10,12 | 14,20 | 28,30 j | 17 d,18 | 11,— | 9,12 | 14,— | 23,24 | 7,— | 9,11 | 18,38 |
| GT37812 | X,Y | 12,13 | 12,13 | 11,13 | 15,— | 29,32.2 | 14 8,16 | | 8,12 | | 22,— | 6,9.3 | 11,— | 15,16 |
| GT37828 | X,Y | 10,— | 9,14 | 9,11 | 14,17 | | 15 8,18 | 11,15 c | 11,12 | 10,15 | 22,23 | 7,— | 8,— | 16,18 |
| ZT80932 | X,Y | 12,13 | 10,11 | 11,13 | 17,18 | 29,32.2 | 14,17 a | 11,12 | 11,13 | 13,— | 23,24 | 8,9 | 9,— | 18,18 |
| GT37862 | X,Y | 10,11 | 8,12 | 10,11 | 11,16 | | 16,17 | 8 d,11 | 9,11 | 15,16 | 19,22 | 6,7 | 8,12 | 15,17 |
| GT37864 | X,Y | 12,— | 8,11 c | 10,12 | 13,15 | 29,— | 15 c,16 d | 11,12 | 9,12 p | 12,13 | 19,— | 7,— | 8,— | 16,— |
| GT37869 | X,Y | 10,11 | 11,12 | 9,12 | 15,16 | 30,31.2 | 16 8,17 d | 7,12 | 10,11 | | 24,25 | 6,7 | 8,11 | |
| GT37898 | X,Y | 10,12 | 11,12 | 9,13 | 17,19 | 30 a,30.2 | 13,15 a | 12,— | 10 a,11 | 14,15 | 23,25 | 7,9 | 8,— | 13 a,17 |
| GT37900 | X,Y | 11,12 | 11,12 | 10,12 | 12,13 | 29,31.2 | 14,17 | 11,— | 9,11 | 13,14 d | 23,26 | 6,7 | 11,— | 17,19 |
| GT37913 | X,Y | 11,12 | 11,— | 11,— | 13,15 | 29,31 d | 16,17 d | 7,11 | 10,13 | 12,13 | 19,22 | 6,9.3 | 8,11 | 16,17 |
| JT52076 | X,Y | 12,— | 8,— | 11,12 | 16,21 | 30,32.2 | 15 d,16 | 11,— | 11,12 | 12,14 | 21,22 | 8,9.3 | 8,11 | 15,18 |
| OT07280 | X,Y | 10,12 | 9,13 | 12,13 | 13,14 | | 15,16 d | 7,12 | 8,11 | 12,13 | 22,24 | 7,8 | 8,— | 17,20 |
| PT85612 | X,Y | 10,12 | | 12,— | 14,17 | 29,— | 16 d,16 d | 7,10 | | | 21,24 | 7,8 | 12,— | 18,38 |
| PT85658 | X,Y | 12,14 | 9 c,14 | 12,13 | 14,15 | 30,— | 16,17 | 16 d,13 | 10,11 | 10,12 | 19,23 | 6,7 | 8,9 | 18,19 |
| TT51399 | X,Y | 10,12 | 10 c,— | 10,11 | 12,13 | 29,32.2 d | | 7,11 | 11,12 a | | 25,27 | 6,7 | 8,12 | 16,18 |
| TT51407 | X,Y | 10,— | 8,12 c | 11,13 | 12,19 | 30,30 d | 18,— | 11,— | 10 a,11 | 10,11 | 22,23 | 7,— | 8,11 | 18 a,38 |
| TT51422 | X,Y | 10,12 | 9,15 c | 13,— | 15,18 | 28,31 d | 16,17 | 11,13 | 10,12 | 11,14 | 20,24 | 6,8 | 8,11 | 18,28 |
| TT51435 | X,Y | 9,12 | 9,11 e | 11,14 | 12,17 | 28,30.2 | 15 8,16 p | 11,11 | 10,12 | 13,26 | 7,9.3 | 8,9 | 16,17 |
| TT51483 | X,Y | 11,— | | 11,— | 18,19 | 30 8,35 | 14 8,16 | | 8,10 | 13,15 | 21,26 | 9,9.3 | 9,10 | 14 a,18 |
| TT51511 | X,Y | 11,12 | 9,— | 11,12 | 13,22 | 30 8,33.2 | 15 d,17 | 12,— | 8,10 e | 12,14 | 20,25 | 7,— | 11,— | 15,16 |
| TT51530 | X,Y | 10,11 | 8,13 c | 10,13 | 13,15 | 31,31.2 | 15 d,18 | 11,12 | 10,11 | 12,13,18 | 23,26 | 7,9.3 | 11,12 | 16,18 |
| ZT80731 | X,Y | 10,11 | 11,12 | 12,13 | 13,15 | 30 8,30.2 | 14,16 | 11,13 | 10,— | 11,13 | 18,24 | 9.3,— | 8,11 | 15,17 |
| ZT80737 | X,Y | 11,13 | 12,13 | 9,12 | 12,16 | 29,30.2 | | 12,— | 10,— | 14,15 | 21,— | 9.3,— | 9,12 | 16,17 |
| ZT80762 | X,Y | 12,— | 8,10 c | 13,— | 14,15 | 30 8,32.2 8 | 15 c,— | 11,— | 11,— | 10 a,11 | 21,23 | 8,9 | 8,12 | 17,18 |
| ZT80786 | X,Y | 10,11 | 8,12 c | 9,— | 15,16 | 29 d,30 | 15 d,18 | 11,12 | 9,11 | 13,15 | 20,23 | 7,8 | 11,12 | 18,30 |
| ZT80815 | X,Y | 10,13 | 13,15 c | 10,12 | 14,16 | 28,29 d | 14,16 d | 10,11 | 11,12 | 13,— | 24,— | 7,8 | 10,11 | 16 d,17 |
| ZT80826 | X,Y | 10,12 | 10,12 | 9,11 | 12,18 | 28,31.2 | 17,18 d | 8 d,12 | 10,12 8 | 11,7 d | 21,— | 9.3,— | 8,— | |
| ZT80863 | X,Y | 11,12 | 8,12 | 11,12 | 14,— | 29,— | 15 d,17 | 11,12 | 10,11 | 10,15 | 23,26 | 9.3,— | 8,— | 17,18 |
| ZT80865 | X,Y | 10,12 | 8,11 | 13,— | 16,17 | 29,31.2 | 15 d,17 | 11,14 | 9,11 | 13 d,15 | 21,23 | 7,9.3 | 8,— | 17,19 |
| ZT80868 | X,Y | 11,12 | 9,11 c | 12,13 | 15,16 | 30,32.2 | 14,15 d | 11,15 | 9,10 | 14,— | 20,22 | 6,9 | 11,12 | 16 d,17 |
| ZT80870 | X,Y | 11,12 | 8,13 c | 11,12 | 13,20 | 29,34 | 17,18 | 12 d,13 | 8,— | 11,14 | 21,23 | 6,9 | 8,12 | 15 d,38 |
| ZT80925 | X,Y | 10,11 | 11,14 | 12,— | 17,— | 27,30 d | 15 d,17 | 11,13 | 8,— | 16,18 | 18,21 | 7,— | 8,11 | |

Hispanic a A->G + 2T->2C
b G->T
c A->T
d G->A
e T->A
f A->G
g G->A + T->C
h T->C
i T->G
j 2C->2A
k 3A->3G
l G->A + C->T
m C->T
n C->G
o 2A->2G
p G->C ▨ One or both allele had a polymorphism ▮ Both alleles were the same length, but differentiable by polymorphism(s)

* Exact nature of every observed polymorphism at loci D16S539, D18S51, D21S11, D3S1358 and FGA has not yet been confirmed independently with a mass tag or sequencing (some have been sequenced). Until final verification, there is a small chance that an observed G->A could be a T->C, for example. All polymorphisms at loci D13S317, D5S818, D7S820, D8S1179 and vWA have been confirmed using $^{13}$C-enriched dGTP.

Figure 18
No mass tag used
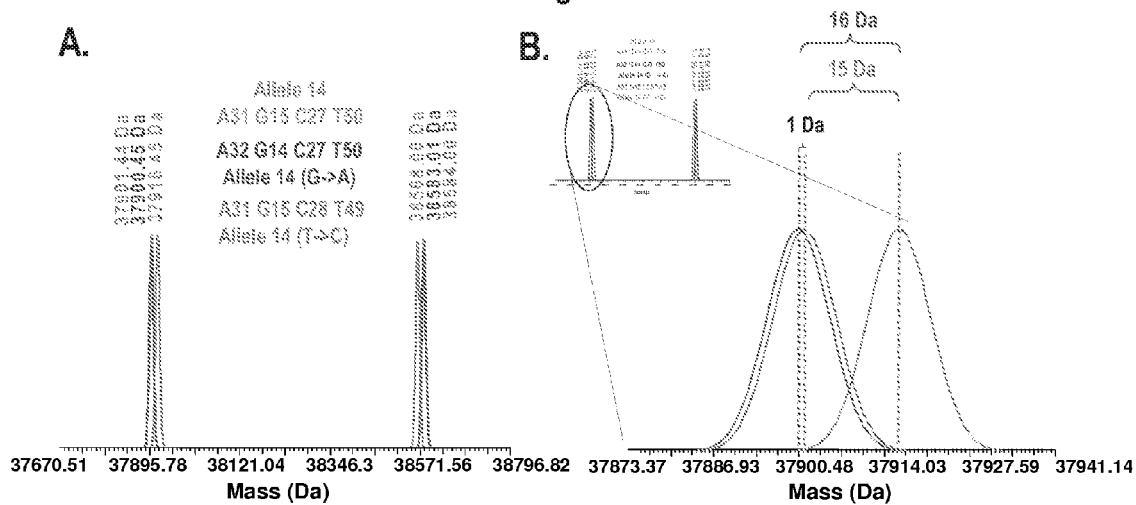
$^{13}$C-dGTP mass tag used
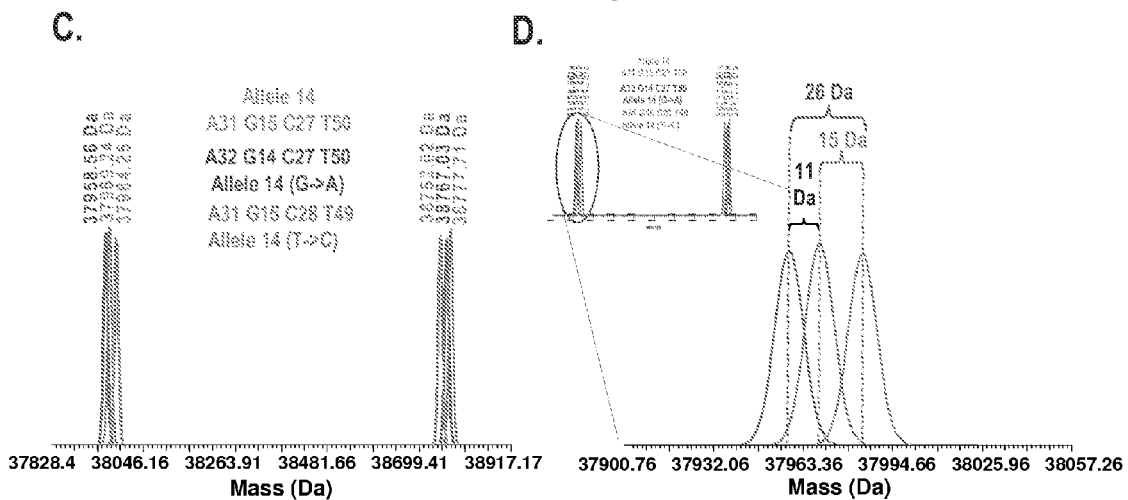

SEQUENCE LISTING

<160> NUMBER OF SEQ ID NOS: 124

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
tggggagaat aatcagtatg tgacttggat tg                              32

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
tctagtggat gataagaata atcagtatgt gacttgg                         37

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
tgccctagtg gatgataaga ataatcagta tgtg                            34

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
ggggagaata atcagtatgt gacttggatt g                               31

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tggcacagaa caggcactta ggga                                       24

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
tactggcaca gaacaggcac ttagg                                      25

<210> SEQ ID NO 7
<211> LENGTH: 23
<212> TYPE: DNA
<213> ORGANISM: Artificial Sequence

```
<220> FEATURE:
<223> OTHER INFORMATION: Primer

<400> SEQUENCE: 7
ggcacagaac aggcacttag gga                                              23

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
tgattcccat tggcctgttc ctcc                                             24

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tattcaaagg gtatctgggc tctgg                                            25

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
ggaaatcaaa gggtatctgg gctctgg                                          27

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
tcccttaggc atatttacaa gctag                                            25

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
tccccaaaat aaaattaggc atatttacaa gctag                                 35

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
tgtgagtcaa ttccccaag                                                   19
```

```
<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
tgagtcaatt ccccaagtga attgc                                           25

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
tgtggagatg tcttacaata acagttgcta cta                                  33

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
ttctctggtg tgtggagatg tcttaca                                         27

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
tcccaagctc ttcctcttcc ctagatc                                         27

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
tcttcctctt ccctagatca atacagacag                                      30

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
tgcagatccc aagctcttcc tcttc                                           25

<210> SEQ ID NO 20
<211> LENGTH: 28
<212> TYPE: DNA
<213> ORGANISM: Artificial Sequence
<220> FEATURE:
<223> OTHER INFORMATION: Primer
```

-continued

```
<400> SEQUENCE: 20
tagctcttcc tcttccctag atcaatac                                           28

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
gctcttcctc ttccctagat caatacagac a                                       31

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
tggactctga cccatctaac gcctatct                                           28

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
tctgacccat ctaacgccta tctgtattta c                                       31

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
tcatctaacg cctatctgta tttacaaata c                                       31

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
tggactctga cccatctaac gcctatc                                            27

<210> SEQ ID NO 26
<211> LENGTH: 32
<212> TYPE: DNA
<213> ORGANISM: Artificial Sequence
<220> FEATURE:
<223> OTHER INFORMATION: Primer

<400> SEQUENCE: 26
tcccatctaa cgcctatctg tatttacaaa ta                                      32

<210> SEQ ID NO 27
```

```
<211> LENGTH: 32
<212> TYPE: DNA
<213> ORGANISM: Artificial Sequence
<220> FEATURE:
<223> OTHER INFORMATION: Primer

<400> SEQUENCE: 27
ctctgaccca tctaacgcct atctgtattt ac                                    32

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
tttttgtatt tcatgtgtac attcg                                            25

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
tccctgtatt tcatgtgtac attcg                                            25

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
tcccttgtat ttcatgtgta cattcg                                           26

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
ggggttttgt atttcatgtg tacattcgta tc                                    32

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
tagaacactt gtcatagttt agaacgaac                                        29

<210> SEQ ID NO 33
<211> LENGTH: 34
<212> TYPE: DNA
<213> ORGANISM: Artificial Sequence
<220> FEATURE:
<223> OTHER INFORMATION: Primer

<400> SEQUENCE: 33
```

-continued tggaacactt gtcatagttt agaacgaact aacg                            34

<210> SEQ ID NO 34
<211> LENGTH: 29
<212> TYPE: DNA
<213> ORGANISM: Artificial Sequence
<220> FEATURE:
<223> OTHER INFORMATION: Primer

<400> SEQUENCE: 34
tgatagaaca cttgtcatag tttagaacg                                  29

<210> SEQ ID NO 35
<211> LENGTH: 31
<212> TYPE: DNA
<213> ORGANISM: Artificial Sequence
<220> FEATURE:
<223> OTHER INFORMATION: Primer

<400> SEQUENCE: 35
gggaacactt gtcatagttt agaacgaact a                               31

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
tgacaagggt gattttcctc tttggtatcc                                 30

<210> SEQ ID NO 37
<211> LENGTH: 33
<212> TYPE: DNA
<213> ORGANISM: Artificial Sequence
<220> FEATURE:
<223> OTHER INFORMATION: Primer

<400> SEQUENCE: 37
tggtgatttt cctctttggt atccttatgt aat                             33

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
tggtgatttt cctctttggt atcc                                       24

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39 tgggtgatttt tcctctttgg tatcc                                     25

<210> SEQ ID NO 40
<211> LENGTH: 33
<212> TYPE: DNA

```
<213> ORGANISM: Artificial Sequence
<220> FEATURE:
<223> OTHER INFORMATION: Primer

<400> SEQUENCE: 40
gggtgatttt cctctttggt atccttatgt aat                                33

<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
tcatgaaatc aacagaggct tgcatg                                        26

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
tactcatgaa atcaacagag gcttgca                                       27

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
tccctgtgtc tcagttttcc tacctg                                        26

<210> SEQ ID NO 44
<211> LENGTH: 31
<212> TYPE: DNA
<213> ORGANISM: Artificial Sequence
<220> FEATURE:
<223> OTHER INFORMATION: Primer

<400> SEQUENCE: 44
tgggatgaag atattaacag taactgcctt c                                  31

<210> SEQ ID NO 45
<211> LENGTH: 36
<212> TYPE: DNA
<213> ORGANISM: Artificial Sequence
<220> FEATURE:
<223> OTHER INFORMATION: Primer

<400> SEQUENCE: 45
tcagttttcc tacctgtaaa atgaagatat taacag                             36

<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
taaccaccct gtgtctcagt tttcctacc                                     29
```

```
<210> SEQ ID NO 47
<211> LENGTH: 33
<212> TYPE: DNA
<213> ORGANISM: Artificial Sequence
<220> FEATURE:
<223> OTHER INFORMATION: Primer

<400> SEQUENCE: 47
ggcatgaaga tattaacagt aactgccttc ata                              33

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
tgccctgggc tctgtaaaga atagtg                                      26

<210> SEQ ID NO 49
<211> LENGTH: 26
<212> TYPE: DNA
<213> ORGANISM: Artificial Sequence
<220> FEATURE:
<223> OTHER INFORMATION: Primer

<400> SEQUENCE: 49
taacaatgcc ctgggctctg taaaga                                      26

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
tgccctgggc tctgtaaaga atagt                                       25

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
gccctgggct ctgtaaagaa tagtg                                       25

<210> SEQ ID NO 52
<211> LENGTH: 35
<212> TYPE: DNA
<213> ORGANISM: Artificial Sequence
<220> FEATURE:
<223> OTHER INFORMATION: Primer

<400> SEQUENCE: 52
tgggtgataa atacatagga tggatggata gatgg                            35

<210> SEQ ID NO 53
<211> LENGTH: 36
<212> TYPE: DNA
<213> ORGANISM: Artificial Sequence
<220> FEATURE:
```

<223> OTHER INFORMATION: Primer

<400> SEQUENCE: 53
taggacagat gataaataca taggatggat ggatag          36

<210> SEQ ID NO 54
<211> LENGTH: 32
<212> TYPE: DNA
<213> ORGANISM: Artificial Sequence
<220> FEATURE:
<223> OTHER INFORMATION: Primer

<400> SEQUENCE: 54
tgggacagat gataaataca taggatggat gg              32

<210> SEQ ID NO 55
<211> LENGTH: 34
<212> TYPE: DNA
<213> ORGANISM: Artificial Sequence
<220> FEATURE:
<223> OTHER INFORMATION: Primer

<400> SEQUENCE: 55
gggtgataaa tacataggat ggatggatag atgg            34

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
taggcccttc tgtccttgtc agc                        23

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
tctgtccttg tcagcgttta tttgcc                     26

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
tgtgcgctgg tcttactcct gttc                       24

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
tcccaggtct tctgaacaca agtcg                      25

```
<210> SEQ ID NO 60
<211> LENGTH: 26
<212> TYPE: DNA
<213> ORGANISM: Artificial Sequence
<220> FEATURE:
<223> OTHER INFORMATION: Primer

<400> SEQUENCE: 60
ggtgtccttg tcagcgttta tttgcc                                          26

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
tgcaggtcac agggaacaca gac                                             23

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
tgtgggctga aaagctcccg attat                                           25

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
tccgagtgca ggtcacaggg a                                               21

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
tcacagggaa cacagactcc atgg                                            24

<210> SEQ ID NO 65
<211> LENGTH: 24
<212> TYPE: DNA
<213> ORGANISM: Artificial Sequence
<220> FEATURE:
<223> OTHER INFORMATION: Primer

<400> SEQUENCE: 65
tcaggtcaca gggaacacag actc                                            24

<210> SEQ ID NO 66
<211> LENGTH: 22
<212> TYPE: DNA
<213> ORGANISM: Artificial Sequence
<220> FEATURE:
<223> OTHER INFORMATION: Primer
```

```
<400> SEQUENCE: 66
tacacagggc ttccgagtgc ag                                              22

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
cgctggtcac agggaacaca gac                                             23

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
tgatttgtct gtaattgcca gc                                              22

<210> SEQ ID NO 69
<211> LENGTH: 26
<212> TYPE: DNA
<213> ORGANISM: Artificial Sequence
<220> FEATURE:
<223> OTHER INFORMATION: Primer

<400> SEQUENCE: 69
tgagtgattt gtctgtaatt gccagc                                          26

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
tatgttgtat tagtcaatgt tctcc                                           25

<210> SEQ ID NO 71
<211> LENGTH: 33
<212> TYPE: DNA
<213> ORGANISM: Artificial Sequence
<220> FEATURE:
<223> OTHER INFORMATION: Primer

<400> SEQUENCE: 71
tccctaaaga tgttgtatta gtcaatgttc tcc                                  33

<210> SEQ ID NO 72
<211> LENGTH: 28
<212> TYPE: DNA
<213> ORGANISM: Artificial Sequence
<220> FEATURE:
<223> OTHER INFORMATION: Primer

<400> SEQUENCE: 72
tctgagtgac aaaattgagac cttgtctc                                       28

<210> SEQ ID NO 73
<211> LENGTH: 29
```

<212> TYPE: DNA
<213> ORGANISM: Artificial Sequence
<220> FEATURE:
<223> OTHER INFORMATION: Primer

<400> SEQUENCE: 73
ttcactctga gtgacaaatt gagaccttg                                   29

<210> SEQ ID NO 74
<211> LENGTH: 35
<212> TYPE: DNA
<213> ORGANISM: Artificial Sequence
<220> FEATURE:
<223> OTHER INFORMATION: Primer

<400> SEQUENCE: 74
tgcatctgta agcatgtatc tatcatccat ctctg                            35

<210> SEQ ID NO 75
<211> LENGTH: 30
<212> TYPE: DNA
<213> ORGANISM: Artificial Sequence
<220> FEATURE:
<223> OTHER INFORMATION: Primer

<400> SEQUENCE: 75
taccatccat ctctgttttg tctttcaatg                                  30

<210> SEQ ID NO 76
<211> LENGTH: 36
<212> TYPE: DNA
<213> ORGANISM: Artificial Sequence
<220> FEATURE:
<223> OTHER INFORMATION: Primer

<400> SEQUENCE: 76
tggatctatc atccatctct gttttgtctt tcaatg                           36

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
tcatccatct ctgttttgtc tttcaatg                                    28

<210> SEQ ID NO 78
<211> LENGTH: 32
<212> TYPE: DNA
<213> ORGANISM: Artificial Sequence
<220> FEATURE:
<223> OTHER INFORMATION: Primer

<400> SEQUENCE: 78
gctaccatcc atctctgttt tgtctttcaa tg                               32

<210> SEQ ID NO 79
<211> LENGTH: 25
<212> TYPE: DNA
<213> ORGANISM: Artificial Sequence
<220> FEATURE:
<223> OTHER INFORMATION: Primer

<400> SEQUENCE: 79
tgagccatag gcagcccaaa aagac                                          25

<210> SEQ ID NO 80
<211> LENGTH: 24
<212> TYPE: DNA
<213> ORGANISM: Artificial Sequence
<220> FEATURE:
<223> OTHER INFORMATION: Primer

<400> SEQUENCE: 80
taggcagccc aaaaagacag acag                                           24

<210> SEQ ID NO 81
<211> LENGTH: 21
<212> TYPE: DNA
<213> ORGANISM: Artificial Sequence
<220> FEATURE:
<223> OTHER INFORMATION: Primer

<400> SEQUENCE: 81
tcagcccaaa aagacagaca g                                              21

<210> SEQ ID NO 82
<211> LENGTH: 26
<212> TYPE: DNA
<213> ORGANISM: Artificial Sequence
<220> FEATURE:
<223> OTHER INFORMATION: Primer

<400> SEQUENCE: 82
taggcagccc aaaaagacag acagaa                                         26

<210> SEQ ID NO 83
<211> LENGTH: 23
<212> TYPE: DNA
<213> ORGANISM: Artificial Sequence
<220> FEATURE:
<223> OTHER INFORMATION: Primer

<400> SEQUENCE: 83
tgagccatag gcagcccaaa aag                                            23

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
gtaggcagcc caaaaagaca gacag                                          25

<210> SEQ ID NO 85
<211> LENGTH: 25
<212> TYPE: DNA
<213> ORGANISM: Artificial Sequence
<220> FEATURE:
<223> OTHER INFORMATION: Primer

<400> SEQUENCE: 85
tatcctgtag attattttca ctgtg                                          25

<210> SEQ ID NO 86
<211> LENGTH: 29
<212> TYPE: DNA
<213> ORGANISM: Artificial Sequence

```
<220> FEATURE:
<223> OTHER INFORMATION: Primer

<400> SEQUENCE: 86
tccctatcct gtagattatt ttcactgtg                                29

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
tacctatcct gtagattatt ttcactgtgg                               30

<210> SEQ ID NO 88
<211> LENGTH: 33
<212> TYPE: DNA
<213> ORGANISM: Artificial Sequence
<220> FEATURE:
<223> OTHER INFORMATION: Primer

<400> SEQUENCE: 88
gggtacctat cctgtagatt attttcactg tgg                           33

<210> SEQ ID NO 89
<211> LENGTH: 28
<212> TYPE: DNA
<213> ORGANISM: Artificial Sequence
<220> FEATURE:
<223> OTHER INFORMATION: Primer

<400> SEQUENCE: 89
tcattgacag aattgcacca aatattgg                                 28

<210> SEQ ID NO 90
<211> LENGTH: 30
<212> TYPE: DNA
<213> ORGANISM: Artificial Sequence
<220> FEATURE:
<223> OTHER INFORMATION: Primer

<400> SEQUENCE: 90
tcgggtgttt actatagact atttagtgag                               30

<210> SEQ ID NO 91
<211> LENGTH: 33
<212> TYPE: DNA
<213> ORGANISM: Artificial Sequence
<220> FEATURE:
<223> OTHER INFORMATION: Primer

<400> SEQUENCE: 91
tggccgggtg tttactatag actatttagt gag                           33

<210> SEQ ID NO 92
<211> LENGTH: 32
<212> TYPE: DNA
<213> ORGANISM: Artificial Sequence
<220> FEATURE:
<223> OTHER INFORMATION: Primer

<400> SEQUENCE: 92
tcagaattgc accaaatatt ggtaattaaa tg                            32
```

<210> SEQ ID NO 93
<211> LENGTH: 34
<212> TYPE: DNA
<213> ORGANISM: Artificial Sequence
<220> FEATURE:
<223> OTHER INFORMATION: Primer

<400> SEQUENCE: 93
cccggaatgt ttactataga ctatttagtg agat                                    34

<210> SEQ ID NO 94
<211> LENGTH: 34
<212> TYPE: DNA
<213> ORGANISM: Artificial Sequence
<220> FEATURE:
<223> OTHER INFORMATION: Primer

<400> SEQUENCE: 94
tccaatcata gccacagttt acaacatttg tatc                                    34

<210> SEQ ID NO 95
<211> LENGTH: 30
<212> TYPE: DNA
<213> ORGANISM: Artificial Sequence
<220> FEATURE:
<223> OTHER INFORMATION: Primer

<400> SEQUENCE: 95
tggtcatagc cacagtttac aacatttgta                                         30

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
tagccacagt ttacaacatt tgtatct                                            27

<210> SEQ ID NO 97
<211> LENGTH: 29
<212> TYPE: DNA
<213> ORGANISM: Artificial Sequence
<220> FEATURE:
<223> OTHER INFORMATION: Primer

<400> SEQUENCE: 97
tcatagccac agtttacaac atttgtatc                                          29

<210> SEQ ID NO 98
<211> LENGTH: 32
<212> TYPE: DNA
<213> ORGANISM: Artificial Sequence
<220> FEATURE:
<223> OTHER INFORMATION: Primer

<400> SEQUENCE: 98
gccaatcata gccacagttt acaacatttg ta                                      32

<210> SEQ ID NO 99
<211> LENGTH: 23
<212> TYPE: DNA
<213> ORGANISM: Artificial Sequence
<220> FEATURE:
<223> OTHER INFORMATION: Primer -continued

<400> SEQUENCE: 99
tgacagagca agaccctgtc tca                                            23

<210> SEQ ID NO 100
<211> LENGTH: 22
<212> TYPE: DNA
<213> ORGANISM: Artificial Sequence
<220> FEATURE:
<223> OTHER INFORMATION: Primer

<400> SEQUENCE: 100
tgtgacagag caagaccctg tc                                             22

<210> SEQ ID NO 101
<211> LENGTH: 22
<212> TYPE: DNA
<213> ORGANISM: Artificial Sequence
<220> FEATURE:
<223> OTHER INFORMATION: Primer

<400> SEQUENCE: 101
tgggtgacag agcaagaccc tg                                             22

<210> SEQ ID NO 102
<211> LENGTH: 24
<212> TYPE: DNA
<213> ORGANISM: Artificial Sequence
<220> FEATURE:
<223> OTHER INFORMATION: Primer

<400> SEQUENCE: 102
tgcacacttg gacagcattt cctg                                           24

<210> SEQ ID NO 103
<211> LENGTH: 27
<212> TYPE: DNA
<213> ORGANISM: Artificial Sequence
<220> FEATURE:
<223> OTHER INFORMATION: Primer

<400> SEQUENCE: 103
tcctgtgtca gaccctgttc taagtac                                        27

<210> SEQ ID NO 104
<211> LENGTH: 28
<212> TYPE: DNA
<213> ORGANISM: Artificial Sequence
<220> FEATURE:
<223> OTHER INFORMATION: Primer

<400> SEQUENCE: 104
gtgtcagacc ctgttctaag tacttcct                                       28

<210> SEQ ID NO 105
<211> LENGTH: 27
<212> TYPE: DNA
<213> ORGANISM: Artificial Sequence
<220> FEATURE:
<223> OTHER INFORMATION: Primer

<400> SEQUENCE: 105
tccatcagag cttaaactgg gaagctg                                        27

<210> SEQ ID NO 106

```
<211> LENGTH: 27
<212> TYPE: DNA
<213> ORGANISM: Artificial Sequence
<220> FEATURE:
<223> OTHER INFORMATION: Primer

<400> SEQUENCE: 106
tggtggtagg aactgtaaaa tcaggac                                        27

<210> SEQ ID NO 107
<211> LENGTH: 27
<212> TYPE: DNA
<213> ORGANISM: Artificial Sequence
<220> FEATURE:
<223> OTHER INFORMATION: Primer

<400> SEQUENCE: 107
tggtaggaac tgtaaaatca ggaccac                                        27

<210> SEQ ID NO 108
<211> LENGTH: 26
<212> TYPE: DNA
<213> ORGANISM: Artificial Sequence
<220> FEATURE:
<223> OTHER INFORMATION: Primer

<400> SEQUENCE: 108
gcatcagagc ttaaactggg aagctg                                         26

<210> SEQ ID NO 109
<211> LENGTH: 21
<212> TYPE: DNA
<213> ORGANISM: Artificial Sequence
<220> FEATURE:
<223> OTHER INFORMATION: Primer

<400> SEQUENCE: 109
ccccaagtga attgccttct a                                              21

<210> SEQ ID NO 110
<211> LENGTH: 23
<212> TYPE: DNA
<213> ORGANISM: Artificial Sequence
<220> FEATURE:
<223> OTHER INFORMATION: Primer

<400> SEQUENCE: 110
ccccaagtga attgccttct atc                                            23

<210> SEQ ID NO 111
<211> LENGTH: 25
<212> TYPE: DNA
<213> ORGANISM: Artificial Sequence
<220> FEATURE:
<223> OTHER INFORMATION: Primer

<400> SEQUENCE: 111
gcccttaggc atatttacaa gctag                                          25

<210> SEQ ID NO 112
<211> LENGTH: 28
<212> TYPE: DNA
<213> ORGANISM: Artificial Sequence
<220> FEATURE:
<223> OTHER INFORMATION: Primer

<400> SEQUENCE: 112
```
cccaattagg catatttaca agctagtt                                          28

<210> SEQ ID NO 113
<211> LENGTH: 32
<212> TYPE: DNA
<213> ORGANISM: Artificial Sequence
<220> FEATURE:
<223> OTHER INFORMATION: Primer

<400> SEQUENCE: 113
gatgtcttac aataacagtt gctactattt ct                                     32

<210> SEQ ID NO 114
<211> LENGTH: 32
<212> TYPE: DNA
<213> ORGANISM: Artificial Sequence
<220> FEATURE:
<223> OTHER INFORMATION: Primer

<400> SEQUENCE: 114
gtggagatgt cttacaataa cagttgctac ta                                     32

<210> SEQ ID NO 115
<211> LENGTH: 25
<212> TYPE: DNA
<213> ORGANISM: Artificial Sequence
<220> FEATURE:
<223> OTHER INFORMATION: Primer

<400> SEQUENCE: 115
ctcatgaaat caacagaggc ttgca                                             25

<210> SEQ ID NO 116
<211> LENGTH: 25
<212> TYPE: DNA
<213> ORGANISM: Artificial Sequence
<220> FEATURE:
<223> OTHER INFORMATION: Primer

<400> SEQUENCE: 116
gaaatcaaca gaggcttgca tgtat                                             25

<210> SEQ ID NO 117
<211> LENGTH: 30
<212> TYPE: DNA
<213> ORGANISM: Artificial Sequence
<220> FEATURE:
<223> OTHER INFORMATION: Primer

<400> SEQUENCE: 117
ggtagataga ctggatagat agacgataga                                        30

<210> SEQ ID NO 118
<211> LENGTH: 29
<212> TYPE: DNA
<213> ORGANISM: Artificial Sequence
<220> FEATURE:
<223> OTHER INFORMATION: Primer

<400> SEQUENCE: 118
ggtagataga ctggatagat agacgatag                                         29

<210> SEQ ID NO 119
<211> LENGTH: 23
<212> TYPE: DNA

```
<213> ORGANISM: Artificial Sequence
<220> FEATURE:
<223> OTHER INFORMATION: Primer

<400> SEQUENCE: 119
gtgatttgtc tgtaattgcc agc                                            23

<210> SEQ ID NO 120
<211> LENGTH: 26
<212> TYPE: DNA
<213> ORGANISM: Artificial Sequence
<220> FEATURE:
<223> OTHER INFORMATION: Primer

<400> SEQUENCE: 120
gtctgtaatt gccagcaaaa aagaaa                                         26

<210> SEQ ID NO 121
<211> LENGTH: 25
<212> TYPE: DNA
<213> ORGANISM: Artificial Sequence
<220> FEATURE:
<223> OTHER INFORMATION: Primer

<400> SEQUENCE: 121
ctgagtgaca aattgagacc ttgtc                                          25

<210> SEQ ID NO 122
<211> LENGTH: 29
<212> TYPE: DNA
<213> ORGANISM: Artificial Sequence
<220> FEATURE:
<223> OTHER INFORMATION: Primer

<400> SEQUENCE: 122
ctctgagtga caaattgaga ccttgtctc                                      29

<210> SEQ ID NO 123
<211> LENGTH: 22
<212> TYPE: DNA
<213> ORGANISM: Artificial Sequence
<220> FEATURE:
<223> OTHER INFORMATION: Primer

<400> SEQUENCE: 123
ggtgacagag caagaccctg tc                                             22

<210> SEQ ID NO 124
<211> LENGTH: 23
<212> TYPE: DNA
<213> ORGANISM: Artificial Sequence
<220> FEATURE:
<223> OTHER INFORMATION: Primer

<400> SEQUENCE: 124
gacagagcaa gaccctgtct cat                                            23
```

METHODS FOR RAPID FORENSIC DNA ANALYSIS

PRIORITY STATEMENT

This application is a U.S. National Phase application under 35 U.S.C. §371 claiming priority to International Application Number PCT/US2008/054926 filed on Feb. 25, 2008 under the Patent Cooperation Treaty, which claims priority to U.S. Provisional Patent Application Ser. No. 60/891,479 filed Feb. 23, 2007 and U.S. Provisional Patent Application Ser. No. 60/941,641 filed Jun. 1, 2007, each of which is herein incorporated by reference in its entirety.

STATEMENT OF GOVERNMENT SUPPORT

This invention was made with United States Government support under NIJ grant 2006-DN-BX-K011. The United States Government may have certain rights in the invention.

SEQUENCE LISTING

The present application is being filed along with a Sequence Listing in electronic format. The Sequence Listing is provided as a file entitled DIBIS0091WOSEQ.txt, created Feb. 22, 2008 which is 24 Kb in size. The information in the electronic format of the sequence listing is incorporated herein by reference in its entirety.

FIELD OF THE INVENTION

This invention relates to the fields of genetic mapping and genetic identity testing, including of forensic testing and paternity testing. The invention specifically relates to use of amplification and mass spectrometry in DNA analysis using tandem repeat regions of DNA. The invention enables rapid and accurate forensic analysis by using mass spectrometry to characterize informative regions of DNA.

BACKGROUND OF THE INVENTION

The process of human identification through DNA analysis is a common objective of forensics investigations. As used herein, "forensics" is the study of evidence, for example, that discovered at a crime or accident scene that is then used in a court of law. "Forensic science" is any science used to answer questions of interest to the legal system, in particular the criminal or civil justice system, providing impartial scientific evidence for use in the courts of law, for example, in criminal investigations and trials. Forensic science is a multidisciplinary subject, drawing principally from chemistry and biology, but also from physics, geology, psychology and social science, for example. The goal of one aspect of human forensics, forensic DNA typing, is to determine the identity or genotype of DNA acquired from a forensic sample, for example, evidence from a crime scene or DNA sample from an individual. Typical sources of such DNA evidence include hair, bones, teeth, and body fluids such as saliva, semen, and blood. There often exists a need for rapid identification of a large number of humans, human remains and/or biological samples. Such remains or samples may be associated with war-related casualties, aircraft crashes, and acts of terrorism, for example.

Tandem DNA repeat regions, which are prevalent in the human genome and exhibit a high degree of variability among individuals, are used in a number of fields, including human forensics and identity testing, genetic mapping, and linkage analysis. Various types of DNA repeat regions exist within eukaryotic genomes and can be classified based on length of their core repeat regions. Short tandem repeats (STRs), also called simple sequence repeats (SSRs), or microsatellites are repeat regions having core units of between 2-6 nucleotides in length. For a particular STR locus, individuals in a population differ in the number of these core repeat units.

STR typing involves the amplification of multiple STR DNA loci that display a collection of alleles in the human population that differ in repeat number. Typically, the products of such amplification reactions are analyzed by polyacrylamide gel or capillary electrophoresis using fluorescent detection methods, and subsequent discrimination among different alleles based on amplification product length. Because a typical STR typing analysis will use multiple STR loci that are not genetically linked, the product rule can be applied to estimate the probability of a random match to any STR profile where population allele frequencies have been characterized for each loci (Holt C L, et. al. (2000) *Forensic Sci. Int.* 112(2-3): 91-109; Holland M M, et. al. (2003) *Croat. Med. J.* 44(3): 264-72), leading to extremely high differentiation power with low random match probabilities within the human population. Because of the short length of STR repeats and the high degree of variability in number of repeats among individuals in a population, STR typing has become a standard in human forensics where sufficient nuclear DNA is available.

A number of tetranucleotide STRs and methods for STR-typing have been explored for application in human forensics. Commercial STR-typing kits are available that target different STR loci, including a common set of loci. The FBI Laboratory has established 13 nationally recognized core STR loci that are included in a national forensic DNA database known as the Combined DNA Index System (CODIS). The 13 CODIS core loci are CSF1PO, FGA, TH01, TPOX, VWA, D3S1358, D5S818, D7S820, D8S1179, D13S317, D16S539, D18S51, and D21S11. Sequence information for these loci are available from STRBase. The range of numbers of repeat units for reported alleles for these CODIS13 loci is 6-16, 15-51.2, 3-14, 6-13, 10-24, 9-20, 7-16, 6-15, 8-19, 5-15, 5-15, 7-27, and 24-38 respectively (Butler, J M, 2001 *Forensic DNA Typing* Academic Press). When profiles are available with allele information for all 13 of these core STR loci, the average probability of a random match is lower than one in a trillion among non-related individuals. STR-typing by DNA sequencing is less desirable as it presents time constraints and is labor intensive.

STR-typing using STR markers has become the human forensic "gold standard" as the combined information derived from the 13 distinct CODIS alleles provide enough information to uniquely identify an individual's DNA signature to a statistical significance of 1 in 10.sup.9. Standard or conventional STR-typing methods, which typically use amplification and electrophoretic size determination to resolve individual alleles, have certain limitations. At low STR copy number it is not uncommon to observe allele "drop out" in which a heterozygous individual is typed as a homozygote because one of the alleles is not detected. Additionally, in cases of highly degraded or low copy DNA samples, entire markers may drop out leaving only a few STRs from which to derive a DNA profile. In certain situations for example, such as mass disaster victim identification, a large number of samples with varying DNA quantity and quality can exist, many of which produce only partial STR profiles. While in some cases a partial profile can be used to include or exclude a potential suspect or identity, conventional STR typing methods sometimes do not provide sufficient resolution at the available loci in the case of a partial profile. Thus, there is a need within the forensics community to increase resolution of STR-typing methods, such that it is possible to derive additional information from degraded DNA samples which yield an incomplete set of STR markers, and from other samples where detection of the complete STR set is not possible.

Techniques would be beneficial that could resolve sequence polymorphisms in alleles and thus increase the observed allelic variation for several common STR loci, while maintaining the advantages of amplification-based techniques, such as rapidness and the ability to automate the procedure for high-throughput typing. Thus, there is a need for STR typing methods that provide a higher level of resolution compared with standard techniques. Moreover, there exists a need for the development of an automated platform capable of high-throughput sample processing to enable analysis of a large number of samples produced simultaneously or over a short period of time, as in the case of mass disaster or war.

Mass spectrometry provides detailed information about the molecules being analyzed, including high mass accuracy. It is also a process that can be easily automated. Electrospray ionization mass spectrometry (ESI-MS) provides a platform capable of automated sample processing, and can resolve sequence polymorphisms between STR alleles (Ecker et. al. (2006) *JALA*. 11:341-51).

Matrix-assisted laser desorption-ionization time-of-flight mass spectrometry (MALDI TOF MS) has been employed to analyze STR, SNP, and Y-chromosome markers. (Butler, J.; Becker, C. H. *Science and Technology Research Report to NIJ* 2001, *NCJ* 188292, October; Monforte, J. A.; Becker, C. H. *Nat Med* 1997, 3, 360-362; Taranenko, N. I.; Golovlev, V. V.; Allman, S. L.; Taranenko, N. V.; Chen, C. H.; Hong, J.; Chang, L. Y. *Rapid Commun Mass Spectrom* 1998, 12, 413-418; Butler, J. M.; Li, J.; Shaler, T. A.; Monforte, J. A.; Becker, C. H. *Int J Legal Med* 1999, 112, 45-49; Ross, P. L.; Belgrader, P. *Anal Chem* 1997, 69, 3966-3972). To obtain routinely the necessary mass accuracy and resolution using MALDI TOF MS, the amplicon size must be less than 100 bp, which often requires strategies such as enzymatic digestion and nested linear amplification. In the MALDI approach, PCR amplicons must be thoroughly desalted and co-crystallized with a suitable matrix prior to mass spectrometric analysis. The size reduction schemes and clean-up schemes employed for STR and SNP analyses in the cited reports resulted in the mass spectrometric analysis of only one strand of the PCR amplicon. By measuring the mass of only one strand of the amplicon, an unambiguous base composition may be difficult to determine and only the length of the allele may be obtained. Even with the size reduction schemes, mass measurement errors of 12 to 60 Daltons (Da) are observed for products in the size range 15000 to 25000 Da. This corresponds to mass measurement errors of the 800 to 2400 ppm. Because of poor mass accuracy and mass resolution typical of MALDI, multiplexing of STRs is difficult and not routine, although in one published report three STR loci were successfully multiplexed. The issue of allelic balance has not been addressed for MALDI-TOF-MS based assays.

U.S. Pat. Nos. 6,764,822 and 6,090,558 relate to methods for STR-typing using mass spectrometry (MS). Use of electrospray ionization (ESI)-MS to resolve STR alleles has been reported (Hannis and Muddiman, 2001, *Rapid Commun. Mass. Spectrom.* 15(5): 348-50; Hannis et. al, 2000, *Advances in Nucleic Acid and Protein Analysis, Manipulation and Sequencing*, 3926: 1017-2661). ESI-MS provides a platform capable of automated sample processing and analysis that can resolve sequence polymorphisms (Ecker et. al. (2006) *JALA*. 11:341-51).

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.*, 1996, 7, 1266-1269; Muddiman et al., *Anal. Chem.*, 1997, 69, 1543-1549; Wunschel et al., *Anal. Chem.*, 1998, 70, 1203-1207; Muddiman et al., *Rev. Anal. Chem.*, 1998, 17, 1-68). Electrospray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.* 1996, 10, 377-382).

There is an unmet need for methods and compositions for analysis of DNA forensic markers that approach the level of resolution sequencing affords, that is capable of scanning a substantial amount of the variation contained within an amplified fragment, yet that is also rapid, amenable to automation, and provides relevant information without the burden of extensive manual data interpretation. Preferably, such a method would not require a priori knowledge of the potentially informative sites within a sample to carry out an analysis. Preferably, such methods would be able to provide substantial resolving capability for forensic analyses in cases of degraded DNA or with relatively low amounts of DNA, for example, by allowing resolution of sequence polymorphisms that may allow discrimination of equal or same-length alleles based on small differences in sequence or base composition.

SUMMARY OF THE INVENTION

The methods compositions and kits provided herein are directed to forensic analysis and identity testing based on using mass spectrometry to "weigh" DNA forensic markers with enough accuracy to yield an unambiguous base composition (i.e. the number of A's, G's, C's and T's) which in turn can be used to derive a DNA profile for an individual. Importantly, these base composition profiles can be referenced to existing forensics databases derived from STR or other forensic marker profiles. The present disclosure provides methods, primer pair compositions and kits that are capable of resolving human forensic DNA samples using STR loci based upon length and sequence polymorphisms, as measured by base composition, in a high throughput manner.

The present invention is directed to methods of forensic analysis of DNA. In some embodiments the methods comprise identity testing. In some embodiments they comprise STR-typing. The methods provided herein can be distinguished from conventional amplification based STR-typing. For example, the methods provided herein provide the ability to assign allele designations for STR loci based upon size as determined by mass. In addition, the methods provided herein can further resolve apparently homozygous alleles by deriving information from the loci nucleotide sequence as measured by mass or base composition uncovering additional alleles within the loci.

In some embodiments the methods comprise: amplifying a nucleic acid from a sample with a oligonucleotide primer pair comprising a forward and a reverse primer, each between 13 and 40 nucleobases in length, wherein said forward primer and is designed to hybridize within a first conserved sequence region of said nucleic acid and said reverse primer is designed to hybridize within a second conserved sequence region of said nucleic acid, wherein said first and said second conserved sequence regions flank an intervening variable nucleic acid region comprising an STR locus, wherein said amplifying generates at least one amplification product that is between about 45 and about 200 nucleotides in length; determining the molecular mass of at least one strand of said at least one amplification product using mass spectrometry; and comparing said determined molecular mass to a molecular mass database comprising a plurality of molecular masses of a plurality of STR-identifying amplicons, each indexed to said oligonucleotide primer pair and to a reference allele that corresponds to said STR locus, wherein a match between said determined molecular mass and a molecular mass comprised in said molecular mass database identifies an STR allele in said sample.

In another embodiment, the methods further comprise: calculating the base composition of said at least one strand of said at least one amplification product using said determined molecular mass; and comparing said calculated base composition to a base composition database comprising a plurality of base compositions of STR-identifying amplicons, each indexed to said oligonucleotide primer pair and to a reference allele that corresponds to said STR locus, wherein a match between said calculated base composition and a base composition comprised in said base composition database identifies an STR allele in said sample.

In a preferred embodiment, the methods comprise: amplifying a nucleic acid from a sample with a oligonucleotide primer pair comprising a forward and a reverse primer, each between 13 and 40 nucleobases in length, wherein said forward primer and is designed to hybridize within a first conserved sequence region of said nucleic acid and said reverse primer is designed to hybridize within a second conserved sequence region of said nucleic acid, wherein said first and said second conserved sequence regions flank an intervening variable nucleic acid region comprising an STR locus, wherein said amplifying generates at least one amplification product that is between about 45 and about 200 nucleotides in length; determining the molecular mass of at least one strand of said at least one amplification product using mass spectrometry; calculating the base composition of said at least one strand of said at least one amplification product using said determined molecular mass; and comparing said calculated base composition to a base composition database comprising a plurality of base compositions of STR-identifying amplicons, each indexed to said oligonucleotide primer pair and to a reference allele that corresponds to said STR locus, wherein a match between said calculated base composition and a base composition comprised in said base composition database identifies an STR allele in said sample. In a preferred aspect, the nucleic acid comprises DNA and the determining of molecular mass and calculation of base composition and the comparing to the database are performed on both strands of the amplification product. The method also can optionally comprise an additional step of assigning an allele call, or number of repeats, for the STR locus being analyzed based upon the length of the STR-identifying amplicon as determined via mass spectrometry and/or base composition.

In another embodiment, if the previous steps do not yield a match with the STR-identifying base composition, the method may further comprise: calculating the base composition of said at least one amplification product using said determined molecular mass, wherein said calculated base composition identifies a previously unknown allele of said STR locus; and indexing said calculated base composition to said oligonucleotide primer pair, said previously unknown allele, said determined molecular mass and said sample in a database.

In one embodiment, the variable nucleic acid region varies in nucleic acid sequence. In one aspect, the variable nucleic acid region varies in nucleic acid sequence among two or more alleles of said STR locus that comprise the same number of repeat units. In another aspect, the variable nucleic acid region varies in nucleic acid sequence among two or more same-length alleles of said STR locus. In one aspect, the variation in nucleic acid sequence is not resolvable by conventional amplification-based STR-typing methods.

In another embodiment, the method comprises determining that the sample is heterozygous at said STR locus. In one aspect, the sample has been previously characterized as homozygous for said STR locus. In another aspect, the determined heterozygosity is not resolvable by conventional amplification-based STR-typing methods.

In another embodiment, the identified STR allele comprises at least one SNP. In one aspect, the STR locus is D5S818 and the SNP comprises a change from G to T or A to C, relative to a reference allele for said STR locus comprised in said database. In another aspect, The STR locus is D8S1179 and the SNP comprises a change from G to A or T to C relative to a reference allele for said STR locus comprised in said database. In another aspect, the STR locus is vWA and the SNP comprises a change from G to T, A to G, C to T, or A to C, relative to a reference allele for said STR locus comprised in said database. In another aspect, the STR locus is D13S317 and the SNP comprises a change from A to T relative to a reference allele for said STR locus comprised in said database. In another aspect, the STR locus is D7S820 and the SNP comprises a change from T to A relative to a reference allele for said STR locus comprised in said database. However, any SNP in any allele of any STR locus may be identified using the methods and primer pairs provided herein.

In one embodiment the method further comprises repeating said steps using at least one additional oligonucleotide primer pair, the forward and reverse primers of said at least one additional oligonucleotide primer pair being designed to hybridize to conserved regions that flank an STR locus selected from the group consisting of: VWA, TPOX, THO1, FGA, D21S11, D18S51, D16S539, D13S317, D8S1179, D7S820, D5S818, D3S, and CSF1PO. In one aspect, the repeating of said steps with said at least one additional oligonucleotide primer pair is carried out simultaneously to the performing of said steps with said first oligonucleotide primer pair. In one aspect, the repeating of said steps is carried out in a multiplex reaction.

In another embodiment, the method further comprises repeating said amplifying step with at least one additional oligonucleotide primer pair, wherein at least one of said at least one additional primer is designed to hybridize to conserved regions of the AMEL locus. In one aspect, the repeating of said amplifying step is carried out simultaneously to the performing of said amplifying step with said first oligonucleotide primer pair. In one aspect, the repeating of said amplifying step is carried out in a multiplex reaction.

In one embodiment, the mass spectrometry is electrospray mass spectrometry (ESI-MS). In another embodiment, the ESI-MS is selected from MS-TOF and FTCIR-MS.

Also provided herein are compounds, including the oligonucleotide primer pairs to be used in the methods provided herein. Also provided are amplification products (amplicons) and STR-typing or STR-identifying amplicons generated by the methods provided herein either empirically or in silico.

Also provided are kits that comprise said compounds, such as said oligonucleotide primer pairs.

In one embodiment, the oligonucleotide primer pair is between about 45 and about 200 nucleotides in length and comprises a forward and a reverse primer, each between 13 and 40 nucleobases in length, wherein said forward primer is designed to hybridize within a first conserved sequence region of a nucleic acid and said reverse primer is designed to hybridize within a second conserved sequence region of said nucleic acid, wherein said first and second conserved sequence regions flank an intervening variable nucleic acid region comprising an STR locus.

In one embodiment, the STR locus is selected from the group consisting of: VWA, TPOX, THO1, FGA, D21S11, D18S51, D16S539, D13S317, D8S1179, D7S820, D5S818, D3S, and CSF1PO. However, primers provided herein can be designed to hybridize to conserved regions adjacent to any STR locus. In an embodiment the primer pairs are purified primer pairs.

In one embodiment, the primer pair comprises at least 70%, at least 80%, at least 90%, at least 95% or at least 100% sequence identity with a oligonucleotide primer comprising the sequence of the pair of primers represented by SEQ ID NOs: 1:52, 2:53, 3:54, 4:55, 5:56, 5:57, 5:58, 5:59, 6:56, 6:57, 6:58, 6:59, 7:60, 8:61, 9:61, 8:62, 9:63, 9:64, 9:65, 9:66, 10:67, 11:68, 12:69, 13:70, 14:71, 15:72, 15:73, 16:72, 16:73, 17:74, 18:75, 19:76, 20:77, 21:78, 22:79, 23:80, 24:81, 25:82, 26:83, 27:84, 28:85, 29:86, 30:87, 31:88, 32:89, 32:90, 33:91, 34:90, 34:92, 35:93, 36:94, 37:95, 38:96, 39:97, 40:98, 41:99, 42:100, 42:101, 43:102, 44:103, 45:103, 46:104, 46:103, 47:104, 109:117, 110:118, 111:119, 112:120, 113:121, 114:122, 115:123, or 116:124.

In one embodiment, the STR locus is THO1. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 8:61, 9:61, 8:62, 9:63, 9:64, 9:65, 9:66, or 10:67. In one aspect, the oligonucleotide primer pair comprises at least 70%, at least 80%, at least 90%, at least 95% or at least 100% sequence identity with the oligonucleotide primer pair represented by SEQ ID NOs: 10:67. In one aspect, the oligonucleotide primer pair is the oligonucleotide primer pair represented by SEQ ID NOs: 10:67. In an embodiment the primer pairs targeting THO1 are purified primer pairs.

In another embodiment, the STR locus is TPOX. In one aspect, the oligonucleotide primer pair comprises at least 70%, at least 80%, at least 90%, at least 95% or at least 100% sequence identity with a oligonucleotide primer pair comprising the sequence of the pair of primers represented by SEQ ID NOs: 5:56, 5:57, 5:58, 5:59, 6:56, 6:57, 6:58, 6:59, or 7:60. In one aspect, the oligonucleotide primer pair comprises at least 70%, at least 80%, at least 90%, at least 95% or at least 100% sequence identity with the oligonucleotide primer pair represented by SEQ ID NOs: 7:60. In one aspect, the oligonucleotide primer pair is the oligonucleotide primer pair represented by SEQ ID NOs: 7:60. In an embodiment the primer pairs targeting TPOX are purified primer pairs.

In another embodiment, the STR locus is D8S1179. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 28:85, 29:86, 30:87, or 31:88. In one aspect, the oligonucleotide primer pair comprises at least 70%, at least 80%, at least 90%, at least 95% or at least 100% sequence identity with the oligonucleotide primer pair represented by SEQ ID NOs: 31:88. In another aspect, the oligonucleotide primer pair is the oligonucleotide primer pair represented by SEQ ID NOs: 31:88. In an embodiment the primer pairs targeting D8S1179 are purified primer pairs.

In another embodiment, the STR locus is D5S818. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 36:94, 37:95, 38:96, 39:97, and 40:98. In one aspect, the oligonucleotide primer pair comprises at least 70%, at least 80%, at least 90%, at least 95% or at least 100% sequence identity with the oligonucleotide primer pair represented by SEQ ID NOs: 40:98. In another aspect, the oligonucleotide primer pair is the oligonucleotide primer pair represented by SEQ ID NOs: 40:98. In an embodiment the primer pairs targeting D5S818 are purified primer pairs.

In another embodiment, the STR locus is CSF1PO. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 43:102, 44:103, 45:103, 46:104, 46:103, or 47:104. In one aspect, the oligonucleotide primer pair comprises at least 70%, at least 80%, at least 90%, at least 95% or at least 100% sequence identity with the oligonucleotide primer pair represented by SEQ ID NOs: 47:104. In another aspect, the oligonucleotide primer pair is the oligonucleotide primer pair represented by SEQ ID NOs: 47:104. In an embodiment the primer pairs targeting CSF1PO are purified primer pairs.

In another embodiment, the STR locus is D7S820. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 32:89, 32:90, 33:91, 34:90, 34:92, or 35:93. In one aspect, the oligonucleotide primer pair comprises at least 70%, at least 80%, at least 90%, at least 95% or at least 100% sequence identity with the oligonucleotide primer pair represented by SEQ ID NOs: 35:93. In another aspect, the oligonucleotide primer pair is the oligonucleotide primer pair represented by SEQ ID NOs: 35:93. In an embodiment the primer pairs targeting D7S820 are purified primer pairs.

In another embodiment, the STR locus is D13S317. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 22:79, 23:80, 24:81, 25:82, 26:83, or 27:84. In one aspect, the oligonucleotide primer pair comprises at least 70%, at least 80%, at least 90%, at least 95% or at least 100% sequence identity with the oligonucleotide primer pair represented by SEQ ID NOs: 27:84. In another aspect, the oligonucleotide primer pair is the oligonucleotide primer pair represented by SEQ ID NOs: 27:84. In an embodiment the primer pairs targeting D13S317 are purified primer pairs.

In another embodiment, the STR locus is D16S539. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 17:74, 18:75, 19:76, 20:77, or 21:78. In one aspect, the oligonucleotide primer pair comprises at least 70%, at least 80%, at least 90%, at least 95% or at least 100% sequence identity with the oligonucleotide primer pair represented by SEQ ID NOs: 21:78. In another aspect, the oligonucleotide primer pair is the oligonucleotide primer pair represented by SEQ ID NOs: 21:78. In an embodiment the primer pairs targeting D16S539 are purified primer pairs.

In another embodiment, the STR locus is vWA. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 1:52, 2:53, 3:54, or 4:55. In one aspect, the oligonucleotide primer pair comprises at least 70%, at least 80%, at least 90%, at least 95% or at least 100% sequence identity with the oligonucleotide primer pair represented by SEQ ID NOs: 4:55. In another aspect, the oligonucleotide primer pair is the oligonucleotide primer pair represented by SEQ ID NOs: 4:55. In an embodiment the primer pairs targeting vWA are purified primer pairs.

In one embodiment, the STR locus is FGA. In one aspect, the oligonucleotide primer pair comprises at least 70%, at least 80%, at least 90%, at least 95% or at least 100% sequence identity with an oligonucleotide primer pair comprising the sequence of the primer pair represented by SEQ ID NOs: 11:68, 111:119, 112:120, or 12:69. In an embodiment the primer pairs targeting FGA are purified primer pairs.

In another embodiment, the STR locus is D21S11. In one aspect, oligonucleotide primer pair comprises at least 70%, at least 80%, at least 90%, at least 95% or at least 100% sequence identity with an oligonucleotide primer pair comprising the sequence of the primer pair represented by SEQ ID NOs: 13:70, 109:117, 110:118, or 14:71. In an embodiment the primer pairs targeting D21S11 are purified primer pairs.

In another embodiment, the STR locus is D18S51. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 15:72, 15:73, 113:121, 114:122, 16:72, or 16:73. In an embodiment the primer pairs targeting D18S51 are purified primer pairs.

In another embodiment, the STR locus is D3S. In one aspect, the oligonucleotide primer pair comprises at least 70%, at least 80%, at least 90%, at least 95% or at least 100% sequence identity with an oligonucleotide primer pair comprising the sequence of the pair of primers represented by SEQ ID NOs: 41:99, 42:100, 115:123, 116:124, or 42:101. In an embodiment the primer pairs targeting D3S are purified primer pairs.

In some embodiments, the primers hybridize to conserved sequence regions within amelogenin (AMEL), which is used in sex-determination. In one aspect, each member of the primer pair has at least 70%, at least 80%, at least 90% or at least 100% sequence identity with the sequence of the corresponding member of a primer pair represented by any one or more of the following SEQ ID NOs: 48:105, 49:106, 50:107, and 51:108. In an embodiment the primer pairs targeting AMEL are purified primer pairs.

In one embodiment, the oligonucleotide primer pair comprises at least one modified nucleobase. In one aspect, the modified nucleobase is a mass-modified nucleobase. In one aspect, the mass modified nucleobase is 5-Iodo-C. In another aspect, the mass modified nucleobase comprises a molecular mass modifying tag. In one aspect, the modified nucleobase is a universal nucleobase. In one aspect, the universal nucleobase is inosine.

In another embodiment, at least one of said forward primer and said reverse primer comprises a non-templated T residue at its 5' end.

In another embodiment, at least one of said forward primer and said reverse primer comprises a G or a C residue at its 5' end.

In one embodiment the kit comprises an oligonucleotide primer pair provided herein and at least one additional primer pair, each of said at least one additional primer pair comprising a forward and a reverse primer designed to hybridize within conserved sequence regions of a nucleic acid that flank an intervening variable nucleic acid region of said nucleic acid comprising an STR locus selected comprising VWA, TPOX, THO1, FGA, D21S11, D18S51, D16S539, D13S317, D8S1179, D7S820, D5S818, D3S, or CSF1PO. In one aspect, the kit further comprises another additional oligonculeotide primer pair designed to hybridize within or to a sequence flanking an AMEL locus.

In one embodiment, the kit comprises a kit for forensic analysis comprising at least two oligonucleotide primer pairs, each designed to generate an amplification product that is between about 45 and about 200 nucleotides in length and comprising a forward and a reverse primer, wherein a first of said at least two oligonucleotide primer pairs comprises a first forward primer that is designed to hybridize within a first conserved sequence region of said nucleic acid and a first reverse primer that is designed to hybridize within a second conserved sequence region of said nucleic acid, wherein said first and second conserved sequence regions flank an intervening variable nucleic acid region comprising an STR locus, said STR being vWR, and wherein a second of said at least two oligonucleotide primer pairs is designed to hybridize within or to a sequence flanking an AMEL locus. In one aspect, the kit further comprises at least one additional primer pair designed to hybridize to conserved sequence regions flanking an STR locus selected from TPOX, TH01, D8S1179 and D5S818. In another aspect, the kit further comprises at least one additional primer pair designed to hybridize to conserved sequence regions flanking an STR locus selected from CSF1PO, D7S820, D13S317, and D16S539.

In an additional embodiment, the kits and methods described herein include or use all of the components to perform polymerase chain reaction (PCR). These components include, but are not limited to, deoxynucleotide triphosphates (dNTPs) for each nucleobase, a thermostable DNA polymerase and buffers useful in performing PCR. In an embodiment at least one dNTP is mass-modified. In an embodiment the mass-modified dNTP is a $^{13}C$-enriched dGTP.

BRIEF DESCRIPTION OF THE DRAWINGS

FIG. 6 is a summary of initial STR primer testing done on the Seracare blood sample N31773.

FIG. 8 is a summary of STR typing of the indicated AFDIL blood spot samples (sample number listed in the first column) using PCR amplification and ESI-MS using the methods provided herein. The numbers in each box refer to the allele call that was made for each allele in the particular sample for the particular STR locus. The number corresponds with standard nomenclature and indicates the number of repeat units in the allele. SNPs identified by the method are noted parenthetically with the base change. For example, a SNP that is a change of a T residue to an A residue is indicated as (T→A). Some samples, where only one number is listed carried two alleles of the same length.

FIG. 12 Shows results from alleles resolved using the AFDIL samples shown in FIG. 8 and the multiplex reaction mixes described in Table 7. Alleles and SNPs are indicated as in FIG. 8.

FIG. 13a shows results from multiplex reactions using the primer pairs listed in table 7 and methods provided herein to type 25 new AFDIL samples (indicated in the first column). Alleles and SNPs identified are indicated as in FIG. 8. All allele numbers (indicating number of repeat units) were consistent with typing results from conventional amplification based STR typing.

FIG. 13b shows results from multiplex reactions using the primer pairs listed in table 7 and methods provided herein to type 22 new FBI samples (indicated in the first column). Alleles and SNPs identified are indicated as in FIG. 8.

FIG. 13c is a table summarizing the results from FIGS. 13a and 13b.

FIG. 14 shows results of STR typing of NIST samples. Caucasian and African American samples are shown. Polymorphic alleles are indicated by coloring of cells as indicated in the bottom legend. The nature of each SNP is indicated by a letter designation next to the base allele call.

FIG. 15 shows results of STR typing of NIST samples. Hispanic samples are shown. Polymorphic alleles are indicated by coloring of cells as indicated in the bottom legend. The nature of each SNP is indicated by a letter designation next to the base allele call.

FIG. 18 illustrates the use of a mass tag to make an unambiguous SNP assignment in a PCR amplicon. The example above shows locus D8S1179, allele 14, amplified with Ibis primer pair 2818. A.) When amplified with natural dNTPs, a G→A and a T→C variant from allele 14 produce amplicons that are very close in mass (about 1 Da difference in each of the product strands). B.) Zoomed-in view of the forward strand masses for each of the three PCR products. There is an unambiguous detection of a SNP from the base allele 14 product, but only a 1 Da difference between masses for the forward strands of the G→A and T→C products, making the precise identity of the SNP potentially ambiguous between two possibilities. C.) When amplified with $^{13}$C-enriched dGTP in place of dGTP, a G→A and a T→C variant from allele 14 produce amplicons separated by nearly 11 Da, which allows unambiguous assignment of each SNP variant. D.) Zoomed-in view of the forward strand masses for each of the three PCR products amplified with $^{13}$C-enriched dGTP. There is an unambiguous detection of a SNP from the base allele 14 product, and an unambiguous assignment of the base switch involved in the SNP. The basic allele 14 product is separated from the G→A SNP by ~26 Da and from the T→C SNP by ~15 Da. The two SNP variants are separated by ~11 Da.

DESCRIPTION OF EMBODIMENTS

Figure 1A:
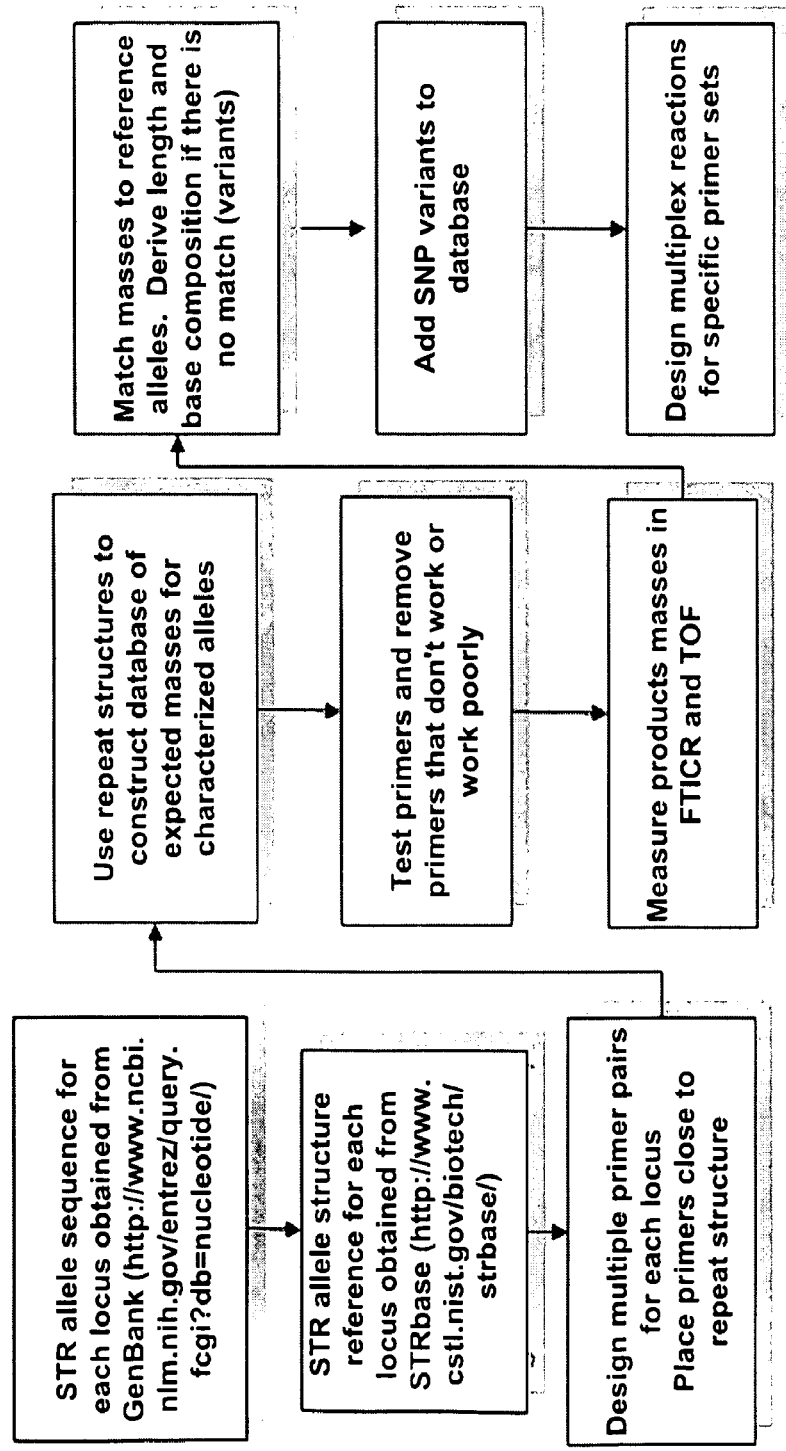
FIG. 1a is a flow chart illustrating an example of a primer selection and STR-typing method provided herein.

As used herein a "sample" refers to anything capable of being analyzed by the methods provided herein. In preferred embodiments, the sample comprises or is suspected one or more nucleic acids capable of analysis by the methods. Preferably, the samples comprise DNA. Samples can be forensic samples, which can include, for example, evidence from a crime scene, blood, blood stains, semen, semen stains, bone, teeth, hair saliva, urine, feces, fingernails, muscle tissue, cigarettes, stamps, envelopes, dandruff, fingerprints, and personal items. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid or DNA.

As used herein, "repeated DNA sequence," "tandem repeat locus," "tandem DNA repeat" and "satellite DNA" refer to repeated DNA sequences present in eukaryotic genomes. "VNTRs" (variable nucleotide tandem repeats) or "minisatellites" refer to medium sized repeat units that are about 10-100 linked nucleotides in length. "short tandem repeat," "STR", "simple sequence repeats" "SSR" and "microsatellite" refer to tandem DNA repeat regions having core units of between 2-6 nucleotides in length. STRs are characterized by the number of nucleotides in the core repeat unit. Dinucleotide, trinucleotide, and tetranucleotide STRs represent STRs with core repeat units of 2, 3, and 4 respectively.

"STR locus" also called "STR marker" refers to a particular place on a chromosome where the region of short tandem repeats are located. Particular sequence variations (number of repeat units and sequence polymorphisms) found at an STR locus are called "STR alleles." There are often several STR alleles for one STR locus within any given population. An individual can have more than one STR allele (one on each chromosome—maternal and paternal) for a given STR locus. Such an individual is said to be "heterozygous" at the particular STR locus. An individual with identical alleles on both chromosomes is said to be "homozygous." Individual variations of such locus are called alleles. For a particular STR locus, individuals in a population differ in the number of these core repeat units. Alleles at a particular STR locus can be said to be corresponding to that STR locus.

As used herein, "same-length STR alleles" or "same-length alleles" are used to refer to two or more alleles that share a common number of linked nucleotides or sequence length at the STR locus. Same-length alleles can differ in base composition or sequence. "Sequence length" refers to the number of linked nucleotides for a given nucleic acid, nucleic acid sequence or portion or region of such a sequence.

For certain STR loci, microvariant alleles have been identified that differ from common allele variants by one or more base pairs. These variations can be in the form of nucleotide insertion, deletion or nucleotide base changes. One such variation, "single nucleotide polymorphism" or "SNP" refers to a single nucleotide change compared with a reference sequence or common sequence. In some embodiments, the methods provided herein can discriminate alleles based on one or more SNPs, and can identify SNPs in STR loci.

A common nomenclature for STR loci and STR alleles developed by the International Society of Forensic Haemogenetics (ISFH) (Bar et al., *Int. Journal of Legal Medicine*, 1997, 107, 159-160). Alleles are named based on number of the core repeat unit. For example, an allele designated 12 for a particular STR locus would have 12 repeat units. Incomplete repeat units are designated with a decimal point following the whole number, for example, 12.2.

As used herein, "forensic DNA typing" refers to forensic methods for determining a genotype of any one or more loci of an individual, nucleic acid, sample, or evidence. "STR-typing" refers to forensic DNA typing or DNA typing using methods to determine genotype of one or more STR loci. STR-typing can be used for such purposes as forensics, identity testing, paternity testing, and other human identification means. Often, STR typing involves the amplification of multiple STR DNA loci that display a collection of alleles in the human population that differ in repeat number for each locus examined.

As used herein, "conventional STR-typing" or "standard STR-typing" refer to the most common available methods used for STR typing. Specifically, "conventional amplification-based STR typing" and "standard amplification-based STR typing" refer to the most common methods where STR loci are identified by amplification and resolved by assigning allele designations based on size or sequence length. Often, the products of such amplification reactions are analyzed by electrophoresis using fluorescent detection methods, and subsequent discrimination among different alleles based on amplification product length. The methods provided herein can be distinguished from conventional amplification based STR-typing. For example, the methods provided herein provide the ability to assign allele designations for STR loci based upon size as determined by mass. In addition, the methods provided herein can further resolve apparently homozygous alleles by deriving information from the loci nucleotide sequence as measured by mass or base composition uncovering additional alleles within the loci. "Allele call" in STR-typing refers to a genotype, STR-type or particular allele identified by a STR-typing method for an individual, nucleic acid or sample.

As used herein, "primers," "primer pairs" or "oligonucleotide primer pairs" are oligonucleotides that are designed to hybridize to conserved sequence regions within target nucleic acids, wherein the conserved sequence regions are conserved among two or more nucleic acids, alleles, or individuals. A primer pair is a pair of primers and thus comprises a forward and a reverse primer. In some embodiments, the conserved sequence regions (and thus the hybridized primers) flank an intervening variable nucleic acid region that varies among two or more alleles or individuals. Upon amplification, the primer pairs yield amplification products (also called amplicons) that comprise base composition variability between two or more individuals or nucleic acids. The variability of the base compositions allows for the identification of one or more individuals or a genotype of one or more individuals based on the amplicons and their base composition distinctions. In a preferred embodiment, primer pairs are designed to hybridize to regions that are directly adjacent to or nearly adjacent to the STR locus. It will be apparent, however, that some variations of the primers provided herein will serve to provide effective amplification of desired sequences. Such variations could include, for example, adding or deleting one or a few bases from the primer and/or shifting the position of the primer relative to the STR locus or variable region.

In some embodiments of the invention, the oligonucleotide primer pairs described herein can be purified. As used herein, "purified oligonucleotide primer pair," "purified primer pair," or "purified" means an oligonucleotide primer pair that is chemically-synthesized to have a specific sequence and a specific number of linked nucleosides. This term is meant to explicitly exclude nucleotides that are generated at random to yield a mixture of several compounds of the same length each with randomly generated sequence.

The primer pairs are designed to generate amplicons that are amenable to molecular mass analysis. Standard primer pair nomenclature is used herein, and includes naming of a reference sequence, hybridization coordinates, and other identifying information. For example, the forward primer for primer pair number 2823 is named VWA_M25858_1651_1681_F. The reference sequence for this primer (referred to in the name) is Gen Bank Accession Number: M25858. The number range "1651_1681" indicate that the primer hybridizes to these nucleotide coordinates within the reference sequence. The "F" denotes that this particular primer is the forward primer of the pair. The beginning of the primer name refers to the locus, gene, or other nucleic acid region or feature to which the primer is targeted, and thus hybridizes within. In the case of this forward primer of primer pair number 2823, the name indicates that the primer is targeted to VWA, a particular human STR. The primer pairs are selected and designed; however, to hybridize with two or more nucleic acids or nucleic acids from two or more individuals. So, the nomenclature used is merely to provide a reference sequence, and not to indicate that the primers hybridize with and generate an amplification product only from the reference sequence. Further, the sequences of the primer members of the primer pairs are not necessarily fully complementary to the conserved region of the reference sequence. Rather, the sequences are designed to be "best fit" amongst a plurality of nucleic acids at these conserved binding sequences. Therefore, the primer members of the primer pairs have substantial complementarity with the conserved regions of the nucleic acids, including the reference sequence nucleic acid.

As is used herein, the term "substantial complementarity" means that a primer member of a primer pair comprises between about 70%-100%, or between about 80-100%, or between about 90-100%, or between about 95-100%, or between about 99-100% complementarity with the conserved binding sequence of a nucleic acid from an individual. Similarly, the primer pairs provided herein may comprise between about 70%-100%, or between about 80-100%, or between about 90-100%, or between about 95-100% identity, or between about 99-100% sequence identity with the primer pairs disclosed in Table 5 These ranges of complementarity and identity are inclusive of all whole or partial numbers embraced within the recited range numbers. For example, and not limitation, 75.667%, 82%, 91.2435% and 97% complementarity or sequence identity are all numbers that fall within the above recited range of 70% to 100%, therefore forming a part of this description. In some embodiments, any oligonucleotide primer pair may have one or both primers with less then 70% sequence homology with a corresponding member of any of the primer pairs of Table 5 if the primer pair has the capability of producing an amplification product corresponding to the desired STR-identifying amplicon.

In some embodiments, the oligonucleotide primers are 13 to 40 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34, 35, 36, 37, 38, 39 or 40 nucleobases in length, or any range therewithin. The present invention contemplates using both longer and shorter primers. Furthermore, the primers may also be linked to one or more other desired moieties, including, but not limited to, affinity groups, ligands, regions of nucleic acid that are not complementary to the nucleic acid to be amplified, labels, etc. In other embodiments, any oligonucleotide primer pair may have one or both primers with a length greater than 40 nucleobases if the primer pair has the capability of producing an amplification product corresponding to the desired STR-identifying amplicon.

As used herein, the term "variable region" is used to describe a region that, in some embodiments, falls between the conserved regions to which primer pairs described herein hybridize. The primers described herein can be designed such that, when hybridized to the target, they flank variable regions. Variable regions possess distinct base compositions between two or more individuals or alleles, such that at least two alleles, nucleic acids from at least two individuals, or at least two nucleic acids can be resolved from one another by determining the base composition of the amplicon generated by the primers that flank such a variable region when bound, or in other words bind to sequence regions that flank the variable region. In one embodiment, the variable region comprises an STR locus. In one aspect, the variable region comprises a distinct base composition among two or more amplicons generated from two distinct alleles that comprise the same number of nucleotides, and are thus the same length. In one aspect, the base composition of the variable region differs only in sequence, and not in length among two or more alleles.

As used herein, the term "amplicon" and "amplification product" refer to a nucleic acid generated or capable of generation using the primer pairs and methods described herein. In particular, "STR-identifying amplicons," also called "STR-typing amplicons," "STR-typing amplification products," and "STR-identifying amplification products" are amplicons that can be used to determine the genotype (or identify the particular allele) for an individual nucleic acid at an STR locus. In some embodiments, the STR-typing amplicons are generated using in silico methods using electronic PCR and an electronic representation of primer pairs. The amplicons generated using in silico methods can be used to populate a database. The amplicon is preferably double stranded DNA; however, it can be RNA and/or DNA:RNA. The amplicon comprises the sequences of the conserved regions/primer pairs and the intervening variable region. As discussed herein, primer pairs are designed to generate amplicons from two or more alleles. The base composition of any given amplicon will include the primer pair, the complement of the primer pair, the conserved regions and the variable region from the nucleic acid that was amplified to generate the amplicon. One skilled in the art understands that the incorporation of the designed primer pair sequences into any amplicon will replace the native sequences at the primer binding site, and complement thereof. After amplification of the target region using the primers the resultant amplicons, including the primer sequences, generate the molecular mass data. Amplicons having any native sequences at the primer binding sites, or complement thereof, are undetectable because of their low abundance. Such is accounted for when identifying one or more nucleic acids from one or more alleles using any particular primer pair. The amplicon further comprises a length that is compatible with mass spectrometry analysis. STR-identifying amplicons (STR-typing amplicons) generate base composition signatures that are preferably unique to the identity of an STR allele.

Preferably, amplicons comprise from about 45 to about 200 consecutive nucleobases (i.e., from about 45 to about 200 linked nucleosides). One of ordinary skill in the art will appreciate that this range expressly embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nucleobases in length. One ordinarily skilled in the art will further appreciate that the above range is not an absolute limit to the length of an amplicon, but instead represents a preferred length range. Amplicons lengths falling outside of this range are also included herein so long as the amplicon is amenable to calculation of a base composition signature as herein described. As used herein, the term "about" means encompassing plus or minus 10%. For example, about 200 nucleotides refers to a range encompassing between 180 and 220 nucleotides.

As used herein, the term "molecular mass" refers to the mass of a compound as determined using mass spectrometry. Herein, the compound is preferably a nucleic acid, more preferably a double stranded nucleic acid, still more preferably a double stranded DNA nucleic acid and is most preferably an amplicon. When the nucleic acid is double stranded the molecular mass is determined for both strands. Here, the strands are separated either before introduction into the mass spectrometer, or the strands are separated by the mass spectrometer (for example, electro-spray ionization will separate the hybridized strands). The molecular mass of each strand is measured by the mass spectrometer.

As used herein, the term "base composition" refers to the number of each residue comprising an amplicon, without consideration for the linear arrangement of these residues in the strand(s) of the amplicon. The amplicon residues comprise, adenosine (A), guanosine (G), cytidine, (C), (deoxy) thymidine (T), uracil (U), inosine (I), nitroindoles such as 5-nitroindole or 3-nitropyrrole, dP or dK (Hill et al.), an acyclic nucleoside analog containing 5-nitroindazole (Van Aerschot et al., Nucleosides and Nucleotides, 1995, 14, 1053-1056), the purine analog 1-(2-deoxy-.beta.-D-ribofuranosyl)-imidazole-4-carboxamide, 2,6-diaminopurine, 5-propynyluracil, 5-propynylcytosine, phenoxazines, including G-clamp, 5-propynyl deoxy-cytidine, deoxy-thymidine nucleotides, 5-propynylcytidine, 5-propynyluridine and mass tag modified versions thereof, including 7-deaza-2'-deoxyadenosine-5'-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $15.^N$ or $13.^C$ or both $15.^N$ and $13.^C$. Preferably, the non-natural nucleosides used herein include 5-propynyluracil, 5-propynylcytosine and inosine. Herein the base composition for an unmodified DNA amplicon is notated as $A_w G_x C_y T_z$, wherein w, x, y and z are each independently a whole number representing the number of said nucleoside residues in an amplicon. Base compositions for amplicons comprising modified nucleosides are similarly notated to indicate the number of said natural and modified nucleosides in an amplicon. Base compositions are calculated from a molecular mass measurement of an amplicon, as described below. The calculated base composition for any given amplicon is then compared to a database of base compositions. In one embodiment, the database comprises base compositions of STR-typing amplicons. A match between the calculated base composition and a single database entry reveals the identity of the target nucleic acid or a genotype of an individual.

As is used herein, the term "base composition signature" refers to the base composition generated by any one particular amplicon.

As used herein, the term "database" is used to refer to a collection of base composition or molecular mass data. The base composition and/or molecular mass data in the database is indexed to specific individuals (subjects), alleles, or reference alleles and also to specific STR-identifying amplicons and primer pairs. In one embodiment, the data are indexed to particular STR loci. As used herein, a "reference allele" is an allele comprised in a database that has been previously determined to have a certain base composition, length, molecular mass, size and/or genotype. The reference allele may be indexed to primer pairs and amplicons provided herein. The base composition data reported in the database comprises the number of each nucleoside in an amplicon that would be generated for each allele or individual using each primer. The database can be populated by empirical data. In this aspect of populating the database, a nucleic acid with a particular allele or from a particular individual is selected and a primer pair is used to generate an amplicon. The amplicon's molecular mass is determined using a mass spectrometer and the base composition calculated therefrom. An entry in the database is made to associate the base composition with the allele or individual and the primer pair used. The database may also be populated using other databases comprising allele or individual nucleic acid information. For example, using the GenBank database it is possible to perform electronic PCR using an electronic representation of a primer pair. Databases can be populated from other databases, such as FBI databases. This in silico method will provide the base composition for any or all selected allele(s) and/or individuals stored in the database. The information is then used to populate the base composition database as described above. A base composition database can be in silico, a written table, a reference book, a spreadsheet or any form generally amenable to databases. Preferably, it is in silico.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

As used herein, a "wobble base" is a variation in a codon found at the third nucleotide position of a DNA triplet. Variations in conserved regions of sequence are often found at the third nucleotide position due to redundancy in the amino acid code.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. In context of the present invention, sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers of the present invention, sequence identity is properly determined when the alignment is designated as Plus/Plus. Sequence identity may also encompass alternate or "modified" nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "triangulation identification" means the employment of more than one primer pair, two or more primer pairs, three or more primer pairs, or a plurality of primer pairs to generate amplicons necessary for the identification or typing of a nucleic acid or individual. The more than one primer pair can be used in individual wells or in a multiplex PCR assay. In a "multiplex" assay, the methods provided herein are performed with two or more primer pairs simultaneously. Alternatively, PCR reaction may be carried out in single wells comprising a different primer pair in each well. Following amplification the amplicons are pooled into a single well or container which is then subjected to molecular mass analysis. The combination of pooled amplicons can be chosen such that the expected ranges of molecular masses of individual amplicons are not overlapping and thus will not complicate identification of signals. Triangulation works as a process of elimination, wherein a first primer pair identifies that an unknown allele may be one of a group of alleles. Subsequent primer pairs are used in triangulation identification to further refine the identity of the allele amongst the subset of possibilities generated with the earlier primer pair. Triangulation identification is complete when the identity of the allele is determined. The triangulation identification process is also used to reduce false negative and false positive signals. Alternatively, if more than one primer pair are used in a multiplex assay, the combination of amplicons are generated simultaneously and can be analyzed simultaneously, comparing the multiple resultant molecular masses or base compositions to multiple amplicons in a database that are indexed to the different primer pairs used in the multiplex assay.

Provided herein are methods and compositions directed to unbiased forensic analysis and identity testing including STR typing of samples comprising nucleic acids using amplicons and ESI-MS to determine mass and base composition. The methods herein provide substantial accuracy to yield an unambiguous base composition (i.e. the number of A's, G's, C's and T's) which in turn can be used to derive a DNA profile for an individual. Importantly, these base composition profiles can be referenced to existing forensics databases derived from STR or other forensic marker profiles and/or can be added to such databases. Because the methods use molecular mass and base compositions to derive specific alleles, the methods and compositions provided herein are capable of detecting SNPs within STR regions that go undetected by conventional electrophoretic STR-typing analyses. For example, all "allele type 13" for the D5S818 marker are not equivalent; some contain a G to T (G→T) SNP, which distinguish them from individuals containing the "normal" allele type 13. Similarly, individuals which are typed as homozygous for this allele may in fact be heterozygotes containing alleles 13 and 13.sub.G/T_SNP. These types of change would not be detected by standard STR-typing methods and kits that use electrophoretic size discrimination to resolve STR alleles.

In a preferred embodiment, the amplicons are STR-identifying amplicons or STR-identifying amplification products. In this embodiment, primers are selected to hybridize to conserved sequence regions of nucleic acids, which flank a variable nucleic acid sequence region, derived from the samples to yield an STR-typing amplicon that can be amplified and is amenable to molecular mass determination. A base composition is calculated from the molecular mass, which indicates the number of each nucleotide in the amplicon. The molecular mass or corresponding base composition or base composition signature of the amplicon is then compared to a database comprising molecular masses or base composition signatures that are indexed to alleles and/or individuals and the primer pair that was used to generate the amplicon. A match of the determined molecular mass or calculated base composition to a molecular mass or base composition in the database associates the nucleic acid from the sample with an allele or individual indexed in the database. In some cases, the nucleic acid from the sample or a particular allele associates with more than one individual or identity. In these cases, one or more additional primer pairs are used either subsequently or simultaneously to generate one or more additional amplicons. The mass and base composition of the one or more additional amplicons are determined/calculated and the methods provided herein are used to compare the results to a database and further characterize and preferably identity the sample. This type of analysis can be carried out as described herein using triangulation, or using multiplex assays. The present method provides rapid throughput analysis and does not require nucleic acid sequencing for identification of nucleic acids from samples.

In one embodiment, the method is carried out with two or more primer pairs in a multiplex reaction. In one aspect, when the method is carried out in a multiplex reaction, it may be advantageous to use PCR reagents with high magnesium, for example, 3 mM magnesium chloride. As is known in the art, such reagents favor adenylation of amplification products. In one embodiment, it is advantageous to minimize split-peak results that can occur when there is adenylation of only a fraction of the amplification products in the sample, for example, generation of a fraction of the amplification products with a slightly different length than other products. Thus, in a preferred aspect, it is desired to promote full or about full adenylation. In one aspect, the primer pairs are configured so as to promote full adenylation such that one or both of the forward and reverse primer comprises a C or a G nucleobase at the 5' end. Temperatures in the cycle reaction may also be adjusted to promote full adenylation while retaining efficacy, for example, by using an annealing temperature of about 61 degrees C.

In some embodiments, amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplicon include, but are not limited to, cleavage with restriction enzymes or cleavage primers, for example. Thus, in some embodiments, amplicons are larger than 200 nucleobases and are amenable to molecular mass determination following restriction digestion. Methods of using restriction enzymes and cleavage primers are well known to those with ordinary skill in the art.

In some embodiments, amplicons are obtained using the polymerase chain reaction (PCR) which is a routine method to those with ordinary skill in the molecular biology arts. In some embodiments, the PCR is accomplished by using the polymerase chain reaction and a polymerase chain reaction is catalyzed by a polymerase enzyme whose function is modified relative to a native polymerase. In some embodiments the modified polymerase enzyme is exo(-) Pfu polymerase which catalyzes the addition of nucleotide residues to staggered restriction digest products to convert the staggered digest products to blunt-ended digest products. Other amplification methods may be used such as ligase chain reaction (LCR), low-stringency single primer PCR, and multiple strand displacement amplification (SDA). These methods are also known to those with ordinary skill. (Michael, S F., Biotechniques (1994), 16:411-412 and Dean et al., Proc. Natl. Acad. Sci. U.S.A. (2002), 99, 5261-5266).

Mass spectrometry (MS)-based detection of PCR products provides a means for determination of BCS which has several advantages. MS is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons. Intact molecular ions can be generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751. The accurate measurement of molecular mass for large DNAs is limited by the adduction of cations from the PCR reaction to each strand, resolution of the isotopic peaks from natural abundance $^{13}$C and $^{15}$N isotopes, and assignment of the charge state for any ion. The cations are removed by in-line dialysis using a flow-through chip that brings the solution containing the PCR products into contact with a solution containing ammonium acetate in the presence of an electric field gradient orthogonal to the flow. The latter two problems are addressed by operating with a resolving power of >100,000 and by incorporating isotopically depleted nucleotide triphosphates into the DNA. The resolving power of the instrument is also a consideration. At a resolving power of 10,000, the modeled signal from the $[M-14H+]^{14-}$charge state of an 84 mer PCR product is poorly characterized and assignment of the charge state or exact mass is impossible. At a resolving power of 33,000, the peaks from the individual isotopic components are visible. At a resolving power of 100,000, the isotopic peaks are resolved to the baseline and assignment of the charge state for the ion is straightforward. The [$^{13}$C, $^{15}$N]-depleted triphosphates are obtained, for example, by growing microorganisms on depleted media and harvesting the nucleotides (Batey et al., *Nucl. Acids Res.,* 1992, 20, 4515-4523).

While mass measurements of intact nucleic acid regions are believed to be adequate, tandem mass spectrometry (MS$^n$) techniques may provide more definitive information pertaining to molecular identity or sequence. Tandem MS involves the coupled use of two or more stages of mass analysis where both the separation and detection steps are based on mass spectrometry. The first stage is used to select an ion or component of a sample from which further structural information is to be obtained. The selected ion is then fragmented using, e.g., blackbody irradiation, infrared multiphoton dissociation, or collisional activation. For example, ions generated by electrospray ionization (ESI) can be fragmented using IR multiphoton dissociation. This activation leads to dissociation of glycosidic bonds and the phosphate backbone, producing two series of fragment ions, called the w-series (having an intact 3' terminus and a 5' phosphate following internal cleavage) and the a-Base series (having an intact 5' terminus and a 3' furan).

The second stage of mass analysis is then used to detect and measure the mass of these resulting fragments of product ions. Such ion selection followed by fragmentation routines can be performed multiple times so as to essentially completely dissect the molecular sequence of a sample.

If there are two or more targets of similar molecular mass, or if a single amplification reaction results in a product which has the same mass as two or more reference standards, they can be distinguished by using mass-modifying "tags." Such an oligonucleotide is said to be mass-modified. In this embodiment, a nucleotide analog or "tag" is incorporated during amplification (e.g., a 5-(trifluoromethyl) deoxythymidine triphosphate) which has a different molecular weight than the unmodified base so as to improve distinction of masses. Such tags are described in, for example, WO 97/33000, which is incorporated herein by reference in its entirety. This further limits the number of possible base compositions consistent with any mass. For example, 5-(trifluoromethyl)deoxythymidine triphosphate can be used in place of dTTP in a separate nucleic acid amplification reaction. Measurement of the mass shift between a conventional amplification product and the tagged product is used to quantitate the number of thymidine nucleotides in each of the single strands. Because the strands are complementary, the number of adenosine nucleotides in each strand is also determined.

In contrast the mass tag approach, in a preferred embodiment mass-modified dNTPs are employed to further limit the number of base pair combinations and also to resolve SNPs that are not resolvable when using unmodified dNTPs. An example of how $^{13}$C-enriched dGTP is used in the methods of the instant patent application see FIG. 18.

In another amplification reaction, the number of G and C residues in each strand is determined using, for example, the cytidine analog 5-methylcytosine (5-meC) or 5-prolynylcytosine. propyne C. The combination of the A/T reaction and G/C reaction, followed by molecular weight determination, provides a unique base composition. This method is summarized in Table 1.

TABLE 1

| Mass tag | Double strand sequence | Single strand Sequence | Total mass this strand | Base info this strand | Base info other strand | Total base comp. Top strand | Total base comp. Bottom strand |
|---|---|---|---|---|---|---|---|
| T*.mass (T*-T) = x | T*ACGT*ACGT* AT*GCAT*GCA | T*ACGT*ACGT* | 3x | 3T | 3A | 3T 2A 2C 2G | 3A 2T 2G 2C |
| | | AT*GCAT*GCA | 2x | 2T | 2A | | |

TABLE 1-continued

| Mass tag | Double strand sequence | Single strand Sequence | Total mass this strand | Base info this strand | Base info other strand | Total base comp. Top strand | Total base comp. Bottom strand |
|---|---|---|---|---|---|---|---|
| C*.mass (C*-C) = y | TAC*GTAC*GT ATGC*ATGC*A | TAC*GTAC*GT | 2x | 2C | 2G | | |
| | | ATGC*ATGC*A | 2x | 2C | 2G | | |

In the example shown in Table 1, the mass tag phosphorothioate A (A*) was used to distinguish a *Bacillus anthracis* cluster. The *B. anthracis* ($A_{14}G_9C_{14}T_9$) had an average MW of 14072.26, and the *B. anthracis* ($A_1A*_{13}G_9C_{14}T_9$) had an average molecular weight of 14281.11 and the phosphorothioate A had an average molecular weight of +16.06 as determined by ESI-TOF MS.

In another example, assume the measured molecular masses of each strand are 30,000.115 Da and 31,000.115 Da respectively, and the measured number of dT and dA residues are (30,28) and (28,30). If the molecular mass is accurate to 100 ppm, there are 7 possible combinations of dG+dC possible for each strand. However, if the measured molecular mass is accurate to 10 ppm, there are only 2 combinations of dG+dC, and at 1 ppm accuracy there is only one possible base composition for each strand.

Signals from the mass spectrometer may be input to a maximum-likelihood detection and classification algorithm such as is widely used in radar signal processing. Processing may end with a Bayesian classifier using log likelihood ratios developed from the observed signals and average background levels. Background signal strengths are estimated and used along with the matched filters to form signatures which are then subtracted. the maximum likelihood process is applied to this "cleaned up" data in a similar manner employing matched filters and a running-sum estimate of the noise-covariance for the cleaned up data.

In some embodiments, the DNA analyzed is human DNA obtained from forensic samples, for example, human saliva, hair, blood, or nail.

Embodiments provided herein comprise primer pairs which are designed to bind to highly conserved sequence regions of DNA. In some embodiments, the conserved sequence regions flank an intervening variable region such as the variable sections found within regions STRs and yield amplification products which ideally provide enough variability to provide a forensic conclusion, and which are amenable to molecular mass analysis. By the term "highly conserved," it is meant that the sequence regions exhibit from about 80 to 100%, or from about 90 to 100%, or from about 95 to 100% identity, or from about 80 to 99%, or from about 90 to 99%, or from about 95 to 99% identity. The molecular mass of a given amplification product provides a means of drawing a forensic conclusion due to the variability of the variable region. Thus, design of primers involves selection of a variable section with optimal variability in the DNA of different individuals.

In some embodiments, each member of the pair has at least 70%, at least 80%, at least 90%, at least 95%, or at least 99% sequence identity with the sequence of the corresponding member of a primer pair represented by any one or more of the following SEQ ID NOs: 1:52, 2:53, 3:54, 4:55, 5:56, 5:57, 5:58, 5:59, 6:56, 6:57, 6:58, 6:59, 7:60, 8:61, 9:61, 8:62, 9:63, 9:64, 9:65, 9:66, 10:67, 11:68, 12:69, 13:70, 14:71, 15:72, 15:73, 16:72, 16:73, 17:74, 18:75, 19:76, 20:77, 21:78, 22:79, 23:80, 24:81, 25:82, 26:83, 27:84, 28:85, 29:86, 30:87, 31:88, 32:89, 32:90, 33:91, 34:90, 34:92, 35:93, 36:94, 37:95, 38:96, 39:97, 40:98, 41:99, 42:100, 42:101, 43:102, 44:103, 45:103, 46:104, 46:103, 47:104, 48:105, 49:106, 50:107, 109:117, 110:118, 111:119, 112:120, 113:121, 114:122, 115:123, 116:124, and 51:108.

In some embodiments, the conserved sequence region of DNA to which the primer pairs hybridize flank STR loci. Preferably, the STR loci are core CODIS loci.

In one embodiment, the STR locus comprises vWA. In one aspect each member of the primer pair has at least 70%, at least 80%, at least 90%, at least 95% or at least 100% sequence identity with the sequence of the corresponding member of a primer pair represented by any one or more of the following SEQ ID NOs: 1:52, 2:53, 3:54, and 4:55.

In another embodiment, the STR locus is TPOX. In one aspect, each member of the primer pair has at least 70%, at least 80%, at least 90%, at least 95% or at least 100% sequence identity with the sequence of the corresponding member of a primer pair represented by any one or more of the following SEQ ID NOs: 5:56, 5:57, 5:58, 5:59, 6:56, 6:57, 6:58, 6:59, and 7:60.

In another embodiment, the STR locus is THO1. In one aspect, each member of the primer pair has at least 70%, at least 80%, at least 90%, at least 95% or at least 100% sequence identity with the sequence of the corresponding member of a primer pair represented by any one or more of the following SEQ ID NOs: 8:61, 9:61, 8:62, 9:63, 9:64, 9:65, 9:66, and 10:67.

In another embodiment, the STR locus is FGA. In one aspect, each member of the primer pair has at least 70%, at least 80%, at least 90%, at least 95% or at least 100% sequence identity with the sequence of the corresponding member of a primer pair represented by any one or more of the following SEQ ID NOs: 11:68, 111:119, 112:120, and 12:69.

In another embodiment, the STR locus is D21S11. In one aspect, each member of the primer pair has at least 70%, at least 80%, at least 90%, at least 95% or at least 100% sequence identity with the sequence of the corresponding member of a primer pair represented by any one or more of the following SEQ ID NOs: 13:70, 109:117, 110:118, and 14:71.

In another embodiment, the STR locus is D18S51. In one aspect, each member of the primer pair has at least 70%, at least 80%, at least 90%, at least 95% or at least 100% sequence identity with the sequence of the corresponding member of a primer pair represented by any one or more of the following SEQ ID NOs: 15:72, 15:73, 16:72, 113:121, 114:122, and 16:73.

In another embodiment, the STR locus is D16S539. In one aspect, each member of the primer pair has at least 70%, at least 80%, at least 90%, at least 95% or at least 100% sequence identity with the sequence of the corresponding member of a primer pair represented by any one or more of the following SEQ ID NOs: 17:74, 18:75, 19:76, 20:77, and 21:78.

In another embodiment, the STR locus is D13S317. In one aspect, each member of the primer pair has at least 70%, at least 80%, at least 90%, at least 95% or at least 100% sequence identity with the sequence of the corresponding member of a primer pair represented by any one or more of the following SEQ ID NOs: 22:79, 23:80, 24:81, 25:82, 26:83, and 27:84.

In another embodiment, the STR locus is D8S1179. In one aspect, each member of the primer pair has at least 70%, at least 80%, at least 90%, at least 95% or at least 100% sequence identity with the sequence of the corresponding member of a primer pair represented by any one or more of the following SEQ ID NOs: 28:85, 29:86, 30:87, and 31:88.

In another embodiment, the STR locus is D7S820. In one aspect, each member of the primer pair has at least 70%, at least 80%, at least 90%, at least 95% or at least 100% sequence identity with the sequence of the corresponding member of a primer pair represented by any one or more of the following SEQ ID NOs: 32:89, 32:90, 33:91, 34:90, 34:92, and 35:93.

In another embodiment, the STR locus is D5S818. In one aspect, each member of the primer pair has at least 70%, at least 80%, at least 90%, at least 95% or at least 100% sequence identity with the sequence of the corresponding member of a primer pair represented by any one or more of the following SEQ ID NOs: 36:94, 37:95, 38:96, 39:97, and 40:98.

In another embodiment, the STR locus is D3 S. In one aspect, each member of the primer pair has at least 70%, at least 80%, at least 90%, at least 95% or at least 100% sequence identity with the sequence of the corresponding member of a primer pair represented by any one or more of the following SEQ ID NOs: 41:99, 42:100, 115:123, 116:124, and 42:101.

In another embodiment, the STR locus is CSF1PO. In one aspect, each member of the primer pair has at least 70%, at least 80%, at least 90%, at least 95% or at least 100% sequence identity with the sequence of the corresponding member of a primer pair represented by any one or more of the following SEQ ID NOs: 43:102, 44:103, 45:103, 46:104, 46:103, 47:104.

In some embodiments, the primers hybridize to conserved sequence regions within amelogenin (AMEL), which is used in sex-determination. In one aspect, each member of the primer pair has at least 70%, at least 80%, at least 90%, at least 95% or at least 100% sequence identity with the sequence of the corresponding member of a primer pair represented by any one or more of the following SEQ ID NOs: 48:105, 49:106, 50:107, and 51:108.

In one embodiment the methods are performed using a plurality of primer pairs. In one embodiment, the primer pairs comprise a primer pair that is designed to hybridize to conserved regions within AMEL and another primer pair designed to hybridize to conserved regions flanking the vWA STR locus. In one aspect, the plurality of primer pairs further comprises four additional primer pairs. In one aspect, the four additional primer pairs are designed to hybridize within conserved sequence regions flanking the TPOX, TH01, D8S1179 and D5S818 STR loci respectively. In another aspect, the four additional primer pairs are designed to hybridize within conserved sequence regions flanking the CSF1PO, D7S820, D13S317, and D16S539 STR loci respectively.

In a still further embodiment, the primer pairs are combined and used in a multiplex reaction. One aspect of this multiplex embodiment is configured to analyze 10 loci in two six-plex reactions. Another aspect of this multiplex embodiment is configured to analyze 14 loci in five tri-plex reactions plus three single-plex reactions. A preferred embodiment of this aspect is configured with primer pairs targeting D3S1358, vWA and D13S317 in one tri-plex reaction; primers targeting D16S539, CSF1PO and THO1 in a second tri-plex reaction; primers targeting TPOX, AMEL and D8S1179 in a third tri-plex reaction; primer pairs targeting AMEL, D7S820 and D5S818 in a fourth tri-plex reaction; primer pairs targeting D16S536, vWA and D5S818 in a fifth tri-plex reaction; a primer pair targeting D21S11 in a first single-plex reaction; a primer pair targeting FGA in a second single-plex reaction; and D18S51 in a third single-plex reaction.

In one embodiment, the plurality of primer pairs comprises the primer pairs represented by: SEQ ID NOs 4:55 and 51:108. In one aspect the primer pairs further comprise four additional primer pairs. In one aspect, the four additional primer pairs comprise the primer pairs represented by SEQ ID NOs: 7:60, 10:67, 31:88, and 40:98. In another aspect, the four additional primer pairs comprise the primer pairs represented by SEQ ID NOs: 47:104, 35:93, 27:84, and 21:78.

Ideally, primer hybridization sites are highly conserved in order to facilitate the hybridization of the primer. In cases where primer hybridization is less efficient due to lower levels of conservation of sequence, the primers provided herein can be chemically modified to improve the efficiency of hybridization. For example, because any variation (due to codon wobble in the $3^{rd}$ position) in these conserved regions among species is likely to occur in the third position of a DNA triplet, oligonucleotide primers can be designed such that the nucleotide corresponding to this position is a base which can bind to more than one nucleotide, referred to herein as a "universal base." For example, under this "wobble" pairing, inosine (I) binds to U, C or A; guanine (G) binds to U or C, and uridine (U) binds to U or C. Other examples of universal bases include nitroindoles such as 5-nitroindole or 3-nitropyrrole (Loakes et al., *Nucleosides and Nucleotides,* 1995, 14, 1001-1003), the degenerate nucleotides dP or dK ((Hill et al.), an acyclic nucleoside analog containing 5-nitroindazole (Van Aerschot et al., *Nucleosides and Nucleotides,* 1995, 14, 1053-1056) or the purine analog 1-(2-deoxy-beta-D-ribofuranosyl)-imidazole-4-carboxamide (Sala et al., *Nucl. Acids Res.,* 1996, 24, 3302-3306).

In another embodiment, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, propyne T (5-propynyluridine) which binds to adenine and propyne C (5-propynylcytidine) and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are claimed in U.S. Ser. No. 10/294,203 which is also commonly owned and incorporated herein by reference in entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007, 992 and 6,028,183, each of which is incorporated herein by reference in its entirety. Thus, In other embodiments, the primer pair has at least one modified nucleobase such as 5-propynylcytidine or 5-propynyluridine.

Also provided herein are isolated DNA amplicons which are produced by the process of amplification of a sample of DNA with any of the above-mentioned primers.

While the methods compounds and compositions provided herein have been described with specificity in accordance with certain of its embodiments, the following examples serve only to illustrate the invention and are not intended to limit the same. The examples provided are only examples, and one skilled in the art will understand that other techniques can be used by those skilled in the art and such different techniques will not depart from the spirit of the invention (T. Maniatis et al., in Molecular Cloning. A. Laboratory Manual. CSH Lab. N.Y. (2001).

EXAMPLES

Example 1

Nucleic Acid Isolation and Amplification

General Genomic DNA Sample Prep Protocol:

Raw samples were filtered using Supor-200 0.2 membrane syringe filters (VWR International). Samples were transferred to 1.5 ml eppendorf tubes pre-filled with 0.45 g of 0.7 mm Zirconia beads followed by the addition of 350 µl of ATL buffer (Qiagen, Valencia, Calif.). The samples were subjected to bead beating for 10 minutes at a frequency of 19 l/s in a Retsch Vibration Mill (Retsch). After centrifugation, samples were transferred to an S-block plate (Qiagen, Valencia, Calif.) and DNA isolation was completed with a BioRobot 8000 nucleic acid isolation robot (Qiagen, Valencia, Calif.).

Isolation of Blood DNA—

Blood DNA was isolated using an MDx Biorobot according to according to the manufacturer's recommended procedure (Isolation of blood DNA on Qiagen QIAamp® DNA Blood BioRobot® MDx Kit, Qiagen, Valencia, Calif.). In some cases, DNA from blood punches were processed with a Qiagen QIAmp DNA mini kit using the manufacturer's suggested protocol for dried blood spots.

Isolation of Buccal Swab DNA—

Since the manufacturer does not support a full robotic swab protocol, the blood DNA isolation protocol was employed after each swab was first suspended in 400 ml PBS+400 ml Qiagen AL buffer+20 µl Qiagen Protease solution in 14 ml round-bottom falcon tubes, which were then loaded into the tube holders on the MDx robot.

Isolation of DNA from Nails and Hairs—

The following procedure employs a Qiagen DNeasy® tissue kit and represents a modification of the manufacturer's suggested procedure: hairs or nails were cut into small segments with sterile scissors or razorblades and placed in a centrifuge tube to which was added 1 ml of sonication wash buffer (10 mM TRIS-Cl, pH 8.0+10 mM EDTA+0.5% Tween-20. The solution was sonicated for 20 minutes to dislodge debris and then washed 2× with 1 ml ultrapure double deionized water before addition of 100 µl of Buffer X1 (10 mM TRIS-Cl, ph 8.0+10 mM EDTA+100 mM NaCl+40 mM DTT+2% SDS+250 :g/ml Qiagen proteinase K). The sample was then incubated at 55° C. for 1-2 hours, after which 200 µl of Qiagen AL buffer and 210 µl isopropanol were added and the solution was mixed by vortexing. The sample was then added to a Qiagen DNeasy mini spin column placed in a 2 ml collection tube and centrifuged for 1 min at 6000 g (8000 rpm). Collection tube and flow-through were discarded. The spin column was transferred to a new collection tube and 500 µl of buffer AW2 was added before centrifuging for 3 min. at 20,000 g (14,000 rpm) to dry the membrane. For elution, 50-100 µl of buffer AE was pipetted directly onto the DNeasy membrane and eluted by centrifugation (6000 g-8000 rpm) after incubation at room temperature for 1 min.

Amplification by PCR—

An exemplary PCR procedure for amplification of DNA is the following: A 50 µl total volume reaction mixture contained 1× GenAmp® PCR buffer II (Applied Biosystems)–10 mM TRIS-Cl, pH 8.3 and 50 mM KCl, 1.5 mM $MgCl_2$, 400 mM betaine, 200 µM of each dNTP (Stratagene 200415), 250 nM of each primer, and 2.5-5 units of Pfu exo(-) polymerase Gold (Stratagene 600163) and at least 50 pg of template DNA. All PCR solution mixing was performed under a HEPA-filtered positive pressure PCR hood. An example of a programmable PCR cycling profile is as follows: 95° C. for 10 minutes, followed by 8 cycles of 95° C. for 20 sec, 62° C. for 20 sec, and 72° C. for 30 sec—wherein the 62° C. annealing step is decreased by 1° C. on each successive cycle of the 8 cycles, followed by 28 cycles of 95° C. for 20 sec, 55° C. for 20 sec, and 72° C. for 30 sec, followed by holding at 4° C. For multiplex reactions, in a preferred embodiment, PCR is carried out using 1 the Qiagen Multiplex PCR kit and buffers therein (Qiagen, Valencia, Calif.), which comprises 3 mM $MgCl_2$. 1 ng template DNA and 200 mM of each primer are used for a 40 µL reaction volume. The cycle conditions for an exemplary multiplex reaction are:

1-95 degree C 15 minutes
2-95 degree C 30 seconds
3-61 degree C 2 minutes (1-3 for 35 cycles)
4-72 degree C 30 seconds
5-72 degree C 10 minutes
6-60 degree C 30 minutes
7-4 degree C hold Development and optimization of PCR reactions is routine to one with ordinary skill in the art and can be accomplished without undue experimentation.

Example 2

Nucleic Acid Purification

Procedure for Semi-Automated Purification of a PCR Mixture Using Commercially Available ZipTips®—

As described by Jiang and Hofstadler (Y. Jiang and S. A. Hofstadler *Anal. Biochem.* 2003, 316, 50-57) an amplified nucleic acid mixture can be purified by commercially available pipette tips containing anion exchange resin. For pretreatment of ZipTips® AX (Millipore Corp. Bedford, Mass.), the following steps were programmed to be performed by an Evolution™ P3 liquid handler (Perkin Elmer) with fluids being drawn from stock solutions in individual wells of a 96-well plate (Marshall Bioscience): loading of a rack of ZipTips® AX; washing of ZipTips® AX with 15 µl of 10% $NH_4OH$/50% methanol; washing of ZipTips® AX with 15 µl of water 8 times; washing of ZipTips® AX with 15 µl of 100 mM $NH_4OAc$.

For purification of a PCR mixture, 20 µl of crude PCR product was transferred to individual wells of a MJ Research plate using a BioHit (Helsinki, Finland) multichannel pipette. Individual wells of a 96-well plate were filled with 300 µl of 40 mM $NH_4HCO_3$. Individual wells of a 96-well plate were filled with 300 µl of 20% methanol. An MJ research plate was filled with 10 µl of 4% $NH_4OH$. Two reservoirs were filled with deionized water. All plates and reservoirs were placed on the deck of the Evolution P3 (EP3) (Perkin-Elmer, Boston, Mass.) pipetting station in pre-arranged order. The following steps were programmed to be performed by an Evolution P3 pipetting station: aspiration of 20 µl of air into the EP3 P50 head; loading of a pre-treated rack of ZipTips® AX into the EP3 P50 head; dispensation of the 20 µl NH$_4$HCO$_3$ from the ZipTips® AX; loading of the PCR product into the ZipTips® AX by aspiration/dispensation of the PCR solution 18 times; washing of the ZipTips® AX containing bound nucleic acids with 15 µl of 40 mM NH$_4$ HCO$_3$ 8 times; washing of the ZipTips® AX containing bound nucleic acids with 15 µl of 20% methanol 24 times; elution of the purified nucleic acids from the ZipTips® AX by aspiration/dispensation with 15 µl of 4% NH$_4$OH 18 times. For final preparation for analysis by ESI-MS, each sample was diluted 1:1 by volume with 70% methanol containing 50 mM piperidine and 50 mM imidazole.

Solution Capture Purification of PCR products for Mass Spectrometry with Ion-Exchange Resin-Magnetic Beads—

The following procedure is disclosed in published U.S. Patent application US2005-0130196, filed on Sep. 17, 2004, which is commonly owned and incorporated herein by reference. For solution capture of nucleic acids with ion exchange resin linked to magnetic beads, 25 microliters of a 2.5 mg/mL suspension of BioClone amine-terminated supraparamagnetic beads are added to 25 to 50 microliters of a PCR or RT-PCR reaction containing approximately 10 pM of a typical PCR amplification product. The suspension is mixed for approximately 5 minutes by votexing, pipetting or shaking, after which the liquid is removed following use of a magnetic separator to separate magnetic beads. The magnetic beads containing the amplification product are then washed 3 times with 50 mM ammonium bicarbonate/50% methanol or 100 mM ammonium bicarbonate/50% methanol, followed by three additional washes with 50% methanol. The bound PCR amplicon is eluted with electrospray-compatible elution buffer comprising 25 mM piperidine, 25 mM imidazole, 35% methanol, which can also comprise calibration standards. Steps of this procedure can be performed in multi-well plates and using a liquid handler, for example the Evolution™ P3 liquid handler and/or under the control of a robotic arm. The eluted nucleic acids in this condition are amenable to analysis by ESI-MS. The time required for purification of samples in a single 96-well plate using a liquid handler is approximately five minutes.

Example 3

Mass Spectrometry

The ESI-FTICR mass spectrometer used is a Bruker Daltonics (Billerica, Mass.) Apex II 70e electrospray ionization Fourier transform ion cyclotron resonance mass spectrometer (ESI-FTICR-MS) that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics can operate in close proximity to the ESI-FTICR mass spectrometer. All aspects of pulse sequence control and data acquisition are performed on a 1.1 GHz Pentium II data station running Broker's Xmass software. 20 µL sample aliquots are extracted directly from 96-well microtiter plates using a CTC HTS PAL autosampler (LEAP Technologies, Carrboro, N.C.) triggered by the data station. Samples are injected directly into the ESI source at a flow rate of 75 µL/hr. Ions are formed via electrospray ionization in a modified Analytica (Branford, Conn.) source employing an off axis, grounded electrospray probe positioned ca. 1.5 cm from the metalized terminus of a glass desolvation capillary. The atmospheric pressure end of the glass capillary is biased at 6000 V relative to the ESI needle during data acquisition. A countercurrent flow of dry N$_2$/O$_2$ is employed to assist in the desolvation process. Ions are accumulated in an external ion reservoir comprised of an rf-only hexapole, a skimmer cone, and an auxiliary gate electrode, prior to injection into the trapped ion cell where they are mass analyzed.

Spectral acquisition is performed in the continuous duty cycle mode whereby ions are accumulated in the hexapole ion reservoir simultaneously with ion detection in the trapped ion cell. Following a 1.2 ms transfer event, in which ions are transferred to the trapped ion cell, the ions are subjected to a 1.6 ms chirp excitation corresponding to 8000-500 m/z. Data was acquired over an m/z range of 500-5000 (1M data points over a 225K Hz bandwidth). Each spectrum is the result of co-adding 32 transients. Transients are zero-filled once prior to the magnitude mode Fourier transform and post calibration using the internal mass standard. The ICR-2LS software package (G. A. Anderson, J. E. Bruce (Pacific Northwest National Laboratory, Richland, Wash., 1995) is used to deconvolute the mass spectra and calculate the mass of the monoisotopic species using an "averaging" fitting routine (M. W. Senko, S. C. Beu, F. W. McLafferty, *J. Am. Soc. Mass Spectrom.* 1995, 6, 229) modified for DNA. Using this approach, monoisotopic molecular weights are calculated.

The ESI-TOF mass spectrometer used is based on a Bruker Daltonics MicroTOF™. Ions from the ESI source undergo orthogonal ion extraction and are focused in a reflectron prior to detection. The TOF is equipped with the same automated sample handling and fluidics as described for the FTICR above. Ions are formed in the standard MicroTOF™ ESI source that is equipped with the same off-axis sprayer and glass capillary as the FTICR ESI source. Consequently, source conditions are the same as those described above. External ion accumulation is also employed to improve ionization duty cycle during data acquisition. Each detection event on the TOF comprises 75,000 data points digitized over 75 µs.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer is injected at a high flow rate to rinse the transfer line and spray needle to avoid sample contamination/carryover. Following the rinse step, the autosampler injects the next sample and the flow rate is switched to low flow. Following a brief equilibration delay, data acquisition begins. As spectra are co-added, the autosampler continues rinsing the syringe and picking up buffer to rinse the injector and sample transfer line. In general, two syringe rinses and one injector rinse are required to minimize sample carryover. During a routine screening protocol, a new sample mixture is injected every 106 seconds. A fast wash station for the syringe needle has also been implemented which, when combined with shorter acquisition times, facilitates the acquisition of mass spectra at a rate of just under one spectrum per minute.

Raw mass spectra are post-callibrated with an internal mass standard and deconvoluted to monoisotopic molecular masses. Unambiguous base compositions are derived from the exact mass measurement of the complementary single-stranded oligonucleotides. Quantitative results are obtained by comparing the peak heights with an internal PCR calibration standard present in every PCR well at 500 molecules per well. Calibration methods are commonly owned and dis-

Example 4

De Novo Determination of Base Composition of Amplification Products Using Molecular Mass Modified Deoxynucleotide Triphosphates Because the molecular masses of the four natural nucleotides have a relatively narrow molecular mass range (A=313.058, G=329.052, C=289.046, T=304.046 See Table 2), a persistent source of ambiguity in assignment of base composition can occur as follows: two nucleic acid strands having different base composition may have a difference of about 1 Da when the base composition difference between the two strands is $G \leftrightarrow A$ (−15.994) combined with $C \leftrightarrow T$ (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052. A 1 Da difference in molecular mass may be within the experimental error of a molecular mass measurement and thus, the relatively narrow molecular mass range of the four natural nucleotides imposes an uncertainty factor.

The present example provides for a means for removing this theoretical 1 Da uncertainty factor through amplification of a nucleic acid with one mass-tagged nucleotide and three natural nucleotides.

Addition of significant mass to one of the 4 nucleotides (dNTPs) in an amplification reaction, or in the primers themselves, will result in a significant difference in mass of the resulting amplification product (significantly greater than 1 Da) arising from ambiguities arising from the $G \leftrightarrow A$ combined with $C \leftrightarrow T$ event (Table 1). Thus, the same the $G \leftrightarrow A$ (−15.994) event combined with 5-Iodo-$C \leftrightarrow T$ (−110.900) event would result in a molecular mass difference of 126.894. If the molecular mass of the base composition $A_{27}G_{30}$ 5-Iodo-$C_{21}T_{21}$ (33422.958) is compared with $A_{26}G_{31}$5-Iodo-$C_{22}T_{20}$, (33549.852) the theoretical molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 2

Molecular Masses of Natural Nucleotides and the Mass-Modified Nucleotide 5-Iodo-C and Molecular Mass Differences Resulting from Transitions

| Nucleotide | Molecular Mass | Transition | Δ Molecular Mass |
|---|---|---|---|
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Example 5

Data Processing

Mass spectra of amplification products are analyzed independently using a maximum-likelihood processor, such as is widely used in radar signal processing, which is described in U.S. Patent Application 20040209260, which is incorporated herein by reference in entirety. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

One of ordinary skill in the art will recognize that the signal processing methodologies of this example can be used in the context of the methods of STR analysis described herein.

Example 6

Amplification of Nucleic Acids with Isotope Depleted dNTPs

Due to the natural abundance of .sub.13C and other heavy isotopes in biological macromolecules, exact mass measurements are more difficult at increasing molecular weight. Additionally, the width of the isotopic distribution is inherently broader at high molecular weight thus making accurate monoisotopic molecular weight measurements difficult. There is also an inherent sensitivity loss as signals from a single amplicon are spread over more and more isotope peaks. An analogous problem occurs with ESI-MS analysis of proteins.

Isotope-depleted dNTPs suitable for use in PCR reactions can be produced from bacteria grown in isotope-depleted media in which the primary carbon source is .sub.13C depleted glucose and $^{15}$N depleted ammonium sulfate. Once the bacteria are grown to critical density, the isotope-depleted genomic DNA is extracted. DNA is then digested to mononucleotides from which deoxynucleotide triphosphates are enzymatically synthesized. In this manner, it should be possible to produce isotope-depleted reagents at modest cost. Proof-of-principle for this approach was recently published by Tang and coworkers (Tang et al., Anal. Chem., 2002, 74, 226-231). We expect that generating isotope depleted PCR products will result in a 3-5 fold improvement in sensitivity (as the signal is spread over fewer isotope peaks). More importantly, this approach should relieve the spectral congestion observed in the mass spectra and reduce the extent that species of similar mass or m/z produce overlapping MS peaks.

Example 7

Design of Primer Pairs for Forensic DNA typing/Human Identity Testing

Figure 1B:
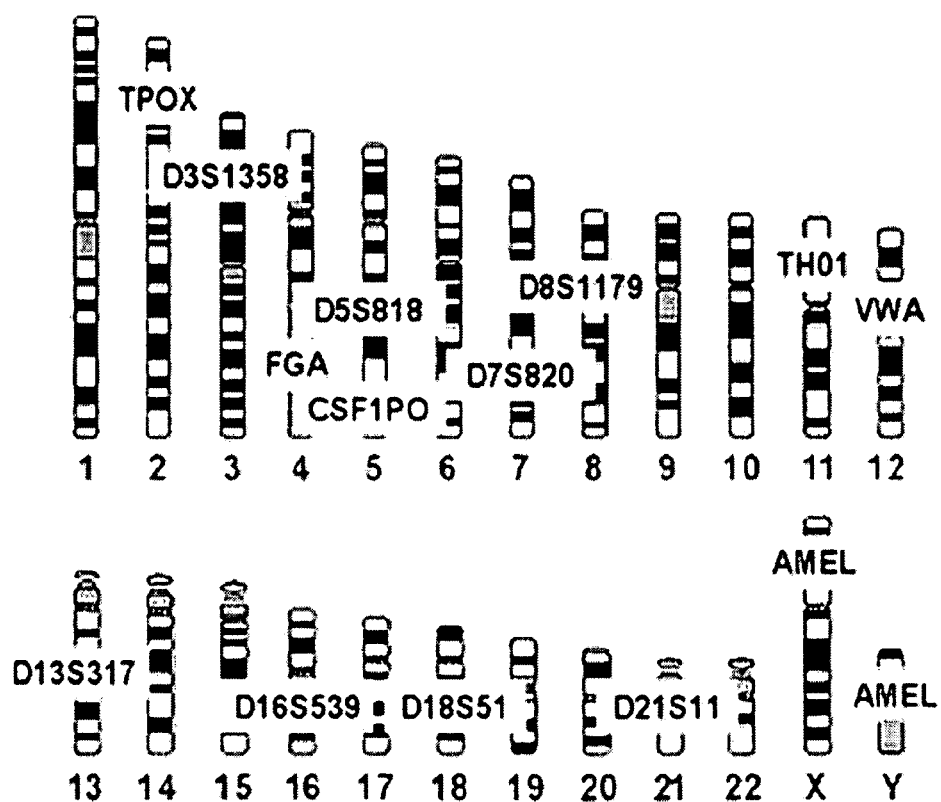
FIG. 1b is an illustration of the FBI 13 core CODIS STR loci plus amelogenin (AMEL), which is used for sex-discrimination. The name of each locus is pictured centered on the chromosome where it is found. Reference alleles are available for the loci from GenBank.
Figure 2:
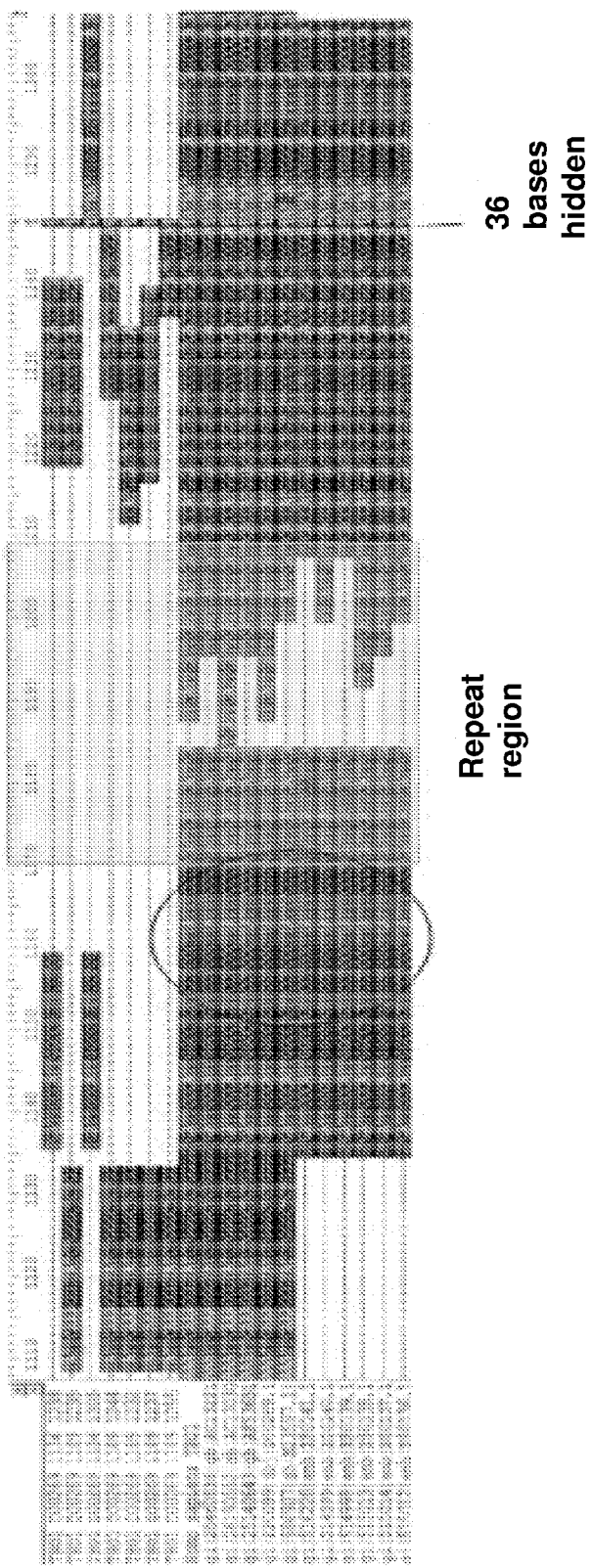
FIG. 2 Shows an illustrated example of selection of STR-typing primer pairs for the TH01 locus. Primer pairs are selected to hybridize to regions adjacent or in close proximity to the variable region, which is designated here as the repeat region and in this example represents the STR repeat region.

FIG. 1a is a flow diagram outlining the general approach for STR assay development, including primer design. Primers were designed against each of the 13 core CODIS loci and amelogenin (illustrated in FIG. 1b) according to the procedure outlined in this figure. Allele reference sequences were obtained for each STR locus from the publicly available the Short Tandem Repeat Internet Database (STRBase) and multiple primers designed for each STR locus. The multiple primers were designed to hybridize to conserved sequence regions adjacent or nearly adjacent (in close proximity) to the STR repeat. For example, Table 3 lists several primers designed (as shown in FIG. 2) to hybridize within conserved regions flanking the TH01 (also called HUMTH01) STR locus. These primers are also listed in Table 5. Table 3 shows the length of expected amplicons when allele 9 is amplified with the respective primer pairs, and the expected range of amplicons based on characterized alleles.

TABLE 3

Primer Pair Selection for HUMTH01 STR Locus

| Primer Pair Number | Primer Pair Name | Forward SEQ ID NO | Reverse SEQ ID NO | Length on Allele 9 | Expected Length Range |
|---|---|---|---|---|---|
| 1194 | TH01_D00269_1136_1238 | 14 | 82 | 103 | 79-123 |
| 1195 | TH01_D00269_1109_1238 | 15 | 83 | 130 | 106-150 |
| 1196 | TH01_D00269_1136_1305 | 16 | 84 | 170 | 146-190 |
| 1197 | TH01_D00269_1109_1244 | 17 | 85 | 136 | 112-156 |
| 1198 | TH01_D00269_1109_1232 | 18 | 86 | 124 | 100-144 |
| 1199 | TH01_D00269_1109_1237 | 19 | 87 | 129 | 105-149 |
| 1200 | TH01_D00269_1109_1255 | 20 | 88 | 147 | 123-167 |

Figure 3:
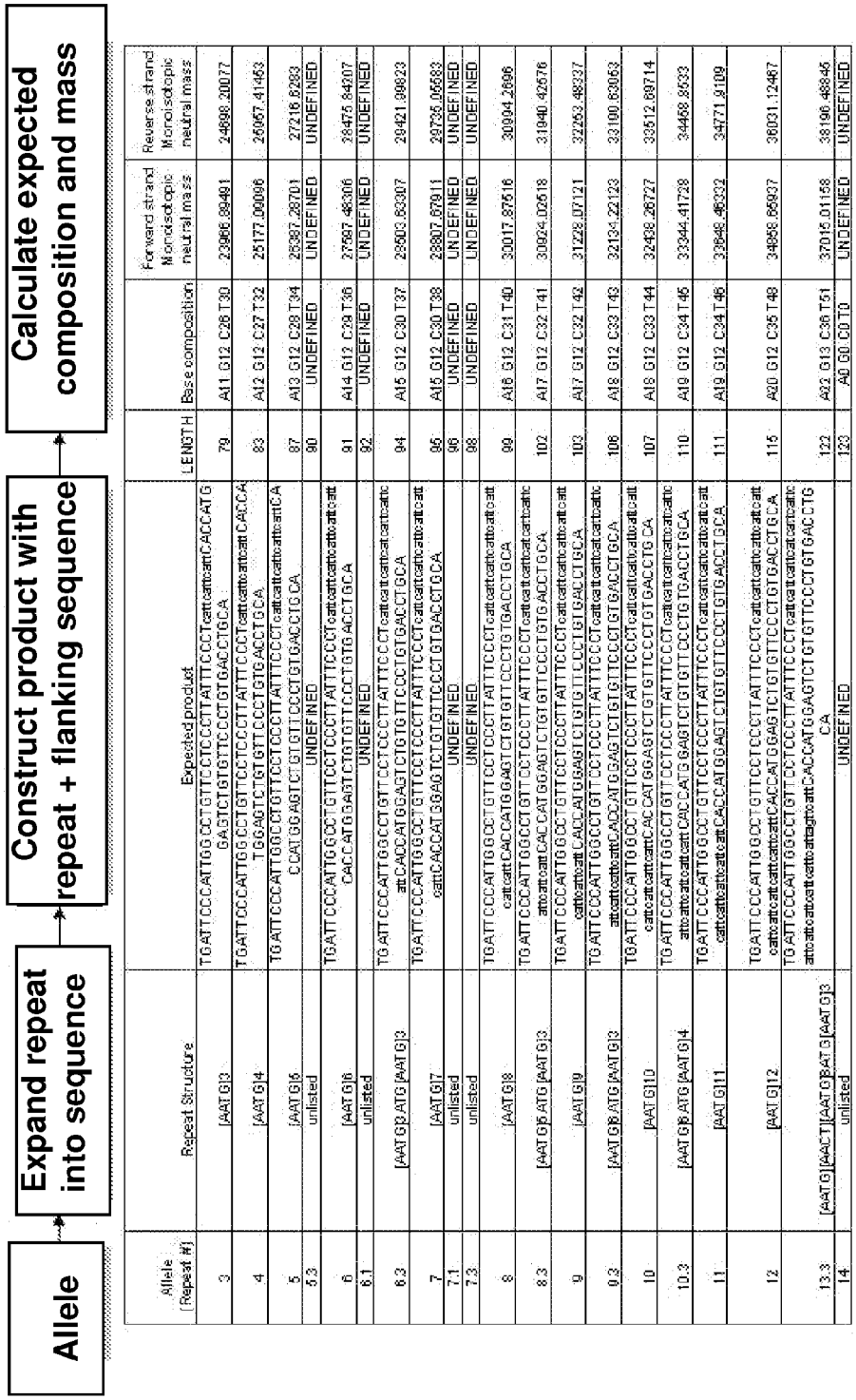
FIG. 3 is an example of a database constructed for a primer pair designed to hybridize to conserved regions of the TH01 locus. Characterized alleles were obtained from GenBank. For each allele, an STR-identifying amplicon was generated in silico by constructing a sequence comprising the repeat locus for the allele and the flanking sequences to which the primers of the pair bind.

As exemplified for TH01 in FIG. 3, repeat structures (unit of repeated sequence) for each STR locus were then used to construct a database comprising expected masses and base compositions of expected STR-identifying amplicons comprising the variable region (repeated sequences) and the flanking sequences to which the primers hybridize for each characterized allele. The base compositions and molecular masses were indexed to the primer pairs and alleles in the database.

Table 4 displays the reference alleles used to design primers for each of the 13 CODIS STR and AMEL loci, along with the corresponding GenBank Accession number. Minimum and maximum product lengths were calculated using all characterized alleles.

TABLE 4

Reference Alleles and Expected Amplicon Lengths for Primer Pair Design to CODIS STRs/AMEL

| Locus | Reference Allele | Reference GB Accession Number | Length of amplicons (Range) |
|---|---|---|---|
| CSF1PO | 5 | U63963 | 133-178 |
| D13S317 | 5 | G09017 | 124-138 |
| D16S539 | 4 | G07925 | 116-144 |
| D18S51 | 4 | AP001534 | 168-183 |
| D21S11 | 2 | M84567 | 208-214 |
| D3S1358 | 3 | NT086638 | 99-122 |
| D5S818 | 4 | G08446 | 145-159 |
| D7S820 | 5 | G08616 | 135-166 |
| D8S1179 | 3 | G08710 | 109-114 |
| FGA | 2 | M64982 | 149-163 |
| TH01 | 7 | D00269 | 103-170 |
| TPOX | 8 | M68651 | 108-180 |
| vWA | 3 | M25858 | 141-158 |
| AMEL | 3 | M55418 | 83-111 |

Primer pairs designed to the 13 CODIS STR alleles and AMEL are listed in Table 5. The forward and reverse primer names in this table follow standard primer pair naming as described above.

TABLE 5

Primer Pairs Designed for Use in Human STR DNA Analysis

| PRIMER PAIR NUMBER | FORWARD PRIMER NAME | FWD SEQ ID NO. | FORWARD PRIMER SEQUENCE | REVERSE PRIMER NAME | REVERSE PRIMER SEQEUENCE | REV SEQ ID NO. |
|---|---|---|---|---|---|---|
| 1183 | VWA_M25858_1650_1681_F | 1 | TGGGGAGAATAATCAGTATGTGACTTGGATTG | VWA_M25858_1756_1790_R | TGGGTGATAAATACATAGGATGGATGGATAGATGG | 52 |
| 1184 | VWA_M25858_1641_1677_F | 2 | TCTAGTGGATGATAAGAATAATCAGTATGTGACTTGG | VWA_M25858_1760_1795_R | TAGGACAGATGATAAATACATAGGATGGATGGATAG | 53 |
| 1185 | VWA_M25858_1638_1671_F | 3 | TGCCCTAGTGGATGATAAGAATAATCAGTATGTG | VWA_M25858_1764_1795_R | TGGGACAGATGATAAATACATAGGATGGATGG | 54 |
| 2823 | VWA_M25858_1651_1681_F | 4 | GGGGAGAATAATCAGTATGTGACTTGGATTG | VWA_M25858_1756_1789_R | GGGTGATAAATACATAGGATGGATGGATAGATGG | 55 |
| 1186 | TPOX_M68651_1840_1863_F | 5 | TGGCACAGAACAGGCACTTAGGGA | TPOX_M68651_1933_1955_R | TAGGCCCTTCTGTCCTTGTCAGC | 56 |
| 1187 | TPOX_M68651_1840_1863_F | 5 | TGGCACAGAACAGGCACTTAGGGA | TPOX_M68651_1922_1947_R | TCTGTCCTTGTCAGCGTTTATTTGCC | 57 |
| 1188 | TPOX_M68651_1840_1863_F | 5 | TGGCACAGAACAGGCACTTAGGGA | TPOX_M68651_1965_1988_R | TGTGCGCTGGTCTTACTCCTGTTC | 58 |
| 1189 | TPOX_M68651_1840_1863_F | 5 | TGGCACAGAACAGGCACTTAGGGA | TPOX_M68651_1992_2016_R | TCCCAGGTCTTCTGAACACAAGTCG | 59 |
| 1190 | TPOX_M68651_1837_1861_F | 6 | TACTGGCACAGAACAGGCACTTAGG | TPOX_M68651_1933_1955_R | TAGGCCCTTCTGTCCTTGTCAGC | 56 |
| 1191 | TPOX_M68651_1837_1861_F | 6 | TACTGGCACAGAACAGGCACTTAGG | TPOX_M68651_1922_1947_R | TCTGTCCTTGTCAGCGTTTATTTGCC | 57 |
| 1192 | TPOX_M68651_1837_1861_F | 6 | TACTGGCACAGAACAGGCACTTAGG | TPOX_M68651_1965_1988_R | TGTGCGCTGGTCTTACTCCTGTTC | 58 |
| 1193 | TPOX_M68651_1837_1861_F | 6 | TACTGGCACAGAACAGGCACTTAGG | TPOX_M68651_1992_2016_R | TCCCAGGTCTTCTGAACACAAGTCG | 59 |
| 2822 | TPOX_M68651_1841_1863_F | 7 | GGCACAGAACAGGCACTTAGGGA | TPOX_M68651_1922_1947_2_R | GGTGTCCTTGTCAGCGTTTATTTGCC | 60 |
| 1194 | THO1_D00269_1136_1159_F | 8 | TGATTCCCATTGGCCTGTTCCTCC | THO1_D00269_1216_1238_R | TGCAGGTCACAGGGAACACAGAC | 61 |
| 1195 | THO1_D00269_1109_1133_F | 9 | TATTCAAAGGGTATCTGGGCTCTGG | THO1_D00269_1216_1238_R | TGCAGGTCACAGGGAACACAGAC | 61 |
| 1196 | THO1_D00269_1136_1159_F | 8 | TGATTCCCATTGGCCTGTTCCTCC | THO1_D00269_1281_1305_R | TGTGGGCTGAAAAGCTCCCGATTAT | 62 |
| 1197 | THO1_D00269_1109_1133_F | 9 | TATTCAAAGGGTATCTGGGCTCTGG | THO1_D00269_1224_1244_R | TCCGAGTGCAGGTCACAGGGA | 63 |

TABLE 5-continued

Primer Pairs Designed for Use in Human STR DNA Analysis

| PRIMER PAIR NUMBER | FORWARD PRIMER NAME | FWD SEQ ID NO. | FORWARD PRIMER SEQUENCE | REVERSE PRIMER NAME | REVERSE PRIMER SEQEUENCE | REV SEQ ID NO. |
|---|---|---|---|---|---|---|
| 1198 | THO1_D00269_1109_1133_F | 9 | TATTCAAAGGGTATCTGGGCTCTGG | THO1_D00269_1209_1232_R | TCACAGGGAACACAGACTCCATGG | 64 |
| 1199 | THO1_D00269_1109_1133_F | 9 | TATTCAAAGGGTATCTGGGCTCTGG | THO1_D00269_1214_1237_R | TCAGGTCACAGGGAACACAGACTC | 65 |
| 1200 | THO1_D00269_1109_1133_F | 9 | TATTCAAAGGGTATCTGGGCTCTGG | THO1_D00269_1234_1255_R | TACACAGGGCTTCCGAGTGCAG | 66 |
| 2856 | THO1_D00269_1107_1133_F | 10 | GGAAATCAAAGGGTATCTGGGCTCTGG | THO1_D00269_1216_1238_2_R | CGCTGGTCACAGGGAACACAGAC | 67 |
| 1201 | FGA_M64982_2868_2892_F | 11 | TCCCTTAGGCATATTTACAAGCTAG | FGA_M64982_2995_3016_R | TGATTTGTCTGTAATTGCCAGC | 68 |
| 1202 | FGA_M64982_2858_2892_F | 12 | TCCCCAAAATAAAATTAGGCATATTTACAAGCTAG | FGA_M64982_2995_3020_R | TGAGTGATTTGTCTGTAATTGCCAGC | 69 |
| 1203 | D21S11_M84567_125_143_F | 13 | TGTGAGTCAATTCCCCAAG | D21S11_M84567_308_332_R | TATGTTGTATTAGTCAATGTTCTCC | 70 |
| 1204 | D21S11_M84567_127_151_F | 14 | TGAGTCAATTCCCCAAGTGAATTGC | D21S11_M84567_308_340_R | TCCCTAAAGATGTTGTATTAGTCAATGTTCTCC | 71 |
| 1205 | D18S51_AP001534_85734_85766_F | 15 | TGTGGAGATGTCTTACAATAACAGTTGCTACTA | D18S51_AP001534_85874_85901_R | TCTGAGTGACAAATTGAGACCTTGTCTC | 72 |
| 1206 | D18S51_AP001534_85734_85766_F | 15 | TGTGGAGATGTCTTACAATAACAGTTGCTACTA | D18S51_AP001534_85878_85906_R | TTCACTCTGAGTGACAAATTGAGACCTTG | 73 |
| 1207 | D18S51_AP001534_85724_85750_F | 16 | TTCTCTGGTGTGTGGAGATGTCTTACA | D18S51_AP001534_85874_85901_R | TCTGAGTGACAAATTGAGACCTTGTCTC | 72 |
| 1208 | D18S51_AP001534_85724_85750_F | 16 | TTCTCTGGTGTGTGGAGATGTCTTACA | D18S51_AP001534_85878_85906_R | TTCACTCTGAGTGACAAATTGAGACCTTG | 73 |
| 1209 | D16S539_G07925_226_252_F | 17 | TCCCAAGCTCTTCCTCTTCCCTAGATC | D16S539_G07925_335_369_R | TGCATCTGTAAGCATGTATCTATCATCCATCTCTG | 74 |
| 1210 | D16S539_G07925_234_263_F | 18 | TCTTCCTCTTCCCTAGATCAATACAGACAG | D16S539_G07925_320_349_R | TACCATCCATCTCTGTTTTGTCTTTCAATG | 75 |
| 1211 | D16S539_G07925_220_244_F | 19 | TGCAGATCCCAAGCTCTTCCTCTTC | D16S539_G07925_320_355_R | TGGATCTATCATCCATCTCTGTTTTGTCTTTCAATG | 76 |
| 1212 | D16S539_G07925_230_257_F | 20 | TAGCTCTTCCTCTTCCCTAGATCAATAC | D16S539_G07925_320_347_R | TCATCCATCTCTGTTTTGTCTTTCAATG | 77 |

TABLE 5-continued

Primer Pairs Designed for Use in Human STR DNA Analysis

| PRIMER PAIR NUMBER | FORWARD PRIMER NAME | FWD SEQ ID NO. | FORWARD PRIMER SEQUENCE | REVERSE PRIMER NAME | REVERSE PRIMER SEQEUENCE | REV SEQ ID NO. |
|---|---|---|---|---|---|---|
| 2820 | D16S539_G07925_232_262_F | 21 | GCTCTTCCTCTTCCCTAGATCAATACAGACA | D16S539_G07925_320_351_R | GCTACCATCCATCTCTGTTTTGTCTTTCAATG | 78 |
| 1213 | D13S317_G09017_84_111_F | 22 | TGGACTCTGACCCATCTAACGCCTATCT | D13S317_G09017_204_228_R | TGAGCCATAGGCAGCCCAAAAAGAC | 79 |
| 1214 | D13S317_G09017_89_119_F | 23 | TCTGACCCATCTAACGCCTATCTGTATTTAC | D13S317_G09017_198_221_R | TAGGCAGCCCAAAAAGACAGACAG | 80 |
| 1215 | D13S317_G09017_95_125_F | 24 | TCATCTAACGCCTATCTGTATTTACAAATAC | D13S317_G09017_198_218_R | TCAGCCCAAAAGACAGACAG | 81 |
| 1216 | D13S317_G09017_84_110_F | 25 | TGGACTCTGACCCATCTAACGCCTATC | D13S317_G09017_196_221_R | TAGGCAGCCCAAAAAGACAGACAGAA | 82 |
| 1217 | D13S317_G09017_93_124_F | 26 | TCCCATCTAACGCCTATCTGTATTTACAAATA | D13S317_G09017_206_228_R | TGAGCCATAGGCAGCCCAAAAG | 83 |
| 2819 | D13S317_G09017_88_119_F | 27 | CTCTGACCCATCTAACGCCTATCTGTATTTAC | D13S317_G09017_198_222_R | GTAGGCAGCCCAAAAAGACAGACAG | 84 |
| 1218 | D8S1179_G08710_17_41_F | 28 | TTTTTGTATTTCATGTGTACATTCG | D8S1179_G08710_97_121_R | TATCCTGTAGATTATTTTCACTGTG | 85 |
| 1219 | D8S1179_G08710_17_41_2_F | 29 | TCCCTGTATTTCATGTGTACATTCG | D8S1179_G08710_97_125_R | TCCCTATCCTGTAGATTATTTTCACTGTG | 86 |
| 1220 | D8S1179_G08710_16_41_F | 30 | TCCCTTGTATTTCATGTGTACATTCG | D8S1179_G08710_96_125_R | TACCTATCCTGTAGATTATTTTCACTGTGG | 87 |
| 2818 | D8S1179_G08710_14_45_F | 31 | GGGGTTTTGTATTTCATGTGTACATTCGTATC | D8S1179_G08710_96_128_R | GGGTACCTATCCTGTAGATTATTTTCACTGTGG | 88 |
| 1221 | D7S820_G08616_93_121_F | 32 | TAGAACACTTGTCATAGTTTAGAACGAAC | D7S820_G08616_231_258_R | TCATTGACAGAATTGCACCAAATATTGG | 89 |
| 1222 | D7S820_G08616_93_121_F | 32 | TAGAACACTTGTCATAGTTTAGAACGAAC | D7S820_G08616_198_227_R | TCGGGTGTTTACTATAGACTATTTAGTGAG | 90 |
| 1223 | D7S820_G08616_93_126_F | 33 | TGGAACACTTGTCATAGTTTAGAACGAACTAACG | D7S820_G08616_198_230_R | TGGCCGGGTGTTTACTATAGACTATTTAGTGAG | 91 |
| 1224 | D7S820_G08616_90_118_F | 34 | TGATAGAACACTTGTCATAGTTTAGAACG | D7S820_G08616_198_227_R | TCGGGTGTTTACTATAGACTATTTAGTGAG | 90 |

TABLE 5-continued

Primer Pairs Designed for Use in Human STR DNA Analysis

| PRIMER PAIR NUMBER | FORWARD PRIMER NAME | FWD SEQ ID NO. | FORWARD PRIMER SEQUENCE | REVERSE PRIMER NAME | REVERSE PRIMER SEQEUENCE | REV SEQ ID NO. |
|---|---|---|---|---|---|---|
| 1225 | D7S820_G08616_90_118_F | 34 | TGATAGAACACTTGTCATAGTTTAGAACG | D7S820_G08616_221_252_R | TCAGAATTGCACCAAATATTGGTAATTAAATG | 92 |
| 2817 | D7S820_G08616_93_123_F | 35 | GGGAACACTTGTCATAGTTTAGAACGAACTA | D7S820_G08616_196_229_R | CCCGGAATGTTTACTATAGACTATTTAGTGAGAT | 93 |
| 1226 | D5S818_G08446_64_93_F | 36 | TGACAAGGGTGATTTTCCTCTTTGGTATCC | D5S818_G08446_189_222_R | TCCAATCATAGCCACAGTTTACAACATTTGTATC | 94 |
| 1227 | D5S818_G08446_70_102_F | 37 | TGGTGATTTCCTCTTTGGTATCCTTATGTAAT | D5S818_G08446_191_220_R | TGGTCATAGCCACAGTTTACAACATTTGTA | 95 |
| 1228 | D5S818_G08446_70_93_F | 38 | TGGTGATTTCCTCTTTGGTATCC | D5S818_G08446_188_214_R | TAGCCACAGTTTACAACATTTGTATCT | 96 |
| 1229 | D5S818_G08446_69_93_F | 39 | TGGGTGATTTTCCTCTTTGGTATCC | D5S818_G08446_189_217_R | TCATAGCCACAGTTTACAACATTTGTATC | 97 |
| 2816 | D5S818_G08446_70_102_2_F | 40 | GGGTGATTTCCTCTTTGGTATCCTTATGTAAT | D5S818_G08446_191_222_R | GCCAATCATAGCCACAGTTTACAACATTTGTA | 98 |
| 1230 | D3S_NT086638_5793093_5793118_F | 41 | TCATGAAATCAACAGAGGCTTGCATG | D3S_NT086638_5793169_5793191_R | TGACAGAGCAAGACCCTGTCTCA | 99 |
| 1231 | D3S_NT086638_5793090_5793116_F | 42 | TACTCATGAAATCAACAGAGGCTTGCA | D3S_NT086638_5793188_5793209_R | TGTGACAGAGCAAGACCCTGTC | 100 |
| 1232 | D3S_NT086638_5793090_5793116_F | 42 | TACTCATGAAATCAACAGAGGCTTGCA | D3S_NT086638_5793190_5793211_R | TGGGTGACAGAGCAAGACCCTG | 101 |
| 1233 | CSF1PO_U63963_11884_11909_F | 43 | TCCTGTGTCTCAGTTTTCCTACCTG | CSF1PO_U63963_12038_12061_R | TGCACACTTGGACAGCATTTCCTG | 102 |
| 1234 | CSF1PO_U63963_11910_11940_F | 44 | TGGGATGAAGATATTAACAGTAACTGCCTTC | CSF1PO_U63963_12016_12042_R | TCCTGTGTCAGACCCTGTTCTAAGTAC | 103 |
| 1235 | CSF1PO_U63963_11895_11930_F | 45 | TCAGTTTTCCTACCTGTAAAATGAAGATATTAACAG | CSF1PO_U63963_12016_12042_R | TCCTGTGTCAGACCCTGTTCTAAGTAC | 103 |
| 1236 | CSF1PO_U63963_11879_11907_F | 46 | TAACCACCCTGTGTCTCAGTTTTCCTACC | CSF1PO_U63963_12030_12054_R | TTGGACAGCATTTCCTGTGTCAGAC | 104 |
| 1237 | CSF1PO_U63963_11879_11907_F | 46 | TAACCACCCTGTGTCTCAGTTTTCCTACC | CSF1PO_U63963_12016_12042_R | TCCTGTGTCAGACCCTGTTCTAAGTAC | 103 |

TABLE 5-continued

Primer Pairs Designed for Use in Human STR DNA Analysis

| PRIMER PAIR NUMBER | FORWARD PRIMER NAME | FWD SEQ ID NO. | FORWARD PRIMER SEQUENCE | REVERSE PRIMER NAME | REVERSE PRIMER SEQEUENCE | REV SEQ ID NO. |
|---|---|---|---|---|---|---|
| 2815 | CSF1PO_U63963_11911_11943_F | 47 | GGCATGAAGATATTAACAGTAACTGCCTTCATA | CSF1PO_U63963_12011_12038_R | GTGTCAGACCCTGTTCTAAGTACTTCCT | 104 |
| 1238 | AMEL_M55418_285_310_F | 48 | TGCCCTGGGCTCTGTAAAGAATAGTG | AMEL_M55418_369_395_R | TCCATCAGAGCTTAAACTGGGAAGCTG | 105 |
| 1239 | AMEL_M55418_279_304_F | 49 | TAACAATGCCCTGGGCTCTGTAAAGA | AMEL_M55418_344_370_R | TGGTGGTAGGAACTGTAAAATCAGGAC | 106 |
| 1240 | AMEL_M55418_285_309_F | 50 | TGCCCTGGGCTCTGTAAAGAATAGT | AMEL_M55418_341_367_R | TGGTAGGAACTGTAAAATCAGGACCAC | 107 |
| 2824 | AMEL_M55418_286_310_F | 51 | GCCCTGGGCTCTGTAAAGAATAGTG | AMEL_M55418_369_394_R | GCATCAGAGCTTAAACTGGGAAGCTG | 108 |
| 3390 | D21S11_M84567_137_157_F | 109 | CCCCAAGTGAATTGCCTTCTA | D21S11_M84567_259_288_2_R | GGTAGATAGACTGGATAGATAGACGATAGA | 117 |
| 3391 | D21S11_M84567_137_159_F | 110 | CCCCAAGTGAATTGCCTTCTATC | D21S11_M84567_260_288_R | GGTAGATAGACTGGATAGATAGACGATAG | 118 |
| 3392 | FGA_M64982_2868_2892_2_F | 111 | GCCCTTAGGCATATTTACAAGCTAG | FGA_M64982_2995_3017_R | GTGATTTGTCTGTAATTGCCAGC | 119 |
| 3393 | FGA_M64982_2867_2894_2_F | 112 | CCCAATTAGGCATATTTACAAGCTAGTT | FGA_M64982_2985_3010_R | GTCTGTAATTGCCAGCAAAAAGAAA | 120 |
| 3394 | D18S51_AP001534_85740_85771_F | 113 | GATGTCTTACAATAACAGTTGCTACTATTTCT | D18S51_AP001534_85876_85900_R | CTGAGTGACAAATTGAGACCTTGTC | 121 |
| 3395 | D18S51_AP001534_85735_85766_F | 114 | GTGGAGATGTCTTACAATAACAGTTGCTACTA | D18S51_AP001534_85874_85902_R | CTCTGAGTGACAAATTGAGACCTTGTCTC | 122 |
| 3396 | D3S_NT086638_5793092_5793116_F | 115 | CTCATGAAATCAACAGAGGCTTGCA | D3S_NT086638_5793188_5793209_2_R | GGTGACAGAGCAAGACCCTGTC | 123 |
| 3397 | D3S_NT086638_5793097_5793121_F | 116 | GAAATCAACAGAGGCTTGCATGTAT | D3S_NT086638_5793184_5793206_R | GACAGAGCAAGACCCTGTCTCAT | 124 |

Example 8

Initial Primer Pair Testing Using PCR and Mass Spectrometry

Figure 7:
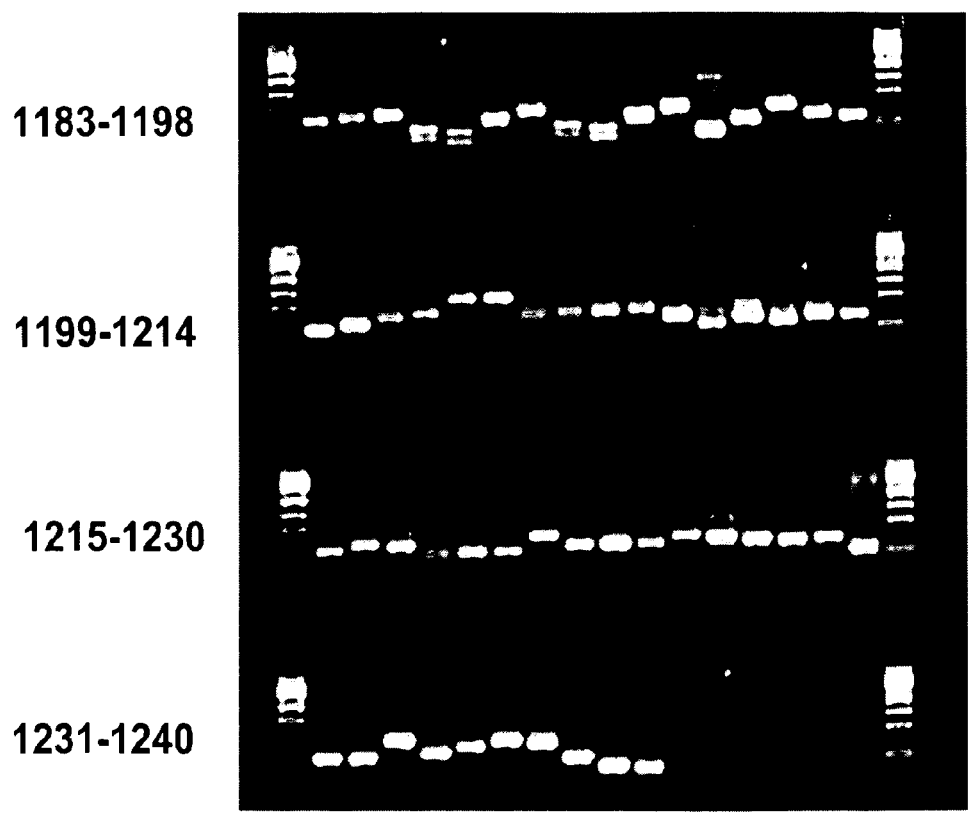
FIG. 7 is a picture of a 4% agarose gel separation of the PCR amplification reactions run during primer pair initial testing on the Seracare blood sample N31773 with the indicated primer pairs which are also listed in Table 5.

Initial primer testing was carried out using standard PCR reactions and the methods described herein. In one example, for initial testing, the template was 10-20 ng DNA from an internal standard: Seracare blood sample N31773. 50 µL reaction samples (1.5 mM MgCl2, 400 mM betaine, 200 µM each dNTP, 250 µM each primer and 4 units Amplitaq Gold™) were subject 35 cycles with a 54 degree C. annealing temperature, and resolved on a 4% agarose gel and preferred primers chosen for further analysis (shown in FIG. 7).

Figure 4:
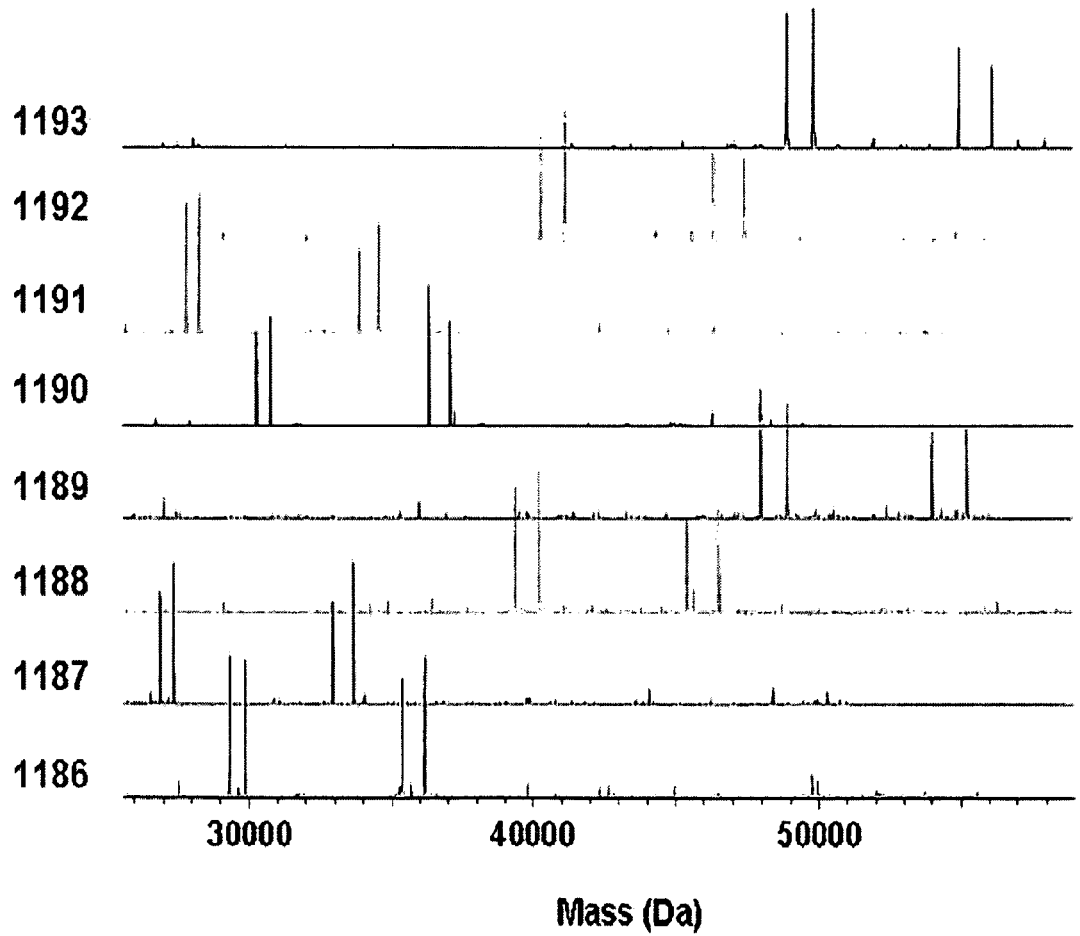
FIG. 4 is an example of mass spectrometry data generated using the methods provided herein for a sample (Seracare blood sample N31773) using the primer pairs listed by number (which are also listed in table 5), which all target the TPOX STR locus. The observed bi-allelic pattern is consistent among the different primer pairs, suggesting that each pair was able to resolve the molecular mass of alleles in the sample.
Figure 5:
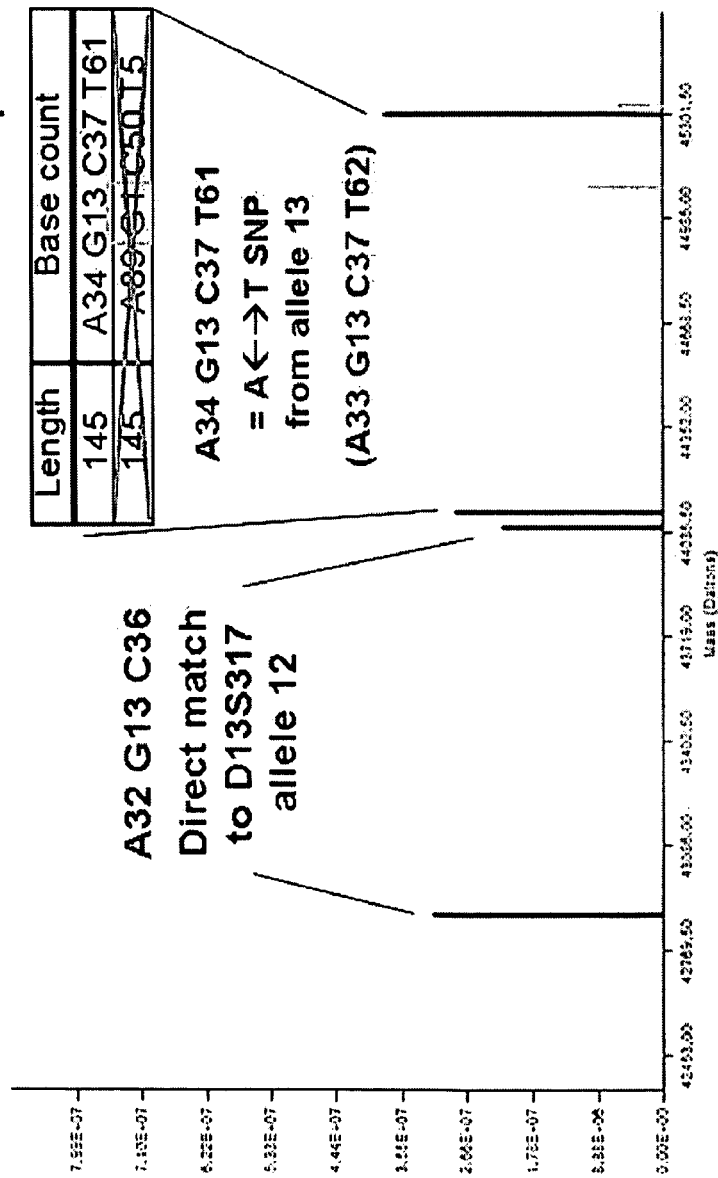
FIG. 5 illustrates an example of an allele variant that was found for STR locus D13S317 using a primer pair provided herein for one allele in a sample (Seracare blood sample N31773). The figure shows one allele being a direct match to reference allele 12. For the other allele, the base composition of the amplicon was calculated and added to the database indexed to the sample, primer pair, and the locus.

Following initial verification of primer efficacy, molecular mass of the amplification products were determined using both FTICR-MS and TOF-MS. An example of molecular mass determination for eight TPOX primer pairs is shown in FIG. 4. Base composition was calculated from molecular mass using the methods provided herein. Molecular masses and base compositions were compared to a database of reference (previously characterized) alleles indexed to the primer pairs constructed in silico as described above. Allele calls (identification of STR type) are made using each product strand individually and both strands are used to corroborate the call. Alleles for most loci were identified directly from the constructed database. However, in some cases, no direct match was found in the database constructed using previously characterized alleles. This lack of match occurred when the STR allele comprised a sequence polymorphism such as a single nucleotide polymorphism (SNP), such that an allele that had the same sequence length as a previously characterized or known allele, but comprised a distinct base composition compared with the characterized allele was resolved by the methods provided herein. One such example is shown in FIG. 5 for an allele from the D13S317 locus that comprised an A to T (A→T) SNP compared with characterized allele 13. In cases where there was no match to the initially populated database, length and base composition were derived using molecular masses from both strands of the amplicon and the information added to the database. In initial testing, as shown in FIG. 6, 58 STR primer pairs were analyzed using an internal positive control sample. Alleles were mapped for all but one primer pair. Similar results were obtained using FTCIR-MS and TOF-MS.

Example 9

Species Specificity, Controls, Sensitivity, Reproducibility and Precision Testing For all primer pairs developed to target human STRs, specificity to human DNA will be assessed by performing the assay upon DNA isolated from multiple sources of non-human DNA, including gram positive and gram-negative Bacteria, yeast, and DNA sources from two non-human mammals (cat and dog). Non-human DNA at an excess of up 10-fold over human DNA will be tested for its ability to interfere with human target priming or results after full data processing and analysis. Multiple well-characterized DNA samples derived from blood and saliva serve as positive controls for the methods provided herein, and nucleic acid-free water as negative control.

Sensitivity limits will be established by dilution-to-extinction (DTE) experiments using at least five different donor DNA samples as template. Blood-derived DNA samples will be used for these studies. Sensitivity will be defined as the lowest input of DNA that yields a full correct profile in two replicate experiments upon the same template, for all templates examined. Reliable sensitivity will be conservatively defined as an input template quantity 2-10 fold higher than the absolute sensitivity limit for the assay. Sensitivity will be expressed in terms of total DNA mass input (e.g., pg), as determined by the Quantifiler assay (Green, R. L.; Roinestad, I. C.; Boland, C.; Hennessy, L. K. *J Forensic Sci* 2005, 50, 809-825). Reproducibility will be assessed by the examination of three different templates 50 or more times and will be defined as the ability to obtain equivalent typing results at an input DNA concentration determined to be in the reliable range.

Assays have been tested for accuracy with panels of blinded samples supplied by the FBI and AFDIL laboratories. These labs provide samples that have already been typed by conventional STR-typing methods. Samples consisting of buccal swabs, blood punches, or DNA extracts are analyzed by the methods provided herein. A minimum of 50 to 250 diverse samples will be analyzed in this fashion.

Example 10a

Figure 8:
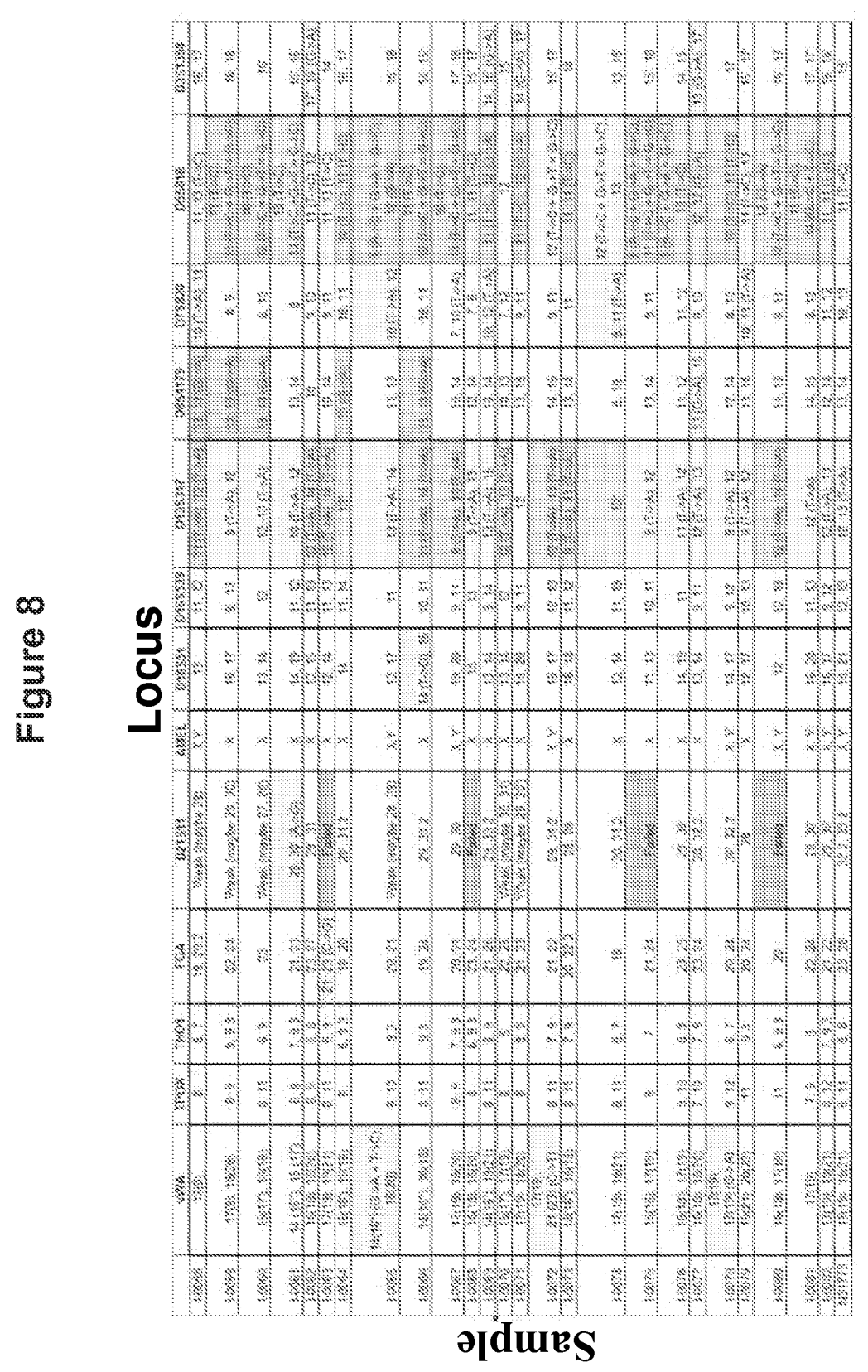
Figure 9:
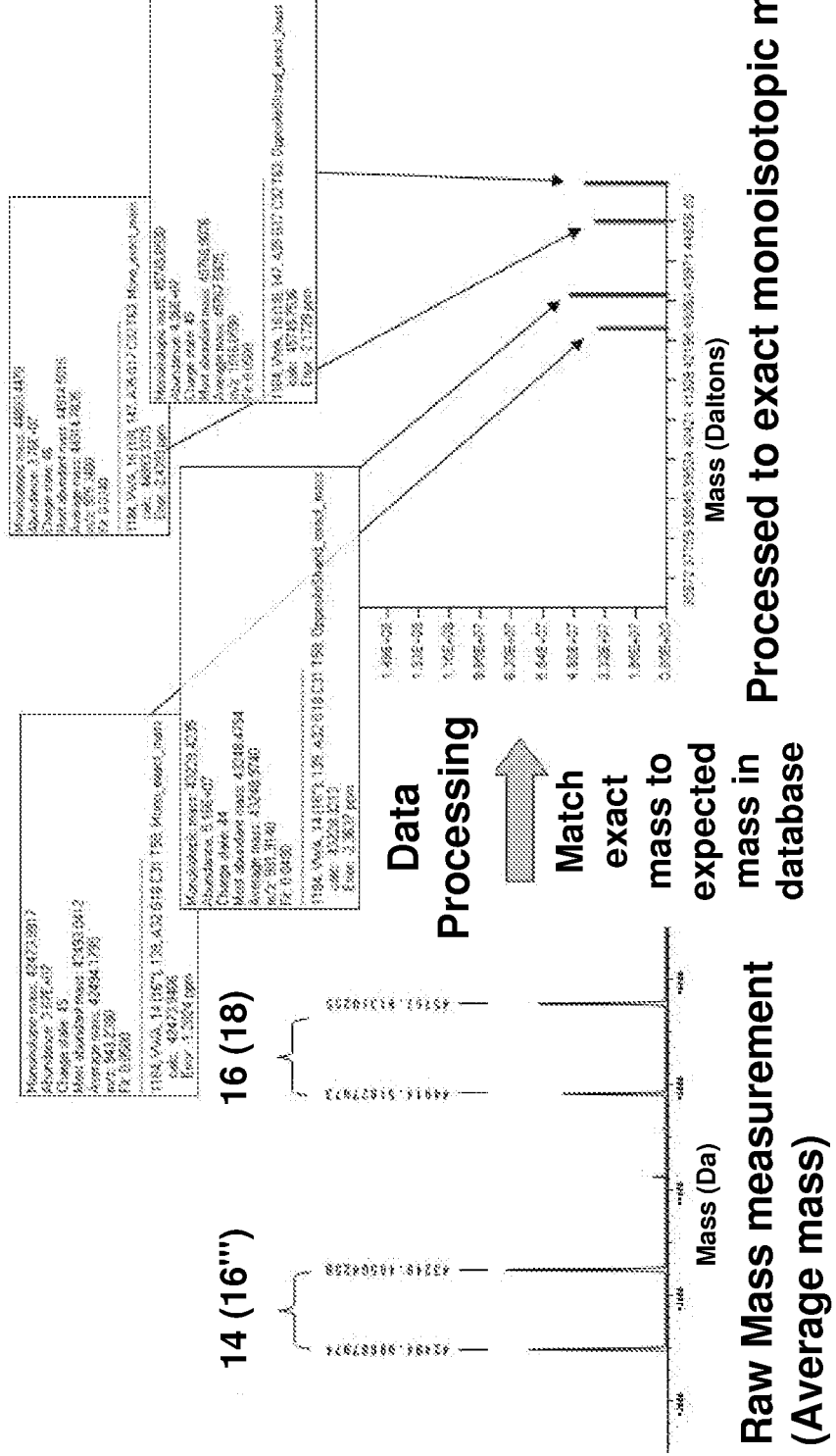
FIG. 9 is an illustrative example of STR-typing of one of the AFDIL blood samples (I-0066) from FIG. 8 with the primer pair 1184 which generates and amplicon from the vWA STR locus.

Preliminary Analysis of 25 Blood Spots from AFDIL 25 blinded blood samples received from AFDIL were used for STR typing using the methods and compositions described above using electrospray TOF-MS. Samples were provided as blood filter paper punches. 3 punches per sample were tested. Blood punches were processed with a Qiagen QIAmp™ DNA mini kit using the protocol for dried blood spots. 12 core CODIS STR loci and AMEL were analyzed using the methods described above. Two independent primer pairs for vWA, TPOX, THO1, FGA, D18S51, D16S539, D13S317, D8S1179, D7S820, D5S818, and D3S1358, for double-verification of allele calls. A redesigned primer pair for D21 S11 was used that shortens PCR products by 53 bases. Only one primer was used for AMEL. The results are summarized in FIG. 8. Detailed results for one sample, I-0066, are shown in FIG. 9. As shown in FIG. 8, several SNPs relative to reference sequences were identified for multiple STR loci in the 25 samples, demonstrating that some loci used in routine STR typing are inherently polymorphic in sequence. Several samples from individuals that would be identified as homozygous by conventional STR-typing PCR methods were revealed as heterozygous based on polymorphisms. Table 6 summarizes results of SNPs identified in this analysis of 25 AFDIL samples and one internal positive control (N31773).

TABLE 6

SNPs Identified in 25 AFDIL Samples

| Locus | SNP | Number Found |
|---|---|---|
| vWA | G->A | 2 |
| vWA | C->T | 1 |
| vWA | T->C | 1 |
| FGA | C->G | 1 |
| D21S11 | A->G | 1 |
| D18S51 | T->G | 1 |
| D13S317 | T->A | 32* |
| D8S1179 | G->A | 6 |
| D7S820 | T->A | 6 |
| D5S818 | G->T | 9 |
| D5S818 | T->C | 32** |
| D5S818 | A->C | 3 |
| D5S818 | G->A | 7 |
| D3S1358 | G->A | 4 |

*A majority of D13S317 alleles have an A->T SNP compared to the reference (GenBank G09017) sequence. Allele 16 did not have the A->T SNP
**A majority of D5S818 alleles have a T->C SNP compared to the reference (GenBank G09017) sequence. Allele 17 did not have the T->C SNP.

As illustrated in FIG. 8 and Table 6, for each of the 25 blinded samples, allele designations (STR-types) were determined for 12 of the 13 CODIS loci, which were concordant with the length allele data previously determined using standard STR-methods. Additionally, the methods provided more resolving power than previous methods in that SNPs were resolved in many samples that were not resolvable by standard methods. A type for D21S11 was determined for 15 of 25 samples. 106 apparent SNPs were identified relative to characterized alleles. In the case of four STR locus markers (D8S1179, D5S818, D13 S317, and vWA), SNPs were observed that revealed heterozygosity at the locus for the particular sample that was previously identified as homozygous by conventional STR-typing. In all cases, the SNPs were consistent between the two primer pairs used at each locus, with the exception of primer pair 1227, which masks a T→C SNP and a G→A SNP seen with 1228.

Example 10b

Preliminary Analysis of 95 Pre-Extracted Reference Samples from NIST 95 pre-extracted references samples from NIST were used for STR typing using the methods and compositions described above using electrospray TOF-MS. 13 core CODIS STR loci and AMEL were analyzed using the methods described above. Analysis of the extracted samples was performed in a multiplex reaction as described herein.

Example 11

Development of Multiplex STR-Typing Primers and Methods

Figure 10A:
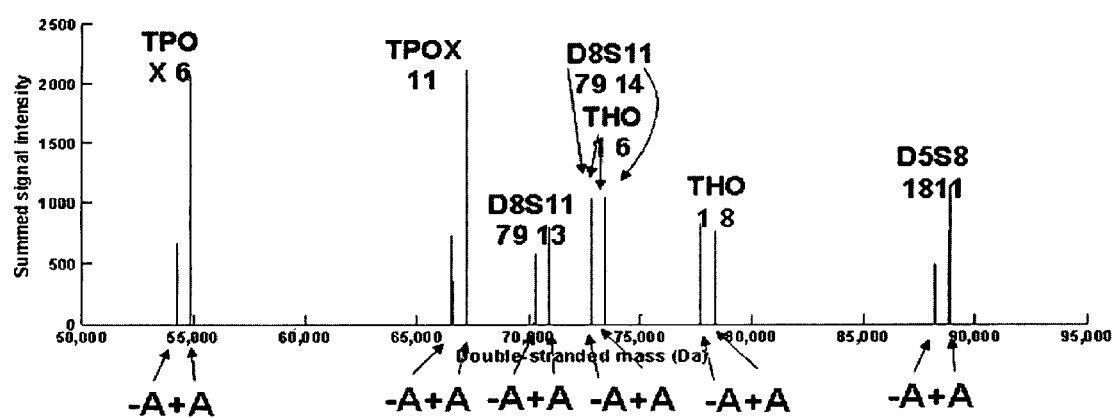
FIG. 10a illustrates the split-adenylation peaks generated with multiplexing using the Qiagen multiplex buffer and original primer pairs representing about a 50% adenylation of amplicons.

Multiplex reactions were developed capable of performing the methods provided herein using two or more primer pairs simultaneously in the same reaction mixture to resolve more than one STR-locus with the same reaction. Multiplexing was done using electrospray MS-TOF. Combinations of 2, 3, 4 and 6 primer pairs used in the initial studies were tested in initial stages of multiplex development. For improved multiplex reactions, the following conditions were used:

10-Locus Assay in 2 Six-Plex Multiplex Reactions (FBI and AFDIL Samples Described Herein)
   Qiagen Multiplex PCR kit comprising 3 mM Mg$^{++}$
   200 mM each primer
   1 ng template per reaction
   40 .micro.L reaction
   Cycle conditions:
     1-95 degree C. 15 minutes
     2-95 degree C. 30 seconds
     3-61 degree C. 2 minutes
     4-72 degree C. 30 seconds (2-4 for 35 cycles)
     5-72 degree C. 4 minutes
     6-60 degree C. 30 minutes
     7-4 degree C. hold 14-Locus Assay in 5 Tri-Plex and 3 Single-Plex Reactions (NIST Samples Described Herein)
   Qiagen Multiplex PCR kit comprising 3 mM Mg$^{++}$
   180 nanomoles to 300 nanomoles each primer
   1 ng template per reaction
   40 .micro.L reaction
     1-95 degree C. 15 minutes
     2-95 degree C. 30 seconds
     3-61 degree C. 2 minutes
     4-72 degree C. 25 seconds (2-4 for 40 cycles)
     5-72 degree C. 4 minutes
     6-60 degree C. 30 minutes
     7-4 degree C. hold For multiplexing, PCR reactions were carried out using the Qiagen Multiplex reaction buffer, which comprises 3 mM MgCl$_2$, and 61 degree C. was used as the preferred annealing temperature. This high magnesium concentration (which provides optimal multiplexing conditions) favors non-template adenylation to the 3' end of the amplification product, which can result in some PCR amplification products that are longer than the template, which is illustrated in FIG. 10a, which shows single peak view of deconvolved spectra showing split (+A and -A) peaks obtained using the internal standard sample and original primer pairs described above in initial testing. Since the high magnesium concentration was desired, to avoid shoulder peaks or split peaks, new primers were designed (shown in Table 5) for 8 STR loci (TH01, TPOX, D8S1179, D5S818, CSF1PO, D7S820, D13S317, and D16S539) that comprised either a G or C at the 5' end to favor full adenylation. Step 6-(60 degree C. 30 minutes) at the end of the cycle reaction also favors adenylation.

Figure 10B:
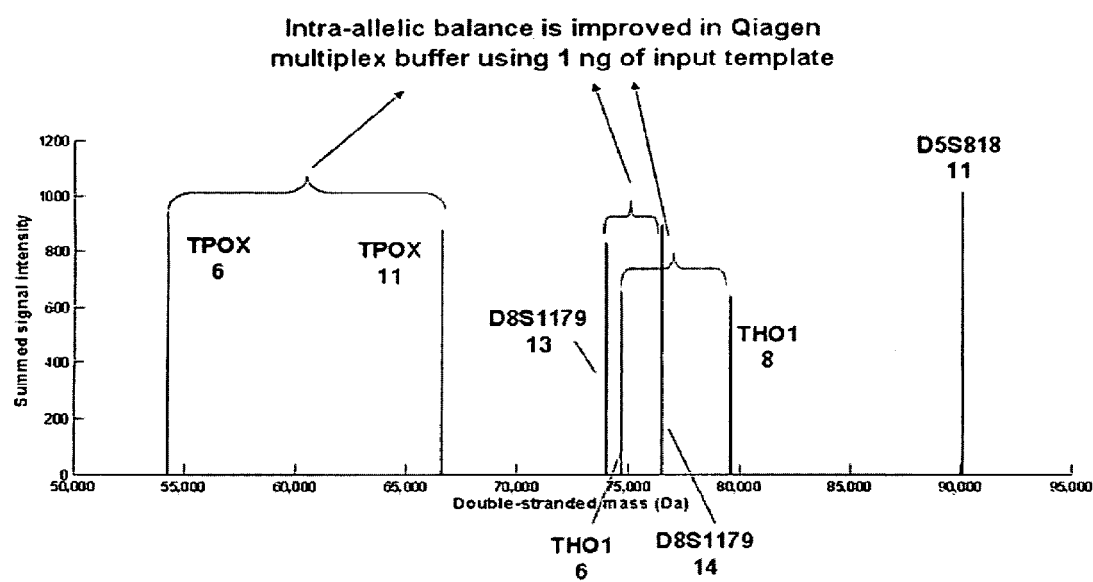
FIG. 10b illustrates loss of split-adenylation peaks with new primer pairs comprising a C or G residue on the 5' terminus.

FIG. 10b shows single peak spectra with no split peaks obtained using a four-plex (set of four primer pairs used simultaneously) comprised of four of the newly designed primer pairs (numbers 2856, 2822, 2818, 2816) that favor full adenylation. A second four-plex reaction using the other four newly designed primer pairs (2815, 2817, 2819, and 2820) was also tested and provided similarly favorable results. Thus two multiplex reactions were developed that could each resolve four different STR loci.

In order to create multiplex reactions with 6 primer pairs each, two additional primer pairs (2823-vWA and 2824-AMEL, also shown in Table 5) were added to each of the four-plex reactions. Table 7 shows the two six-plex reaction primer pair groups (1 and 2), which share these two common primer pairs.

TABLE 7

Multiplex STR Primer Pairs

| PRIMER PAIR NUMBER | PRIMER PAIR NAME | FORWARD PRIMER SEQUENCE | REVERSE PRIMER SEQUENCE | PRODUCT LENGTH RANGE | MULTIPLEX GROUP |
|---|---|---|---|---|---|
| 2856 | TH01_D00269_1107_1238 | GGAAATCA AAGGGTATC TGGGCTCTGG (SEQ ID NO. 10) | CGCTGGTCAC AGGGAACACA GAC (SEQ ID NO. 67) | 108-15 | 1 |
| 2822 | TPOX_M68651_1841_1947 | GGCACAGA ACAGGCACT TAGGGA (SEQ ID NO. 7) | GGTGTCCTTG TCAGCGTTTA TTTGCC (SEQ ID NO. 60) | 83-119 | 1 |
| 2818 | D8S1179_G08710_14_128 | GGGGTTTTG TATTTCATG TGTACATTC GTATC (SEQ ID NO. 31) | GGGTACCTAT CCTGTAGATT ATTTTCACTG TGG (SEQ ID NO. 88) | 95-143 | 1 |
| 2816 | D5S818_G08446_70_222 | GGGTGATTT TCCTCTTTG GTATCCTTA TGTAAT (SEQ ID NO. 40) | GCCAATCATA GCCACAGTTT ACAACATTTG TA (SEQ ID NO. 98) | 129-161 | 1 |

TABLE 7-continued

Multiplex STR Primer Pairs

| PRIMER PAIR NUMBER | PRIMER PAIR NAME | FORWARD PRIMER SEQUENCE | REVERSE PRIMER SEQUENCE | PRODUCT LENGTH RANGE | MULTIPLEX GROUP |
|---|---|---|---|---|---|
| 2815 | CSF1PO_U63963_11911_12038 | GGCATGAAGATATTAACAGTAACTGCCTTCATA (SEQ ID NO. 47) | GTGTCAGACCCTGTTCTAAGTACTTCCT (SEQ ID NO. 104) | 104-140 | 2 |
| 2817 | D7S820_G08616_93_229 | GGGAACACTTGTCATAGTTTAGAACGAACTA (SEQ ID NO. 35) | CCCGGAATGTTTACTATAGACTATTTAGTGAGAT (SEQ ID NO. 93) | 113-145 | 2 |
| 2819 | D13S317_G09017_88_222 | CTCTGACCCATCTAACGCCTATCTGTATTTAC (SEQ ID NO. 27) | GTAGGCAGCCCAAAAGACAGACAG (SEQ ID NO. 84) | 115-147 | 2 |
| 2820 | D16S539_G07925_232_351 | GCTCTTCCTCTTCCCTAGATCAATACAGACA (SEQ ID NO. 21) | GCTACCATCCATCTCTGTTTTGTCTTTCAATG (SEQ ID NO. 78) | 96-136 | 2 |
| 2823 | VWA_M25858_1651_1789 | GGGGAGAATAATCAGTATGTGACTTGGATTG (SEQ ID NO. 4) | GGGTGATAAATACATAGGATGGATGGATAGATGG (SEQ ID NO. 55) | 107-155 | 1 & 2 |
| 2824 | AMEL_M55418_286_394 | GCCCTGGGCTCTGTAAAGAATAGTG (SEQ ID NO. 51) | GCATCAGAGCTTAAACTGGGAAGCTG (SEQ ID NO. 108) | 109 or 115 | 1 & 2 |

Figure 11A:
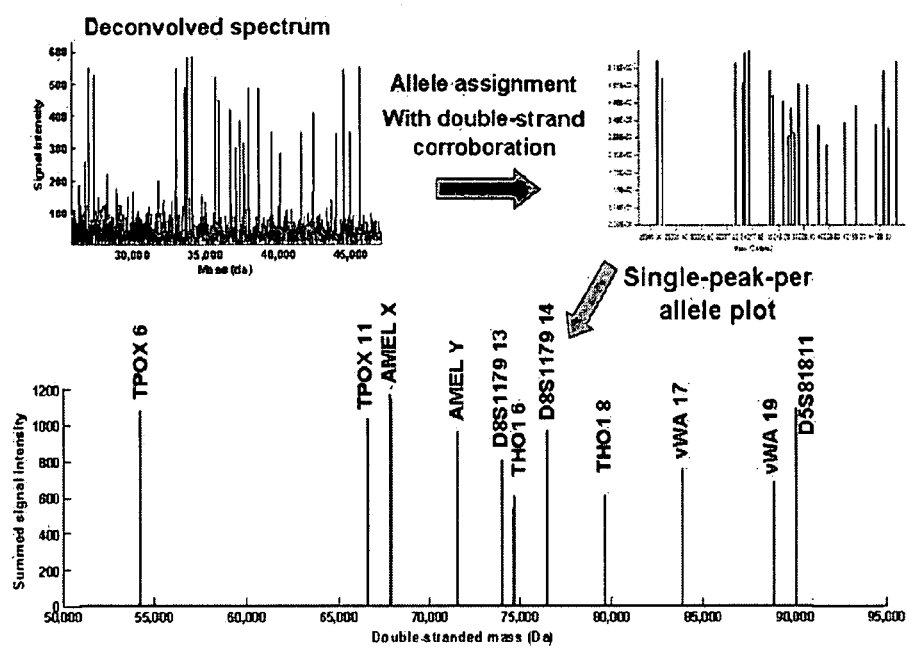
FIG. 11a and 11b show examples of 6-plex STR reaction 1 and 2 respectively with primer pairs listed in Table 7. As described in Example 11, all alleles were resolved using both multiplex reactions.
Figure 11B:
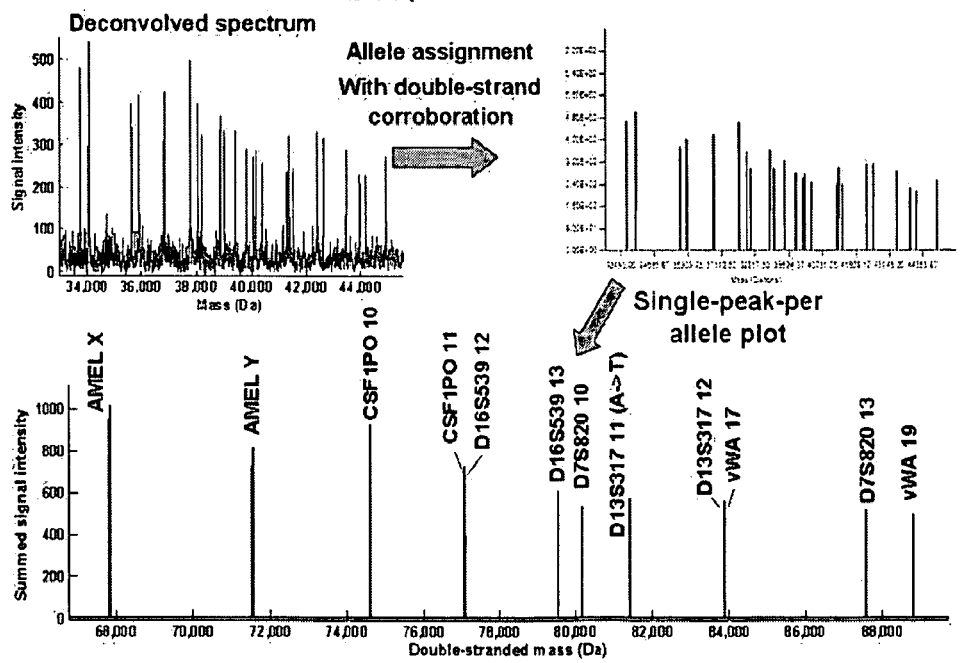
Figure 16:
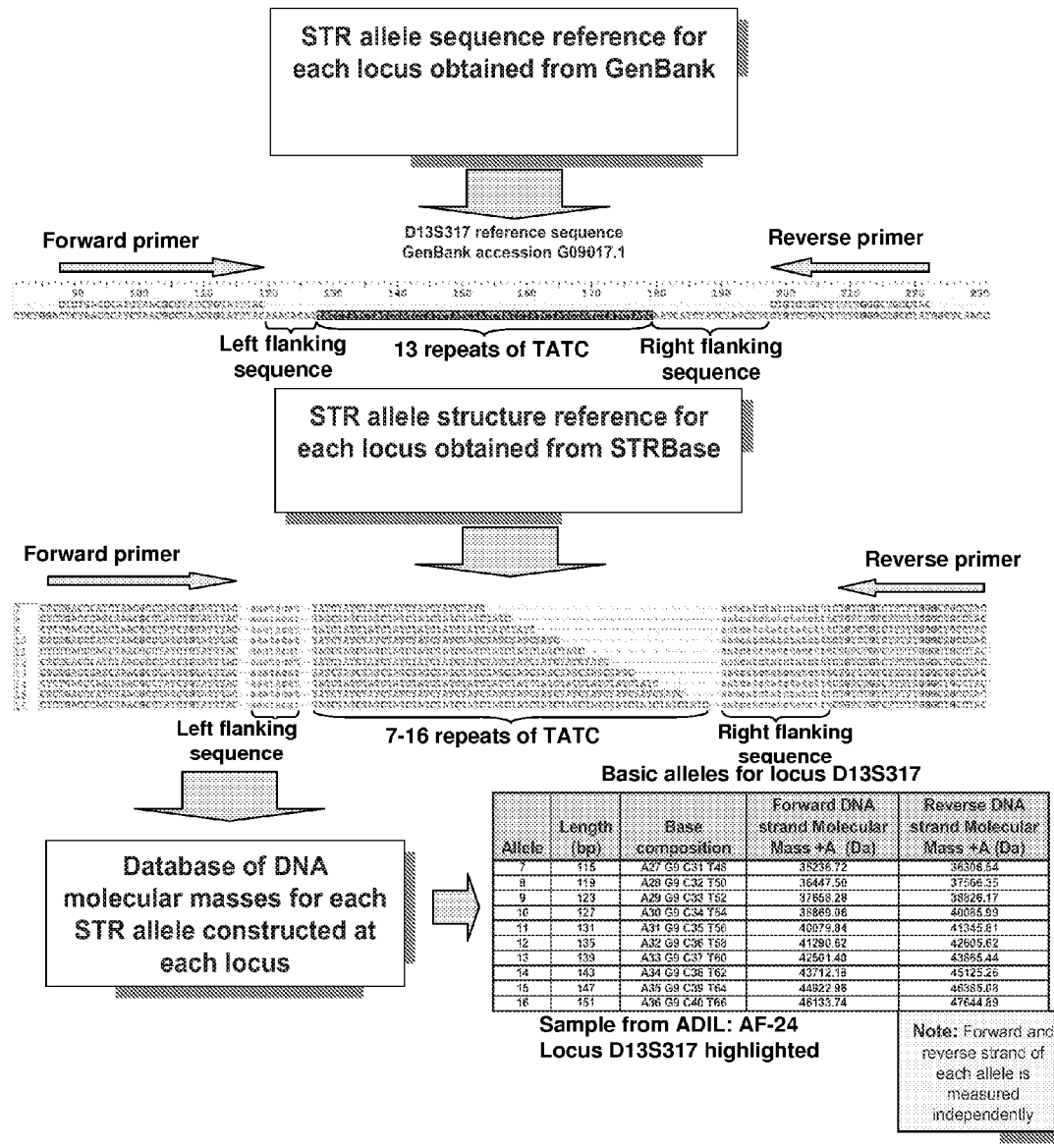
FIG. 16 illustrates the process of generating reference allele entries for an STR allele database is outlined above using D13S317 as an example.
Figure 17:
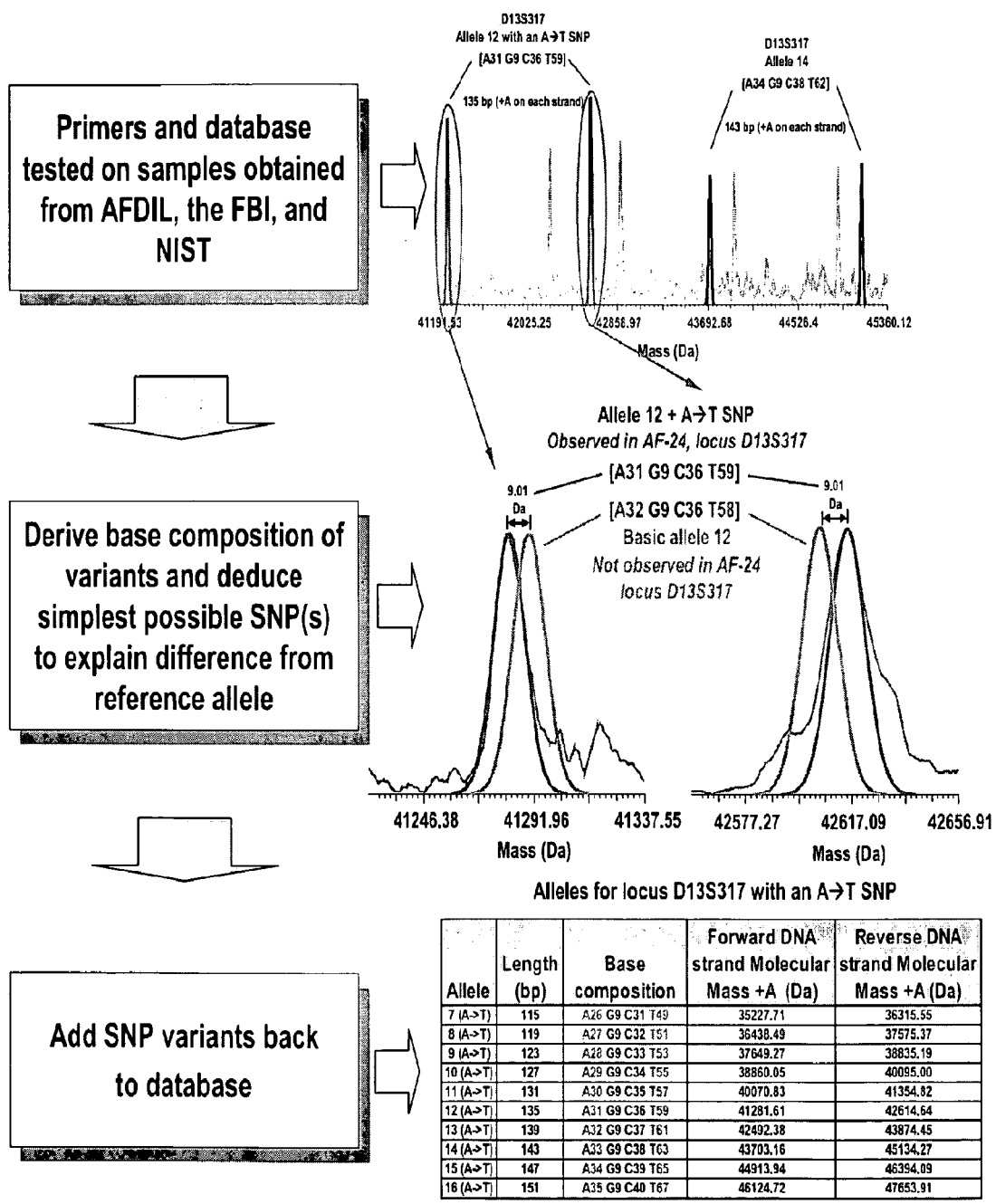
FIG. 17 illustrates the use of an allele database in the absence of an allelic ladder. Correct allele assignments can be made by the direct measurement of product masses and the subsequent calculation of product base compositions. A sequence polymorphism in the allele relative to the reference allele results in shifted masses of both the forward and reverse strands. Calculation of the product base composition reveals the polymorphism(s). Polymorphic alleles can then be added back to the database. The location of the polymorphism remains unknown unless the allele is sequenced. Also, if two cancelling polymorphisms are present (e.g. and A→G SNP and a G→A SNP within the same amplicon), the ESI-TOF-MS assay will not register a polymorphism.

FIG. 11a and FIG. 11b show deconvolved spectra, allele assignments and allele plots produced using the methods provided herein and an internal standard sample for each of the 6-plex reactions.

The 14-locus multiplex reaction was configured as follows:

TABLE 8

|  | Primer Pair | Locus | Primer Conc. nanomoles | FWD SEQ ID #:REV SEQ ID # |
|---|---|---|---|---|
| First Tri-Plex | 2819 | D13S317 | 200 | 27:84 |
|  | 2823 | vWA | 300 | 4:55 |
|  | 3397 | D3S1358 | 200 | 116:124 |
| Second Tri-Plex | 2820 | D16S539 | 300 | 21:78 |
|  | 2815 | CSF1PO | 180 | 24:81 |
|  | 2856 | THO1 | 220 | 10:67 |
| Third Tri-Plex | 2822 | TPOX | 200 | 7:60 |
|  | 2824 | AMEL | 200 | 51:108 |
|  | 2818 | D8S1179 | 250 | 31:88 |
| Fourth Tri-Plex | 2816 | D5S818 | 280 | 25:82 |
|  | 2817 | D7S820 | 250 | 26:83 |
|  | 2824 | AMEL | 200 | 51:108 |
| Fifth Tri-Plex | 2823 | vWA | 300 | 4:55 |
|  | 2816 | D5S818 | 250 | 25:82 |
|  | 2820 | D16S539 | 180 | 21:78 |
| First Single-Plex | 3390 | D21S11 | 200 | 109:117 |
| Second Single-Plex | 3393 | FGA | 200 | 112:120 |
| Third Single-Plex | 3394 | D18S51 | 200 | 113:121 |

Example 12

Initial Testing of Multiplex STR-Typing Primers with Blinded AFDIL Samples

The 25 blinded AFDIL blood punch samples described hereinabove were tested using the two groups of 6-plex primers in multiplex reactions using the conditions described above for multiplexing with 1 ng template DNA per reaction. Results are summarized in FIG. 12.

As shown, for the loci tested with the multiplex primers listed in Table 7, all alleles previously identified during single-plex STR-typing were confirmed, including all SNPs observed with single-plex typing reactions. No SNPs were observed that were not identified in the single-plex reactions. Thus results with six-plex primer pair assay were consistent with single-plex assay.

Example 13

STR Typing of 25 New AFDIL Blinded Samples Using Multiplex Primer Sets 25 new blinded blood punch samples from AFDIL were purified as described above using the Qiagen blood spot protocol. DNA was quantified using qPCR and 1 ng used per reaction for STR-typing using 6-plex multiplex primer mixes and methods described above. The reactions were carried out in multi-well plates, using blood sample SC35495 as a positive control and water as a negative control. Results are summarized in FIG. 13a. An example is illustrated for one sample (AF-1) in FIG. 14. As shown in FIG. 13a, AFDIL confirmed that all alleles (lengths) identified by the multiplexing methods. Additionally, SNPs (relative to the characterized allele in the database) were identified in at least one locus in 23 of the 25 samples that had not been detected using conventional STR-typing.

Example 14

STR Typing of 22 New FBI Blinded Buccal Swab Samples Using Multiplex Primer Sets 22 blinded buccal swab samples from the FBI were tested using the two 6-plex multiplex primer sets as described above for the AFDIL samples. Samples were run in duplicate and negative controls were water and FBI-100, which contained no DNA. Results are summarized in FIG. 13b. Full STR profiles (for the loci tested) were identified in all samples. In 21 of the 22 samples, at least one SNP was observed relative to the reference database. Results will be sent to the FBI for verification of allele calls.

Example 15

Summary of SNP Variants Observed in 47 Blinded Samples Using STR-Typing With Multiplex Primer Sets FIG. 13c shows the number of alleles with SNPs, % of allele calls containing a SNP and number of same-length heterozygous loci resolved using the methods described herein for these 47 blinded samples (from AFDIL/FBI). The results for these samples tested with 6-plex reactions using the methods provided herein demonstrate that some of the loci used in routine STR typing are inherently polymorphic in sequence (as demonstrated by product base compositions) as well as length, and thus STR-typing using the methods provided herein provides an additional level of resolution via a rapid and automated method that will be useful in forensics and other DNA identification applications.

Example 16

Results from 95 Samples Obtained from NIST

In the 95 samples from NIST, polymorphisms were found in 10 of the 13 core CODIS loci. A total of 364 polymorphic alleles were detected in 1330 genotype assignments (95 samples typed at 14 loci). Thirteen distinct variant alleles were identified in D21S11, 13 in vWA, 11 in D3S1358, eight in D5S818, seven in D8S1179, six in D13S317, four in D7S820, three in D18S51, two in FGA and one in D16S539. Table 9 shows the frequency of each allele observed for each of the three population groups, with polymorphic alleles annotated with the SNP(s) present relative to the reference allele. Sixty percent of alleles observed in the 95 samples for D3S1358 were polymorphic relative to the reference allele. For this locus, each allele length appears to have three polymorphic variants in the population: one base allele (the choice of reference is somewhat arbitrary), one with a G→A SNP, and one with two G→A SNPs. Two previous studies reporting sequencing of this locus report a complex repeat structure with TCTA and TCTG repeats. In one of these studies, multiple same-length allele pairs were reported with different sequence structure for D3S1358, vWA and FGA, consistent with our results. In addition, our results indicate the presence of more than two same-length variants for multiple allele lengths in D3S1358, vWA and D21S11 (we observed three variants each for several allele lengths at each of these loci). Table 9 shows the overall frequency of observations for polymorphic alleles in the 47 FBI and AFDIL samples plus the 95 NIST samples combined.

TABLE 9

Observed frequency of each allele by population in 31 Caucasian, 32 African American and 32 Hispanic samples from NIST.

| | | Count | | | Percentage | | |
|---|---|---|---|---|---|---|---|
| Locus | Allele | Caucasian | African American | Hispanic | Caucasian | African American | Hispanic |
| AMEL | X | 31 | 32 | 32 | 50.00 | 50.00 | 50.00 |
| | Y | 31 | 32 | 32 | 50.00 | 50.00 | 50.00 |
| CSF1PO | 7 | 0 | 5 | 0 | 0.00 | 7.81 | 0.00 |
| | 8 | 0 | 4 | 0 | 0.00 | 6.25 | 0.00 |
| | 9 | 1 | 2 | 1 | 1.61 | 3.13 | 1.56 |
| | 10 | 11 | 15 | 19 | 17.74 | 23.44 | 29.69 |
| | 11 | 16 | 17 | 15 | 25.81 | 26.56 | 23.44 |
| | 12 | 29 | 17 | 24 | 46.77 | 26.56 | 37.50 |
| | 13 | 5 | 4 | 4 | 8.06 | 6.25 | 6.25 |
| | 14 | 0 | 0 | 1 | 0.00 | 0.00 | 1.56 |
| D13S317 | 8 | 8 | 2 | 6 | 12.90 | 3.13 | 9.38 |
| | 9 | 3 | 1 | 13 | 4.84 | 1.56 | 20.31 |
| | 9 (A->T) | 0 | 0 | 1 | 0.00 | 0.00 | 1.56 |
| | 10 | 0 | 0 | 2 | 0.00 | 0.00 | 3.13 |
| | 10 (A->T) | 1 | 1 | 5 | 1.61 | 1.56 | 7.81 |
| | 11 | 13 | 8 | 11 | 20.97 | 12.50 | 17.19 |
| | 11 (A->T) | 10 | 10 | 4 | 16.13 | 15.63 | 6.25 |
| | 12 | 6 | 26 | 9 | 9.68 | 40.63 | 14.06 |
| | 12 (A->T) | 7 | 7 | 2 | 11.29 | 10.94 | 3.13 |
| | 13 | 11 | 9 | 5 | 17.74 | 14.06 | 7.81 |
| | 13 (A->T) | 0 | 0 | 2 | 0.00 | 0.00 | 3.13 |
| | 14 | 3 | 0 | 3 | 4.84 | 0.00 | 4.69 |
| | 15 (A->T) | 0 | 0 | 1 | 0.00 | 0.00 | 1.56 |

TABLE 9-continued

Observed frequency of each allele by population in 31 Caucasian, 32 African American and 32 Hispanic samples from NIST.

| Locus | Allele | Count Caucasian | Count African American | Count Hispanic | Percentage Caucasian | Percentage African American | Percentage Hispanic |
|---|---|---|---|---|---|---|---|
| D16S539 | 8 | 1 | 2 | 0 | 1.61 | 3.13 | 0.00 |
| | 9 | 10 | 11 | 7 | 16.13 | 17.19 | 10.94 |
| | 9 (A->G) | 1 | 0 | 0 | 1.61 | 0.00 | 0.00 |
| | 10 | 2 | 6 | 7 | 3.23 | 9.38 | 10.94 |
| | 11 | 18 | 24 | 16 | 29.03 | 37.50 | 25.00 |
| | 12 | 21 | 10 | 18 | 33.87 | 15.63 | 28.13 |
| | 13 | 9 | 11 | 15 | 14.52 | 17.19 | 23.44 |
| | 14 | 0 | 0 | 1 | 0.00 | 0.00 | 1.56 |
| D18S51 | 10 | 1 | 0 | 0 | 1.61 | 0.00 | 0.00 |
| | 11 | 0 | 0 | 1 | 0.00 | 0.00 | 1.56 |
| | 12 | 8 | 7 | 6 | 12.90 | 10.94 | 9.38 |
| | 13 | 9 | 4 | 9 | 14.52 | 6.25 | 14.06 |
| | 13.2 (T->C) | 0 | 2 | 0 | 0.00 | 3.13 | 0.00 |
| | 14 | 7 | 3 | 9 | 11.29 | 4.69 | 14.06 |
| | 15 | 5 | 9 | 13 | 8.06 | 14.06 | 20.31 |
| | 15 (T->G) | 1 | 0 | 0 | 1.61 | 0.00 | 0.00 |
| | 16 | 12 | 12 | 7 | 19.35 | 18.75 | 10.94 |
| | 17 | 9 | 14 | 8 | 14.52 | 21.88 | 12.50 |
| | 18 | 5 | 5 | 4 | 8.06 | 7.81 | 6.25 |
| | 19 | 2 | 2 | 3 | 3.23 | 3.13 | 4.69 |
| | 20 | 2 | 0 | 2 | 3.23 | 0.00 | 3.13 |
| | 20 (T->C) | 0 | 4 | 0 | 0.00 | 6.25 | 0.00 |
| | 21 | 0 | 0 | 1 | 0.00 | 0.00 | 1.56 |
| | 22 | 1 | 1 | 1 | 1.61 | 1.56 | 1.56 |
| | 23 | 0 | 1 | 0 | 0.00 | 1.56 | 0.00 |
| D21S11 | 25.2 | 1 | 0 | 0 | 1.61 | 0.00 | 0.00 |
| | 27 | 0 | 2 | 1 | 0.00 | 3.13 | 1.56 |
| | 27 (A->G) | 2 | 2 | 0 | 3.23 | 3.13 | 0.00 |
| | 28 | 14 | 12 | 5 | 22.58 | 18.75 | 7.81 |
| | 29 | 7 | 10 | 16 | 11.29 | 15.63 | 25.00 |
| | 29 (G->A) | 3 | 0 | 3 | 4.84 | 0.00 | 4.69 |
| | 29 (A->G) | 0 | 3 | 0 | 0.00 | 4.69 | 0.00 |
| | 29.2 (A->G) | 1 | 0 | 0 | 1.61 | 0.00 | 0.00 |
| | 30 | 11 | 3 | 7 | 17.74 | 4.69 | 10.94 |
| | 30 (G->A) | 5 | 12 | 9 | 8.06 | 18.75 | 14.06 |
| | 30.2 | 2 | 1 | 4 | 3.23 | 1.56 | 6.25 |
| | 30.2 (G->A) | 1 | 0 | 0 | 1.61 | 0.00 | 0.00 |
| | 31 | 2 | 4 | 2 | 3.23 | 6.25 | 3.13 |
| | 31 (G->A) | 3 | 1 | 2 | 4.84 | 1.56 | 3.13 |
| | 31.2 | 3 | 3 | 6 | 4.84 | 4.69 | 9.38 |
| | 31.2 (G->A) | 0 | 0 | 1 | 0.00 | 0.00 | 1.56 |
| | 32 (A->G) | 0 | 1 | 0 | 0.00 | 1.56 | 0.00 |
| | 32.2 | 6 | 6 | 5 | 9.68 | 9.38 | 7.81 |
| | 32.2 (G->A) | 0 | 0 | 2 | 0.00 | 0.00 | 3.13 |
| | 33.2 | 1 | 1 | 0 | 1.61 | 1.56 | 0.00 |
| | 34 | 0 | 0 | 1 | 0.00 | 0.00 | 1.56 |
| | 34.1 (T->A) | 0 | 1 | 0 | 0.00 | 1.56 | 0.00 |
| | 36 (2A->2G) | 0 | 1 | 0 | 0.00 | 1.56 | 0.00 |
| | 37 (3A->3G) | 0 | 1 | 0 | 0.00 | 1.56 | 0.00 |
| D3S1358 | 13 | 0 | 0 | 1 | 0.00 | 0.00 | 1.56 |
| | 13 (G->A) | 0 | 1 | 0 | 0.00 | 1.56 | 0.00 |
| | 14 | 4 | 2 | 5 | 6.45 | 3.13 | 7.81 |
| | 14 (G->A) | 0 | 0 | 2 | 0.00 | 0.00 | 3.13 |
| | 15 | 2 | 1 | 1 | 3.23 | 1.56 | 1.56 |
| | 15 (G->A) | 13 | 8 | 17 | 20.97 | 12.50 | 26.56 |
| | 15 (2G->2A) | 2 | 12 | 4 | 3.23 | 18.75 | 6.25 |
| | 15.2 | 0 | 1 | 0 | 0.00 | 1.56 | 0.00 |
| | 16 | 5 | 3 | 5 | 8.06 | 4.69 | 7.81 |
| | 16 (G->A) | 8 | 6 | 5 | 12.90 | 9.38 | 7.81 |
| | 16 (2G->2A) | 0 | 10 | 2 | 0.00 | 15.63 | 3.13 |
| | 17 | 7 | 4 | 7 | 11.29 | 6.25 | 10.94 |
| | 17 (A->G) | 0 | 1 | 1 | 0.00 | 1.56 | 1.56 |
| | 17 (2G->2A) | 1 | 2 | 0 | 1.61 | 3.13 | 0.00 |
| | 17 (G->A) | 8 | 6 | 5 | 12.90 | 9.38 | 7.81 |
| | 18 | 12 | 4 | 8 | 19.35 | 6.25 | 12.50 |
| | 18 (G->A) | 0 | 2 | 1 | 0.00 | 3.13 | 1.56 |
| | 18 (2G->2A) | 0 | 1 | 0 | 0.00 | 1.56 | 0.00 |

TABLE 9-continued

Observed frequency of each allele by population in 31 Caucasian, 32 African American and 32 Hispanic samples from NIST.

| | | Count | | | Percentage | | |
|---|---|---|---|---|---|---|---|
| Locus | Allele | Caucasian | African American | Hispanic | Caucasian | African American | Hispanic |
| D5S818 | 7 | 0 | 0 | 5 | 0.00 | 0.00 | 7.81 |
| | 8 | 1 | 0 | 0 | 1.61 | 0.00 | 0.00 |
| | 8 (G->T) | 0 | 3 | 0 | 0.00 | 4.69 | 0.00 |
| | 9 (G->T) | 1 | 3 | 2 | 1.61 | 4.69 | 3.13 |
| | 10 | 5 | 4 | 3 | 8.06 | 6.25 | 4.69 |
| | 10 (G->T) | 0 | 0 | 1 | 0.00 | 0.00 | 1.56 |
| | 11 | 25 | 13 | 25 | 40.32 | 20.31 | 39.06 |
| | 11 (G->T) | 4 | 2 | 0 | 6.45 | 3.13 | 0.00 |
| | 12 | 15 | 22 | 15 | 24.19 | 34.38 | 23.44 |
| | 12 (G->T) | 4 | 7 | 3 | 6.45 | 10.94 | 4.69 |
| | 13 | 5 | 5 | 5 | 8.06 | 7.81 | 7.81 |
| | 13 (G->T) | 1 | 3 | 0 | 1.61 | 4.69 | 0.00 |
| | 13 (G->C) | 0 | 0 | 1 | 0.00 | 0.00 | 1.56 |
| | 14 | 1 | 1 | 2 | 1.61 | 1.56 | 3.13 |
| | 14 (G->T) | 0 | 1 | 1 | 0.00 | 1.56 | 1.56 |
| | 15 | 0 | 0 | 1 | 0.00 | 0.00 | 1.56 |
| D7S820 | 7 | 2 | 0 | 0 | 3.23 | 0.00 | 0.00 |
| | 8 | 10 | 13 | 8 | 16.13 | 20.31 | 12.50 |
| | 9 | 9 | 10 | 7 | 14.52 | 15.63 | 10.94 |
| | 10 | 13 | 25 | 14 | 20.97 | 39.06 | 21.88 |
| | 10 (T->A) | 2 | 0 | 3 | 3.23 | 0.00 | 4.69 |
| | 11 | 10 | 12 | 19 | 16.13 | 18.75 | 29.69 |
| | 11 (T->A) | 3 | 0 | 0 | 4.84 | 0.00 | 0.00 |
| | 12 | 4 | 3 | 7 | 6.45 | 4.69 | 10.94 |
| | 12 (T->A) | 6 | 0 | 3 | 9.68 | 0.00 | 4.69 |
| | 13 | 3 | 1 | 2 | 4.84 | 1.56 | 3.13 |
| | 13 (T->A) | 0 | 0 | 1 | 0.00 | 0.00 | 1.56 |
| D8S1179 | 8 | 1 | 0 | 0 | 1.61 | 0.00 | 0.00 |
| | 10 | 5 | 1 | 6 | 8.06 | 1.56 | 9.38 |
| | 11 | 7 | 1 | 5 | 11.29 | 1.56 | 7.81 |
| | 12 | 10 | 1 | 8 | 16.13 | 1.56 | 12.50 |
| | 12 (A->G) | 0 | 5 | 2 | 0.00 | 7.81 | 3.13 |
| | 13 | 19 | 17 | 14 | 30.65 | 26.56 | 21.88 |
| | 13 (G->A) | 3 | 3 | 3 | 4.84 | 4.69 | 4.69 |
| | 13 (C->G) | 0 | 0 | 1 | 0.00 | 0.00 | 1.56 |
| | 14 | 6 | 23 | 12 | 9.68 | 35.94 | 18.75 |
| | 14 (G->A) | 6 | 1 | 2 | 9.68 | 1.56 | 3.13 |
| | 15 | 3 | 7 | 7 | 4.84 | 10.94 | 10.94 |
| | 15 (A->G) | 0 | 1 | 0 | 0.00 | 1.56 | 0.00 |
| | 16 | 2 | 3 | 2 | 3.23 | 4.69 | 3.13 |
| | 16 (A->G) | 0 | 1 | 0 | 0.00 | 1.56 | 0.00 |
| | 17 (G->A) | 0 | 0 | 1 | 0.00 | 0.00 | 1.56 |
| | 18 | 0 | 0 | 1 | 0.00 | 0.00 | 1.56 |
| FGA | 18 | 2 | 0 | 2 | 3.23 | 0.00 | 3.13 |
| | 19 | 3 | 5 | 5 | 4.84 | 7.81 | 7.81 |
| | 19.2 | 0 | 1 | 0 | 0.00 | 1.56 | 0.00 |
| | 20 | 7 | 3 | 4 | 11.29 | 4.69 | 6.25 |
| | 21 | 8 | 2 | 11 | 12.90 | 3.13 | 17.19 |
| | 22 | 13 | 12 | 9 | 20.97 | 18.75 | 14.06 |
| | 22.2 | 1 | 0 | 0 | 1.61 | 0.00 | 0.00 |
| | 23 | 11 | 11 | 14 | 17.74 | 17.19 | 21.88 |
| | 23.2 | 1 | 1 | 0 | 1.61 | 1.56 | 0.00 |
| | 24 | 9 | 11 | 9 | 14.52 | 17.19 | 14.06 |
| | 25 | 5 | 9 | 4 | 8.06 | 14.06 | 6.25 |
| | 26 | 2 | 5 | 5 | 3.23 | 7.81 | 7.81 |
| | 26 (G->A) | 0 | 1 | 0 | 0.00 | 1.56 | 0.00 |
| | 27 | 0 | 1 | 1 | 0.00 | 1.56 | 1.56 |
| | 28 (T->C) | 0 | 1 | 0 | 0.00 | 1.56 | 0.00 |
| | 31.2 | 0 | 1 | 0 | 0.00 | 1.56 | 0.00 |
| THO1 | 6 | 15 | 6 | 10 | 24.19 | 9.38 | 15.63 |
| | 7 | 9 | 33 | 25 | 14.52 | 51.56 | 39.06 |
| | 8 | 3 | 14 | 8 | 4.84 | 21.88 | 12.50 |
| | 9 | 10 | 7 | 6 | 16.13 | 10.94 | 9.38 |
| | 9.3 | 25 | 4 | 15 | 40.32 | 6.25 | 23.44 |
| TPOX | 6 | 1 | 8 | 0 | 1.61 | 12.50 | 0.00 |
| | 7 | 0 | 1 | 0 | 0.00 | 1.56 | 0.00 |
| | 8 | 33 | 21 | 29 | 53.23 | 32.81 | 45.31 |
| | 9 | 10 | 12 | 5 | 16.13 | 18.75 | 7.81 |
| | 10 | 2 | 7 | 2 | 3.23 | 10.94 | 3.13 |
| | 11 | 15 | 14 | 18 | 24.19 | 21.88 | 28.13 |
| | 12 | 1 | 1 | 10 | 1.61 | 1.56 | 15.63 |

TABLE 9-continued

Observed frequency of each allele by population in 31 Caucasian, 32 African American and 32 Hispanic samples from NIST.

| | | Count | | | Percentage | | |
|---|---|---|---|---|---|---|---|
| Locus | Allele | Caucasian | African American | Hispanic | Caucasian | African American | Hispanic |
| vWA | 13 (G->A + C->T) | 1 | 0 | 0 | 1.61 | 0.00 | 0.00 |
| | 13 (C->T) | 0 | 1 | 0 | 0.00 | 1.56 | 0.00 |
| | 14 (T->C) | 0 | 2 | 0 | 0.00 | 3.13 | 0.00 |
| | 14 (G->A + T->C) | 3 | 0 | 0 | 4.84 | 0.00 | 0.00 |
| | 14 (A->G + 2T->2C) | 6 | 2 | 3 | 9.68 | 3.13 | 4.69 |
| | 15 | 0 | 5 | 7 | 0.00 | 7.81 | 10.94 |
| | 15 (G->A) | 7 | 1 | 7 | 11.29 | 1.56 | 10.94 |
| | 16 | 9 | 11 | 13 | 14.52 | 17.19 | 20.31 |
| | 16 (G->A) | 2 | 7 | 3 | 3.23 | 10.94 | 4.69 |
| | 17 | 12 | 13 | 14 | 19.35 | 20.31 | 21.88 |
| | 17 (G->A) | 2 | 1 | 3 | 3.23 | 1.56 | 4.69 |
| | 18 | 11 | 16 | 8 | 17.74 | 25.00 | 12.50 |
| | 18 (G->A) | 1 | 0 | 0 | 1.61 | 0.00 | 0.00 |
| | 18 (2A->2G) | 0 | 1 | 0 | 0.00 | 1.56 | 0.00 |
| | 19 | 7 | 2 | 4 | 11.29 | 3.13 | 6.25 |
| | 19 (2A->2G) | 0 | 1 | 0 | 0.00 | 1.56 | 0.00 |
| | 20 | 0 | 0 | 2 | 0.00 | 0.00 | 3.13 |
| | 20 (T->A) | 1 | 0 | 0 | 1.61 | 0.00 | 0.00 |
| | 20 (A->G) | 0 | 1 | 0 | 0.00 | 1.56 | 0.00 |

It is, therefore, another embodiment is a method of differentiating between two or more forensic DNA samples having the same length-based allele for a STR locus by analyzing the allele via mass spectrometry and/or base composition analysis. An additional embodiment, therefore, is a method of differentiating between two or more forensic DNA samples having the same length-based allele for a STR locus by detecting one or more single nucleotide polymorphisms that are not resolved by conventional length/size-based STR analysis within said allele, including, but not limited to those polymorphisms described in Table 9. Each of the SNPs described herein are capable of providing information regarding the population to which the forensic sample belongs, for example, Caucasian, African American, or Hispanic.

In an additional embodiment the method of differentiating between two or more forensic DNA samples can be performed after conventional length/size-based STR analysis do not resolve said two or more forensic samples. An additional embodiment is a method of differentiating between two or more forensic DNA samples by amplifying one or more STR loci to produce one or more STR loci amplification products; obtaining mass measurements of the STR loci amplification products via mass spectrometry; calculating STR loci base compositions from the mass measurements; comparing the STR loci base compositions of the two or more samples to each other and/or to a database of STR loci base compositions of known DNA samples to identify the source of the forensic DNA sample. The method may further comprise assigning an allele call and/or SNP designation.

Another embodiment is a method of differentiating two or more forensic DNA samples having for the D13S317 locus an allele call of 9 based upon a SNP of A→T, an allele call of 10 based upon a SNP of A→T, an allele call of 11 based upon a SNP of A→T, an allele call of 12 based upon a SNP of A→T, an allele call of 12 based upon a SNP of A→T, an allele call of 13 based upon a SNP of A→T, or an allele call of 15 based upon a SNP of A→T.

Another embodiment is a method of differentiating two or more forensic DNA samples having for the D16S539 locus an allele call of 9 based upon a SNP of T→C.

Another embodiment is a method of differentiating two or more forensic DNA samples having for the D18S51 locus an allele call of 13.2 based upon a SNP of T→C, an allele call of 15 based upon a SNP of T→C, or an allele call of 20 based upon a SNP of T→C.

Another embodiment is a method of differentiating two or more forensic DNA samples having for the D21S11 locus an allele call of 27 based upon a SNP of A→G, an allele call of 29 based upon a SNP of G→A, an allele call of 29 based upon a SNP of A→G, an allele call of 29.2 based upon a SNP of A→G, an allele call of 30 based upon a SNP of G→A, an allele call of 30.2 based upon a SNP of G→A, an allele call of 31 based upon a SNP of G→A, an allele call of 31.2 based upon a SNP of G→A, an allele call of 32 based upon a SNP of A→G, an allele call of 32.2 based upon a SNP of G→A, an allele call of 34.1 based upon a SNP of T→A, an allele call of 36 based upon a SNP of 2A→2G, or an allele call of 37 based upon a SNP of 3A→3G.

Another embodiment is a method of differentiating two or more forensic DNA samples having for the D3S1358 locus an allele call of 13 based upon a SNP of G→A, an allele call of 14 based upon a SNP of G→A, an allele call of 15 based upon a SNP of G→A, an allele call of 15 based upon a SNP of 2G→2A, an allele call of 16 based upon a SNP of G→A, an allele call of 16 based upon a SNP of 2G→2A, an allele call of 17 based upon a SNP of G→A, an allele call of 17 based upon a SNP of 2G→2A, an allele call of 17 based upon a SNP of A→G, an allele call of 18 based upon a SNP of G→A, or an allele call of 18 based upon a SNP of 2G→2A.

Another embodiment is a method of differentiating two or more forensic DNA samples having for the D5S818 locus an allele call of 8 based upon a SNP of G→T, an allele call of 9 based upon a SNP of G→T, an allele call of 10 based upon a SNP of G→T, an allele call of 11 based upon a SNP of G→T, an allele call of 12 based upon a SNP of G→T, an allele call of 13 based upon a SNP of G→T, an allele call of 13 based upon a SNP of G→C, or an allele call of 14 based upon a SNP of G→T.

Another embodiment is a method of differentiating two or more forensic DNA samples having for the D7S820 locus an allele call of 10 based upon a SNP of T→A, an allele call of 11 based upon a SNP of T→A, an allele call of 12 based upon a SNP of T→A, or an allele call of 13 based upon a SNP of T→A.

Another embodiment is a method of differentiating two or more forensic DNA samples having for the D8S1179 locus an allele call of 12 based upon a SNP of A→G, an allele call of 13 based upon a SNP of G→A, an allele call of 13 based upon a SNP of C→G, an allele call of 14 based upon a SNP of G→A, an allele call of 15 based upon a SNP of A→G, an allele call of 16 based upon a SNP of A→G, or an allele call of 17 based upon a SNP of G→A.

Another embodiment is a method of differentiating two or more forensic DNA samples having for the FGA locus an allele call of 2612 based upon a SNP of G→A, or an allele call of 28 based upon a SNP of T→C.

Another embodiment is a method of differentiating two or more forensic DNA samples having for the vWA locus an allele call of 13 based upon SNPs of G→A and C→T, an allele call of 13 based upon a SNP of C→T, an allele call of 14 based upon a SNP of T→C, an allele call of 14 based upon SNPs of G→A and C→T, an allele call of 14 based upon SNPs of A→G and 2C→2T, an allele call of 15 based upon a SNP of G→A, an allele call of 16 based upon a SNP of A→G, an allele call of 17 based upon a SNP of G→A, an allele call of 18 based upon a SNP of G→A, an allele call of 18 based upon SNPs of 2A→2G, an allele call of 19 based upon SNPs of 2A→2G, an allele call of 20 based upon a SNP of T→A, or an allele call of 20 based upon SNPs of A→G

TABLE 10

| Locus | Number of Alleles with SNPs | Samples tested | % of alleles with one or more SNPs | Number of Same Length Heterozygous Loci | % of samples heterozygous with same-length alleles |
|---|---|---|---|---|---|
| D3S1358 | 115 | 95 | 60.5 | 10 | 10.5 |
| vWA | 81 | 142 | 28.5 | 11 | 7.7 |
| D13S317 | 77 | 142 | 27.1 | 7 | 4.9 |
| D21S11 | 50 | 95 | 26.3 | 6 | 6.3 |
| D5S818 | 59 | 142 | 20.8 | 10 | 7.0 |
| D8S1179 | 35 | 142 | 12.3 | 7 | 4.9 |
| D7S820 | 30 | 142 | 10.6 | 2 | 1.4 |
| D18S51 | 7 | 95 | 3.7 | 0 | 0.0 |
| FGA | 2 | 95 | 1.1 | 0 | 0.0 |
| D16S539 | 1 | 142 | 0.4 | 0 | 0.0 |

A subset of alleles from the NIST samples was sequenced for verification. The majority of these were done as base allele—variant allele pairs to verify confirm the SNP(s) and to identify the relative location. Allele sequencing confirmed the presence of a sequence polymorphism relative to the reference allele in each case and allowed the identification of its position.

TABLE 11

Selected alleles that were sequenced (bolded) from NIST samples for verification of polymorphisms observed in the ESI-TOF-MS assay.

| Sample | Well | Locus | Alleles | PP |
|---|---|---|---|---|
| NIST-PT84223 | A07 | D3S1358 | 17, 17 (2G->2A) | 3397 |
| NIST-PT84232 | A08 | D3S1358 | 15 (2G->2A), 16 (2G->2A) | 3397 |
| NIST-JT52076 | C10 | D3S1358 | 15 (G->A), 16 | 3397 |
| NIST-OT07280 | D10 | D3S1358 | 15, 16 (G->A) | 3397 |
| NIST-GT37864 | F09 | D7S820 | 9, 12 (T->A) | 2817 |
| NIST-MT97172 | G03 | D7S820 | 9, 12 | 2817 |
| NIST-JT51471 | A05 | D8S1179 | 12 (A->G), 13 | 2818 |
| NIST-WT51343 | C02 | D8S1179 | 12, 13 (G->A) | 2818 |
| NIST-TT51399 | G10 | D8S1179 | 13, 13 (C->G) | 2818 |
| NIST-PT84232 | A08 | D18S51 | 14, 20 (T->C) | 3394 |
| NIST-WT51378 | C03 | D18S51 | 12, 15 (T->G) | 3394 |
| NIST-OT05899 | C06 | D18S51 | 15, 16 | 3394 |
| NIST-PT84223 | A07 | D21S11 | 29 (A->G), 29 | 3390 |
| NIST-OT07280 | D10 | D21S11 | 30 (T->C), 30 | 3390 |

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A method for STR typing comprising:
   a) amplifying a nucleic acid from a sample with an oligonucleotide primer pair comprising a forward and a reverse primer, each between 13 and 40 nucleobases in length, wherein said forward primer is configured to hybridize within a first conserved region of said nucleic acid and said reverse primer is configured to hybridize within a second conserved region of said nucleic acid, wherein said first and said second conserved regions flank a variable nucleic acid region comprising a STR locus, wherein said amplifying generates at least one amplification product that is between about 45 and about 200 nucleotides in length;
   b) determining the molecular mass of at least one strand of said at least one amplification product by mass spectrometry; and
   c) comparing said molecular mass to a molecular mass database comprising a plurality of molecular masses of a plurality of STR-identifying amplification products indexed to said oligonucleotide primer pair and to a reference allele corresponding to said STR locus, wherein a match between said determined molecular mass and a molecular mass comprised in said molecular mass database identifies an STR allele in said sample wherein if no match is identified further comprising:
   d) calculating the base composition of said at least one strand of said at least one amplification product using said determined molecular mass, wherein said calculated base composition identifies a previously unknown allele of said STR locus; and
   e) indexing said calculated base composition to said oligonucleotide primer pair, said previously unknown allele, said determined molecular mass and said sample in a database.

2. The method of claim 1 wherein said variable nucleic acid region varies in nucleic acid sequence.

3. The method of claim 1 wherein said variable nucleic acid region varies in nucleic acid sequence among two or more alleles of said STR locus that comprise the same number of repeat units.

4. The method of claim 1 wherein said variable nucleic acid region varies in nucleic acid sequence among two or more same-length alleles of said STR locus.

5. The method of claim 1 further comprising f) determining that said sample is heterozygous at said STR locus.

6. The method of claim 5 wherein said sample has been previously characterized as homozygous for said STR locus.

7. The method of claim 1 wherein said identified STR allele comprises at least one SNP.

8. The method of claim 7 wherein said STR locus is D5S818 and said at least one SNP comprises a change from G to T or A to C, relative to a reference allele for said STR locus comprised in said database; wherein said STR locus is D8S1179 and said at least one SNP comprises a change from G to A or T to C relative to a reference allele for said STR locus comprised in said database; wherein said STR locus is vWA and said at least one SNP comprises a change from G to T, A to G, C to T, or A to C, relative to a reference allele for said STR locus comprised in said database; wherein said STR locus is D13S317 and said at least one SNP comprises a change from A to T relative to a reference allele for said STR locus comprised in said database; and/or wherein said STR locus is D7S820 and said at least one SNP comprises a change from T to A relative to a reference allele for said STR locus comprised in said database.

9. The method of claim 1, wherein said STR locus is THO1 and wherein said oligonucleotide primer pair comprises at least 70%, at least 80%, at least 90%, at least 95% or at least 100% sequence identity with a primer pair selected from the group consisting of SEQ ID NOs: 8:61, 9:61, 8:62, 9:63, 9:64, 9:65, 9:66, or 10:67; wherein said STR locus is TPDX and wherein said oligonucleotide primer pair comprises at least 70%, at least 80%, at least 90%, at least 95% or at least 100% sequence identity with a primer pair selected from the group consisting of SEQ ID NOs: 5:56, 5:57, 5:58, 5:59, 6:56, 6:57, 6:58, 6:59, or 7:60; wherein said STR locus is D8S1179 and wherein said oligonucleotide primer pair comprises at least 70%, at least 80%, at least 90%, at least 95% or at least 100% sequence identity with a primer pair selected from the group consisting of SEQ ID NOs: SEQ ID NOs: 28:85, 29:86. 30:87, or 31:88; wherein said STR locus is D5S818 and wherein said oligonucleotide primer pair comprises at least 70%, at least 80%, at least 90%, at least 95% or at least 100% sequence identity with a primer pair selected from the group consisting of SEQ ID NOs: 36:94, 37:95, 38:96, 39:97, or 40:98; wherein said STR locus is CSF1PO and wherein said oligonucleotide primer pair comprises at least 70%, at least 80%, at least 90%, at least 95% or at least 100% sequence identity with a primer pair selected from the group consisting of SEQ ID NOs: 43:102, 44:103, 45:103, 46:104, 46:103, or 47:104; wherein said STR locus is D7S820 and wherein said oligonucleotide primer pair comprises at least 70%, at least 80%, at least 90%, at least 95% or at least 100% sequence identity with a primer pair selected from the group consisting of SEQ ID NOs: 32:89, 32:90, 33:91, 34:90, 34:92, or 35:93; wherein said STR locus is D13S317 and wherein said oligonucleotide primer pair comprises at least 70%, at least 80%, at least 90%, at least 95% or at least 100% sequence identity with a primer pair selected from the group consisting of SEQ ID NOs: 22:79, 23:80, 24:81, 25:82, 26:83, or 27:84; wherein said STR locus is D16S539 and wherein said oligonucleotide primer pair comprises at least 70%, at least 80%, at least 90%, at least 95% or at least 100% sequence identity with a primer pair selected from the group consisting of SEQ ID NOs: 17:74, 18:75, 19:76, 20:77, or 21:78; wherein said STR locus is vWA and wherein said oligonucleotide primer pair comprises at least 70%, at least 80%, at least 90%, at least 95% or at least 100% sequence identity with a primer pair selected from the group consisting of SEQ ID NOs: 1:52, 2:53, 3:54, or 4:55; wherein said STR locus is FGA and wherein said oligonucleotide primer pair comprises at least 70%, at least 80%, at least 90%, at least 95% or at least 100% sequence identity with a primer pair selected from the group consisting of SEQ ID NOs: 11:68, 111:119, 112:120, or 12:69; wherein said STR locus is D21S11 and wherein said oligonucleotide primer pair comprises at least 70%, at least 80%, at least 90%, at least 95% or at least 100% sequence identity with a primer pair selected from the group consisting of SEQ ID NOs: 13:70, 109:117, 110:118, or 14:71; wherein said STR locus is D18S51 and wherein said oligonucleotide primer pair comprises at least 70%, at least 80%, at least 90%, at least 95% or at least 100% sequence identity with a primer pair selected from the group consisting of SEQ ID NOs: 15:72, 15:73, 113:121, 114:122, 16:72, or 16:73; and/or wherein said STR locus is D3S and wherein said oligonucleotide primer pair comprises at least 70%, at least 80%, at least 90%, at least 95% or at least 100% sequence identity with a primer pair selected from the group consisting of SEQ ID NOs: 41:99, 42:100, 115:123, 116:124, or 42:101.

10. The method of claim 1 further comprising repeating said steps using at least one additional oligonucleotide primer pair configured to hybridize to conserved regions that flank an STR locus selected from the group consisting of: VWA, TPDX, TH01, FGA, D21S11, D18S51, D16S539, D13S317, D8S1179, D7S820, D5S818, D3S, and CSF1PO.

11. The method of claim 10 wherein said repeating of said steps is carried out in a multiplex reaction.

12. The method of claim 1 further comprising repeating said amplifying step with at least one additional oligonucleotide primer pair, wherein at least one of said at least one additional primer is configured to hybridize to conserved regions of an AMEL locus.

13. The method of claim 12 wherein said repeating of said amplifying step is carried out in a multiplex reaction.

14. A method for STR typing comprising:
 a) amplifying a nucleic acid from a sample with an oligonucleotide primer pair comprising a forward and a reverse primer, each between 13 and 40 nucleobases in length, wherein said forward primer and is configured to hybridize within a first conserved region of said nucleic acid and said reverse primer is configured to hybridize within a second conserved region of said nucleic acid, wherein said first and said second conserved regions flank a variable nucleic acid region comprising a STR locus, wherein said amplifying generates at least one amplification product that is between about 45 and about 200 nucleotides in length;
 b) determining the molecular mass of at least one strand of said at least one amplification product by mass spectrometry;
 c) calculating the base composition of said at least one strand of said at least one amplification product using said determined molecular mass; and
 d) comparing said calculated base composition to a base composition database comprising a plurality of base compositions of STR-identifying amplification products indexed to said oligonucleotide primer pair and to a reference allele that corresponds to said STR locus, wherein a match between said calculated base composition and a base composition comprised in said base composition database identifies an STR allele in said sample, and wherein the lack of a match identifies a previously unknown allele of said STR locus; and
 f) indexing said calculated base composition to said oligonucleotide primer pair, said previously unknown allele, said determined molecular mass and said sample in a database.

* * * * *